US006602475B1

(12) United States Patent
Chiao

(10) Patent No.: US 6,602,475 B1
(45) Date of Patent: Aug. 5, 2003

(54) MULTIMEDIA AND SCENT STORAGE MEDIUM AND PLAYBACK APPARATUS HAVING ELECTROSTATIC SCENT RELEASE

(75) Inventor: Dah Shiarn Chiao, New York, NY (US)

(73) Assignee: MultiSen Technology, Inc., New York, NY (US)

( * ) Notice: Subject to any disclaimer, the term of this patent is extended or adjusted under 35 U.S.C. 154(b) by 196 days.

(21) Appl. No.: 09/713,983

(22) Filed: Nov. 16, 2000

Related U.S. Application Data

(63) Continuation-in-part of application No. 09/593,219, filed on Jun. 14, 2000, now abandoned.

(51) Int. Cl.$^7$ .............................. A61L 9/03; B05B 5/00
(52) U.S. Cl. .............................. 422/124; 422/4; 422/5; 222/146.5; 428/905; 239/690; 239/706
(58) Field of Search .............................. 422/4, 5, 124; 428/905; 239/690–708; 222/146.5

(56) References Cited

U.S. PATENT DOCUMENTS

| | | | |
|---|---|---|---|
| 2,540,144 | A | 2/1951 | Stern |
| 2,813,452 | A | 11/1957 | Laube |
| 2,905,049 | A | 9/1959 | Laube |
| 4,556,539 | A | 12/1985 | Spector |
| 4,603,030 | A | 7/1986 | McCarthy |
| 4,617,147 | A | 10/1986 | Shibanai |
| 4,629,604 | A | 12/1986 | Spector |
| 4,761,437 | A | 8/1988 | Christie |
| 4,804,821 | A | 2/1989 | Glucksman |
| 4,880,774 | A | 11/1989 | Joukou et al. |
| 4,905,112 | A | 2/1990 | Rhodes |
| D313,018 | S | 12/1990 | Funabashi |
| 5,023,020 | A | 6/1991 | Machida et al. |

(List continued on next page.)

FOREIGN PATENT DOCUMENTS

| | | |
|---|---|---|
| WO | WO 00/15268 | 3/2000 |
| WO | WO 00/15269 | 3/2000 |

*Primary Examiner*—Robert J. Warden, Sr.
*Assistant Examiner*—Sean E. Conley
(74) *Attorney, Agent, or Firm*—David M. O'Neill

(57) ABSTRACT

The multimedia and scent storage medium described herein comprises a multimedia storage region for storing multimedia information; a scent storage region for storing multiple scents; scent identification information for identifying which scents are stored in the scent storage region; and scent recovery information stored in the multimedia storage region for sequencing recovery of scents stored in the scent storage region to coincide with audio and/or video information stored in the multimedia region. Variants of the multimedia and scent-bearing medium described herein can have electrostatic scent release systems and/or capillary tube scent release systems. The integrated system described herein comprises a multimedia and scent storage medium and a multimedia player and scent recovery system for use in conjunction with the multimedia and scent-bearing medium. The multimedia and scent recovery system comprises a multimedia playback system for recovering the multimedia information stored in the multimedia storage regions of the multimedia and scent storage medium; a scent recovery system for recovering scents stored in the scent storage region of the multimedia and scent storage medium; and user input and control means for permitting the user of the integrated system to input commands for controlling the playback of multimedia information and recovery of scents stored in the multimedia and scent-bearing medium. One variant of the multimedia player and scent recovery system has a scent recovery system comprising an electrostatic scent recovery system. Another variant of the multimedia player and scent recovery system has a scent recovery system comprising a porous media scent recovery system for use with a capillary tube scent release system of a multimedia and scent-bearing medium.

100 Claims, 33 Drawing Sheets

U.S. PATENT DOCUMENTS

| | | |
|---|---|---|
| 5,071,621 A | 12/1991 | Tokuhiro et al. |
| 5,097,376 A | 3/1992 | Khan |
| 5,150,722 A | 9/1992 | Rutherford |
| 5,175,791 A | 12/1992 | Muderlak et al. |
| 5,192,342 A | 3/1993 | Baron et al. |
| D338,204 S | 8/1993 | Takao |
| 5,314,669 A | 5/1994 | Hamilton |
| D349,496 S | 8/1994 | Sato |
| 5,398,070 A | 3/1995 | Lee |
| 5,429,180 A | 7/1995 | Nishino et al. |
| 5,460,787 A | 10/1995 | Colon |
| 5,480,591 A | 1/1996 | Lagneaux et al. |
| 5,484,472 A | 1/1996 | Weinberg |
| 5,503,332 A | 4/1996 | Glenn |
| 5,565,148 A | 10/1996 | Pendergrass, Jr. |
| 5,577,156 A | 11/1996 | Costello |
| 5,590,769 A | 1/1997 | Lin |
| 5,591,409 A | 1/1997 | Watkins |
| 5,716,431 A | 2/1998 | von Glehn |
| 5,724,256 A | 3/1998 | Lee et al. |
| 5,734,590 A | 3/1998 | Tebbe |
| 5,742,256 A | 4/1998 | Wakabayashi |
| 5,805,768 A | 9/1998 | Schwartz et al. |
| 5,813,614 A | 9/1998 | Coffee |
| D399,202 S | 10/1998 | Kanatani |
| 5,848,727 A | 12/1998 | Leo et al. |
| D405,082 S | 2/1999 | Shibata |
| 5,887,118 A | 3/1999 | Huffman et al. |
| D408,408 S | 4/1999 | Ito et al. |
| 5,939,033 A | 8/1999 | Kendall et al. |
| D413,887 S | 9/1999 | Renk |
| 5,949,522 A | 9/1999 | Manne |
| 5,963,302 A | 10/1999 | Wittek |
| 5,972,290 A | 10/1999 | De Sousa |
| D416,897 S | 11/1999 | Ishii et al. |
| 6,004,516 A | 12/1999 | Rasouli et al. |
| 6,004,666 A | 12/1999 | Hornig et al. |
| 6,024,783 A | 2/2000 | Budman |
| 6,025,902 A | 2/2000 | Wittek |
| 6,041,023 A | 3/2000 | Lakhansingh |
| 6,044,200 A | 3/2000 | Hirdes |
| 6,044,202 A | 3/2000 | Junkel |
| 6,053,738 A | 4/2000 | Ivey, Jr. |
| 6,069,851 A | 5/2000 | Fenner |
| D427,988 S | 7/2000 | Haney |
| D430,444 S | 9/2000 | Allsop et al. |
| D431,543 S | 10/2000 | Yuyama |
| 6,282,458 B1 | 8/2001 | Murayama et al. |
| 6,338,818 B2 | 1/2002 | Budman |
| 6,357,726 B1 | 3/2002 | Watkins |

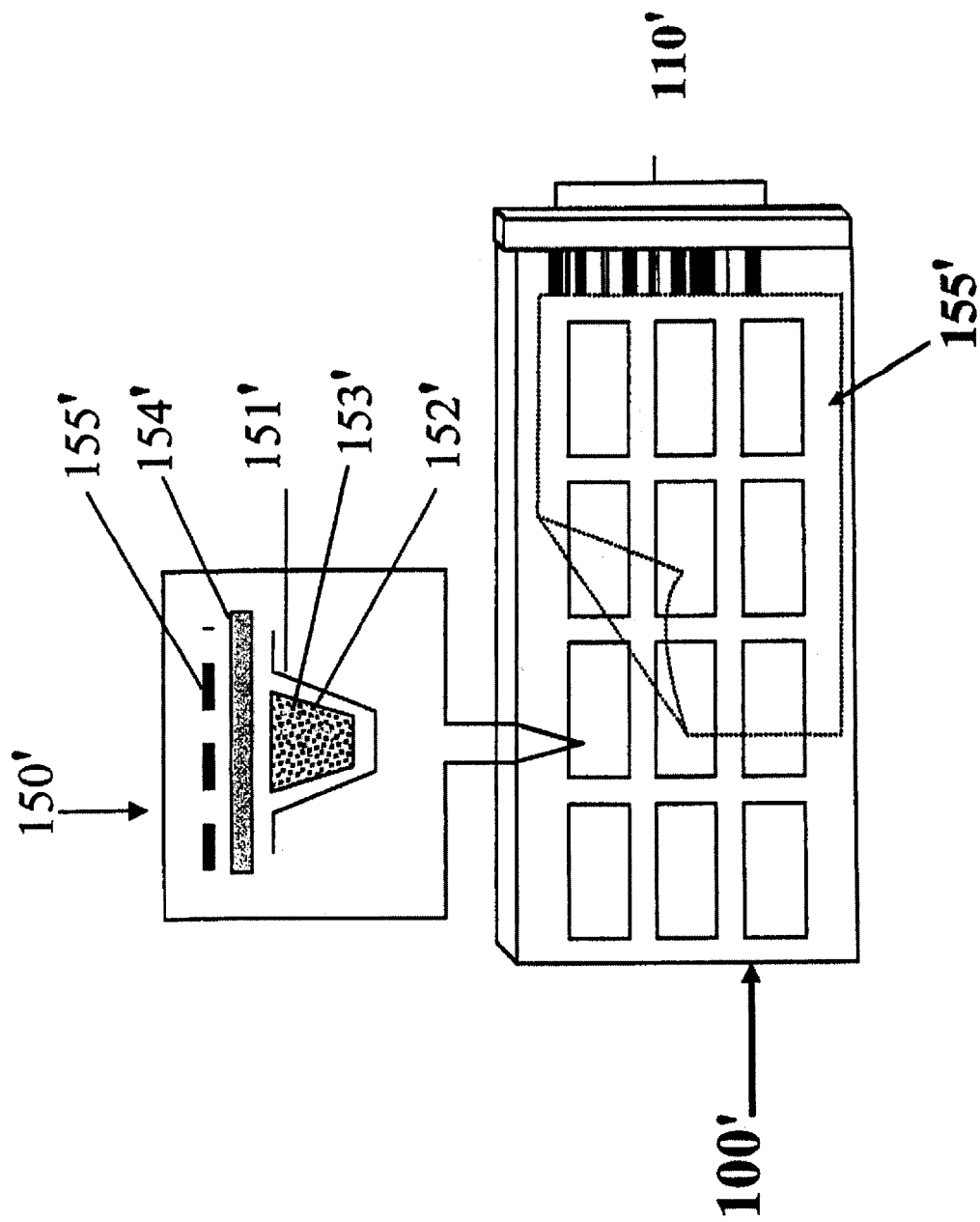

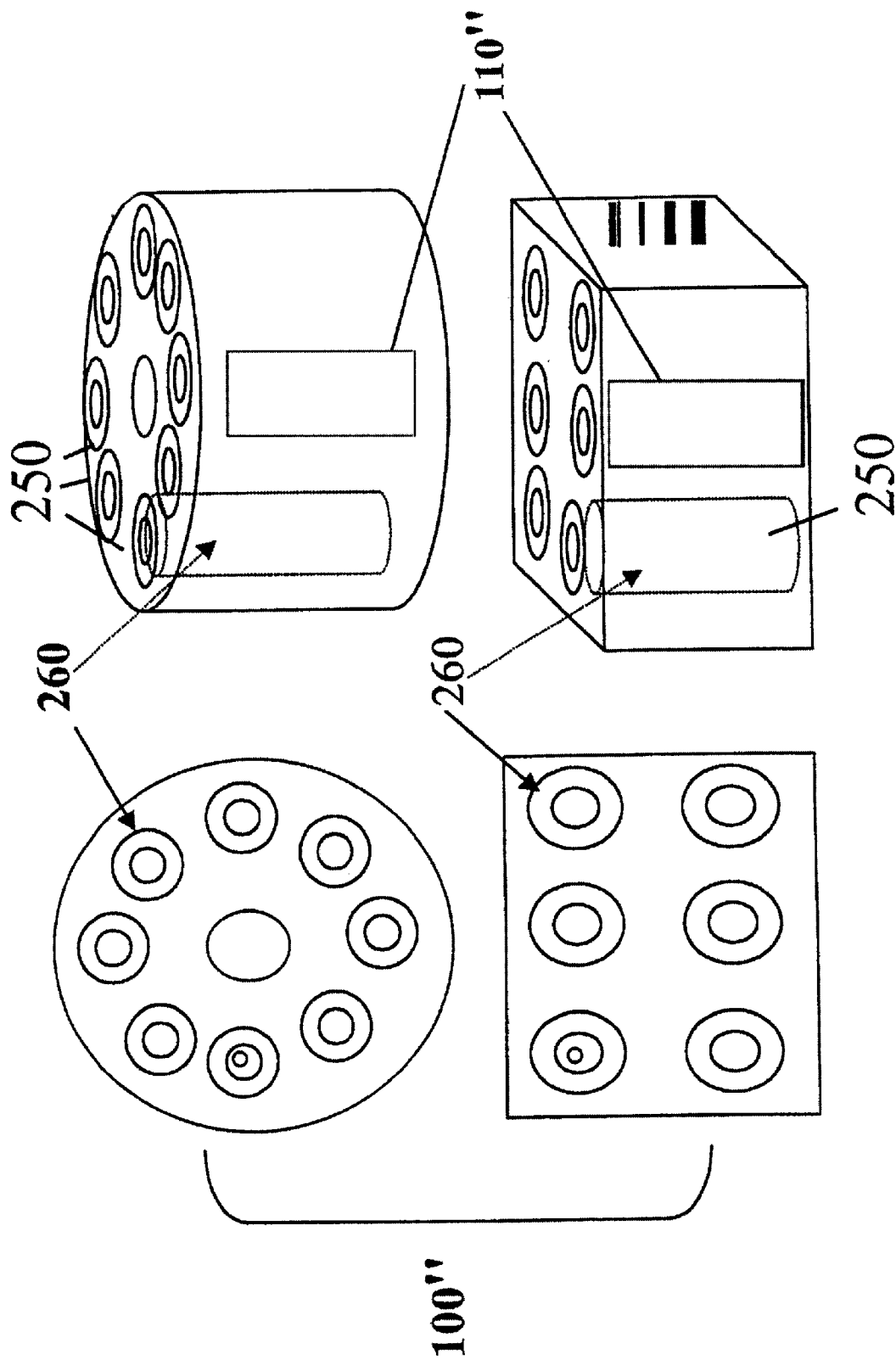

MULTIMEDIA AND SCENT STORAGE MEDIUM AND PLAYBACK APPARATUS HAVING ELECTROSTATIC SCENT RELEASE

CROSS REFERENCE TO RELATED APPLICATION

This application is a continuation-in-part of a prior U.S. application with Ser. No. 09/593219, fled Jun. 14, 2000 now abandoned and entitled "MULTIMEDIA AND SCENT STORAGE MEDIUM AND PLAYBACK APPARATUS," which is hereby incorporated by reference in its entirety as if fully restated herein.

FIELD OF THE INVENTION

The invention concerns multimedia systems having scent-dispersing capability, and multimedia and scent storage media for use in conjunction with integrated multimedia playback and scent recovery systems. Certain embodiments of the present invention more particularly concern multimedia and scent storage media for use with multimedia playback and scent recovery systems having electrostatic scent release capability. Other embodiments of the present invention more particularly concern multimedia and scent storage media having capillary-tube scent release systems. Further embodiments of the present invention more particularly concern stand-alone kiosks having multimedia playback and scent recovery capability for use in providing multimedia virtual-reality experiences comprising audio, visual and scent information in publicly-accessible locations.

BACKGROUND OF THE INVENTION

Multimedia sources heretofore usually have been limited to audio or visual media. For example, the public is widely familiar with television, high fidelity audio, FM radio, and more recently, the Internet (which typically is audio-visual in format). As a result, the public has been limited to audio or visual stimulation. There has not been widespread media available for providing an olfactory ("scent") stimulation, particularly scent media that are intended to operate in synchronism with audio or visual sources. Thus users are prevented from experiencing a complete multi-sensory experience that would provide an authentic virtual reality experience.

Known prior art is deficient for many reasons. For example, the prior art shows little or no appreciation for the need to identify scent sources stored on media so that multiple scents stored in them may be recovered in a pre-programmed sequence. Other prior art is designed for use in large auditoriums or movie theaters and comprise multiple, separate and expensive components that are impractical for personal or home use. The prior art also shows no appreciation of the desirability to provide user-specifiable scent sequences for use in combination with audio or visual multimedia sources.

More specifically, U.S. Pat. No. 5,887,118 to Huffman et al. teaches an olfactory card including a scent producing member. Although the olfactory card of Huffman can be used for personal applications, it suffers from several limitations that prevent it from being of widespread use. The most noticeable limitation is that it is intended for use with PCMCIA slots in portable computers. PCMCIA cards are noticeably small and provide little room for storing the volume of scents that would be required for use in home multimedia applications. Further, in order to properly operate with the PCMCIA interface, the olfactory card requires a separate interface and on-board processing hardware and, as a result,;represents an expensive and complex solution.

In addition, the PCMCIA card of U.S. Pat. No. 5,887,118 includes both the scent and the scent recovery apparatus in a single housing. Since the scent-recovery apparatus and associated electronics are relatively expensive, a user is presented with a dilemma. After the scent has been exhausted, the user either has to dispose of the PCMCIA card and purchase a new one with fresh scent, or send the PCMCIA card to a commercial entity for refilling. Either of these are less acceptable than an inexpensive, disposable alternative. Further, Huffinan et al. does not teach any means for editing pre-programmed scent recovery sequences so that a user may "customize" scent recovery sequences for use with known multimedia sources.

U.S. Pat. No. 6,004,516 to Rasouli et al. discloses a scent-bearing disk and associated playback apparatus. The system disclosed in U.S. Pat. No. 6,004,516 shows no appreciation of scent recovery and sequencing problems. For instance, there is no teaching of how separate scents on the disk are tagged so that they can be rapidly and accurately accessed during playback of multimedia content so that the scent recovery sequence coincides with the multimedia content.

U.S. Pat. No. 4,629,604 describes a player for a multi-aroma cartridge with individual electric heaters. The player disclosed therein provides no scent identification information for various replacement cartridges, nor is it an Internet-compatible device. Not having any tag or scent identification information limits the flexibility of the player disclosed in U.S. Pat. No. 4,629,604.

U.S. Pat. No. 5,949,522 describes a device that can deliver various combinations of scent in rapid succession to a user's nose in conjunction with videographic images or sounds. Through proper control of valves and compressed air, the system described in U.S. Pat. No. 5,949,522 can use liquid fragrance without heating. U.S. Pat. No. 5,949,522 shows no appreciation of the need for tag or fragrance identification information to control the sequential recovery of fragrances from the fragrance containers. This limits the modes of operation and in turn the flexibility of the system. Furthermore, the whole system requires an uncomfortable and unsanitary nose tube.

U.S. Pat. No. 5,591,409 describes a method and apparatus for "metered spray" aroma delivery system for use with an entertainment system. The method and apparatus disclosed in U.S. Pat. No. 5,591,409 uses liquid fragrance without heating, and a limited number of fragrance containers without tag or scent identification information. This again limits the flexibility of operation of the device.

U.S. Pat. No. 6,053,738 describes an apparatus for reproducing smells and flavors using a cylindrical housing containing smell and flavor cartridges. U.S. Pat. No. 6,053,738 provides no tag information for future smell and taste replacements.

U.S. Pat. No. 5,565,148 describes a multiple aroma delivery apparatus with a plurality of separate, cylindrically-shaped chambers. Limiting the arrangement of chambers and valves also decreases the variety of scents deliverable by the system.

U.S. Pat. No. 5,734,590 describes a device comprising a plurality of stimulus generators including a scent generator, with a micro-encapsulated scent carrier or a block of spray tubes. The utility signal source is from a separate recording medium. The system disclosed in U.S. Pat. No. 5,734,590 provides no tag or scent identification information for the scent carrier and lacks the ability to be re-programmed.

U.S. Pat. No. 6,025,902 describes a process for increasing the sensual perception of visual, acoustic, and odor stimulation in a theatre. U.S. Pat. No. 5,963,302 also describes a process for increasing the sensual perception of visual, acoustic, and scent stimulation in a theatre, as well as various scent storing and releasing arrangements.

U.S. Pat. No. 6,024,783 describes a multimedia-linked apparatus for delivery of real-time or stored aroma. The aroma-producing system is a multi-chamber mechanism. The aroma-emitting material is individually placed above each heater in each releasing chamber, and each chamber has its own air-exhausting unit and a controlled opening door.

However, the system disclosed in U.S. Pat. No. 6,024,783 is based on scent or aroma carriers (i.e., a card, disk, cartridge, container, or cylinder) that do not carry any tag or scent identification information within or on the scent or aroma carriers. Without any tag or scent identification information, the control device of the prior art cannot receive the tag information of scents or aroma. Thus the scents cannot be recovered in a preprogrammed sequence.

Providing tag or scent identification information for the scent or aroma carriers with a controller would generate more variety and precision with respect to scent or aroma recovery in a very cost-efficient way. In addition, the multimedia information recovered from the multimedia medium of the scent or aroma carriers would create another option for users, as a stand-alone multimedia playback and scent recovery device. The prior art shows no appreciation of these modes of operation.

There are different methods and apparatus for impregnating scent medium on a disk or a card to make a Scent Disk or a Scent Card or a Scent Cartridge. For example, U.S. Pat. No. 5,939,033 describes a method and apparatus for impregnating solid materials (e.g. hydrogen peroxide) on a disk allowing conductive foil to conduct heat. U.S. Pat. No. 5,972,290 describes a process and apparatus for programmed scent delivery by piercing capsules of scented substrates and compounds embedded on a disk. U.S. Pat. No. 5,848,727 discloses a strip dispenser that is manually generated. U.S. Pat. No. 5,460,787 presents a method and apparatus for an insertable scented card. U.S. Pat. No. 6,044,202 describes an apparatus and method for a heated deodorizing scent card with a body of fragrance compound and an embedded plurality of individual and heat generating resistors operated via a thermistor.

There are also different methods and apparatus for improving scent cartridges. U.S. Pat. No. 5,314,669 describes a multi-layer cylindrical system to dispense different scents without changing the retaining carriage. U.S. Pat. No. 5,023,020 also describes a cylindrical receptor with plural containers for receiving scents. U.S. Pat. No. 5,742,256 describes a computer-controlled metered-delivery device, which dispenses scents onto a rotating absorptive porous member.

There are different methods and apparatus for applying gas permeable membrane materials to control scent release. U.S. Pat. No. 5,150,722 describes a method for effecting the controlled release of fragrance in a relatively "long period." U.S. Pat. No. 5,480,591 describes a "naturally" diffusing diffuser with membranes on the flank.

With respect to recording media with scent, U.S. Pat. No. 5,097,376 describes a container with a fragrance material, in particular, a tape cassette with embedded scent. However, the embedded fragrance only serves for identification purposes and shows no appreciation of the use of multiple scents. U.S. Pat. No. 6,004,666 discloses a data carrier having fracturable microencapsulated scents releasable upon fracturing the micro-capsules.

Timing-controlled scent-diffusion methods have been used to diffuse scents in air, with some attempts to develop aroma-delivering apparatuses with timing control. U.S. Pat. No. 4,603,030 describes a scent-emitting system to propel scents in response to a programmed sequence of scents of predetermined duration. U.S. Pat. No. 5,175,791 describes a stepped power control fragrance diffuser with fragrance-emitting blocks within certain preprogrammed time period. U.S. Pat. No. 5,805,768 describes an apparatus with a rotating plurality of receptacles for various scents, allowing the user to pre-select a variety of aroma to be delivered at predetermined time intervals.

There have been some attempts to develop a neutralizing method to increase the sensitivity and perception level between scent releasing. U.S. Pat. No. 5,429,180 describes a process and apparatus for introducing refreshing-type aromatic agent between relaxing-type aromatic agents in a repetition of cycles. This prior art does not provide neutralizing or masking function that synchronizes with multimedia presentation.

Thus, a multimedia and scent recovery system that is capable of storing multiple scents in sufficient quantity is desirable so that a user may use it in a home environment in combination with a multimedia playback means to create a realistic virtual reality experience that may include audio or visual stimulation in combination with scent stimulation. A relatively simple storage medium that combines both multimedia information and multiple scents that would also facilitate a realistic virtual reality experience that may be repeated over and over again is also desired. In addition, an editing means that permits a user to depart from a preprogrammed scent recovery sequence in. order so that the user may create a "customized" virtual reality experience, including multimedia and scent elements, is also desired.

In addition, multimedia and scent-bearing media having improved scent-release systems are also desired. Further, fully-integrated and stand-alone systems that are capable of providing a complete multimedia experience comprising audio, visual and scent stimulation are also desired.

SUMMARY OF THE INVENTION

The limitations of the prior art are overcome in the following embodiments of the present invention. A first embodiment of the present invention comprises a multimedia and scent storage medium, further comprising a multimedia storage region for storing multimedia information; a scent storage region for storing multiple scents; scent identification information for identifying which scents are stored in the scent storage region; and scent recovery information stored in the multimedia storage region for sequencing recovery of scents stored in the scent storage region to coincide with audio and/or video information stored in the multimedia region. The multimedia information stored in the multimedia region may comprise audio, video, textual, graphical or photographic information.

A variation of the first embodiment comprises a multimedia and scent-bearing medium having a plurality of recessed three-dimensional regions for storing separate scents; inert storage media deposited within the regions for storing separate scents; and a gas permeable membrane placed over upwardly-facing openings of the recessed three-dimensional regions. The gas. permeable membrane may comprise a microporous or macroporous polymer.

Another variation of the first embodiment of the present invention comprises the multimedia and scent-bearing media of the foregoing embodiments in combination with scent recovery sequence information for controlling the sequential recovery of scents stored in the scent storage region.

In a further variation of the first embodiment of the present invention, the scent recovery sequence information of the preceding embodiments further facilitates the simultaneous recovery of scent and multimedia information to provide an immersive, multi-sensory experience. In this further variation scent-neutralizing or scent-masking materials are also stored in the multimedia and scent-bearing medium. The scent-neutralizing or scent-masking material is used to mask previous scents recovered from the multimedia and scent-bearing medium before additional scents are released.

In yet another variation of the first embodiment of the present invention, the multimeidia and scent-bearing medium comprises a housing having multiple storage slots; a plurality of scents stored in canisters within each slot; and a scent identification means. Each canister has a release valve for facilitating the release of scents from the canister. The scent identification means identifies which scents are stored in which slots. Bar codes may be used as the scent identification means.

Further variations of the first embodiment of the present invention overcome the limitations of the prior art with respect to the storage of volatile scents. In one embodiment the multimedia and scent-bearing medium is stored in a storage case having overlapping seals to prevent scent from escaping from the scent storage region. In another embodiment a gas impermeable membrane is placed over the gas permeable membrane covering the recessed three-dimensional regions (each of which stores a separate scent) of the multimedia and scent-bearing medium to prevent scent from escaping from the recessed three-dimensional regions.

A second embodiment of the present invention comprises an integrated system having a multimedia and scent storage medium and a multimedia player and scent recovery system for use in conjunction with the multimedia and scent-bearing medium. The multimedia playback and scent recovery system of the second embodiment comprises a multimedia playback system for recovering the multimedia information stored in the multimedia storage regions of the multimedia and scent storage medium; a scent recovery system for recovering scents stored in the scent storage region of the multimedia and scent storage medium; and user input and control means for permitting the user of the integrated system to input commands for controlling the playback of multimedia information and recovery of scents stored in the multimedia and scent-bearing medium.

A variation of the second embodiment comprises a multimedia player having an optical (e.g. CD, DVD, or bar code) or magnetic playback system (e.g. floppy, hard disk, or tape) for retrieving the encoded multimedia information. The audio signal recovered from the multimedia information can be played back through a speaker system that is connected to an amplifier system. The video signal recovered from the multimedia information can be played back through a visual display system (e.g. a monitor or a LCD).

Another variation of the second embodiment of the present invention comprises an interactive playback system to edit the pre-programmed scent recovery sequence information retrieved from the multimedia and scent-bearing medium for controlling the sequential recovery of scents stored in the scent storage region. The editing function of the present invention allows a user to create a user-specified scent recovery sequence by editing the scent recovery sequence information recovered from the multimedia and scent-bearing medium. Using the editing function, a user may alter the order of scent recovery; change the duration of recovery of individual scents, or substitute other scents for those specified by the pre-programmed scent recovery sequence information. The editing means also permits a user to create entirely new scent recovery sequences to be used in conjunction with multimedia information.

In a further variation of the second embodiment of the present invention, the scent recovery system may comprise single or multiple, movable heating elements. The scent recovery system converts the scent recovery sequence information recovered from the multimedia and scent storage medium into control signals for controlling the operation of the heating elements. Upon receiving the control signal, the heating elements (e.g. laser or infrared) will move to a predetermined position so that they may heat and thereby release the heat-releasable scents stored within the scent-bearing medium. Through a ductwork immediately adjacent to the multimedia and scentbearing medium, a fan will facilitate the venting of scents to the user of the integrated system.

Yet another variation of the second embodiment of the present invention comprises an input connection for accepting a multimedia signal from a remote source. The remote multimedia source may comprise radio, television, or satellite transmitters, or publicly switched telephone networks (PSTN) or cable systems, or LAN, or WAN, or a computer. The remote multimedia information may comprise separately-recoverable segments and may further comprise audio, video textual, graphical or photographic information.

Still further variations of the second embodiment of the present invention overcome the limitations of the prior art with respect to the variety of scents stored in the scent storage media. By retrieving the tagging, scent recovery sequence, and the multimedia information from the multimedia medium or remote source and storing all of this information in a local storage system, the present invention not only provides precise coupling between scents and scent recovery sequence information but also allows the user to edit or transmit specified scent recovery sequences and multimedia information to another user.

A third alternate embodiment of the present invention comprises a multimedia and scent storage medium, which further comprises a multimedia storage region for storing multimedia information; a scent storage region for storing multiple scents; scent identification information for identifying which scents are stored in the scent storage region; scent recovery information stored in the multimedia storage region for sequencing recovery of scents stored in the scent storage region to coincide with audio and/or video information stored in the multimedia region; and an electrostatic scent release means for assisting in the release of scent from the scent storage region. The electrostatic scent release means of the third alternate embodiment preferably comprises an electrode immersed in the liquid or gel scent that operates in conjunction with an electrode of a multimedia playback and scent recovery system. During operation, the multimedia playback and scent recovery system would impart a potential difference between the electrodes. The potential difference initiates electrostatic scent release by imparting a charge to individual scent molecules. After the scent molecules vaporize, the imparted charge assists in dispersing the scent over a greater region, since individual scent molecules will repel one another.

Variants of the third embodiment comprise a multimedia and scent-bearing medium having a plurality of recessed three-dimensional regions for storing separate scents; a gas permeable membrane placed over upwardly-facing openings of the recessed three-dimensional regions, and a scent-release electrode placed within each of the recessed three-dimensional regions for providing an electrostatic scent release capability. Preferably, the multimedia and scent-storage medium is in the form of a disc. In this variant the electrostatic scent release means comprises a corona electrode and associated control circuitry. The corona electrode is intended to operate in conjunction with a counter electrode, which may be part of the multimedia and scent bearing medium, or in other variants may be part of a multimedia playback and scent recovery system. A separate multimedia playback and scent recovery system would impart a potential difference between the corona electrode and the counter electrode. Preferably, the counter electrode comprises a plate-like electrode disposed above the gas permeable membrane, and the corona electrode comprises a pin-shaped electrode positioned within the recessed, three-dimensional region. The counter electrode is placed in close proximity to ductwork for venting scent recovered from the scent-bearing region by the corona discharge to a user. In one such variant, the counter electrode has one or more small holes so that charged scent molecules may pass through the electrode and be entrained in the flow of air maintained in the ductwork by a fan. During operation a corona discharge is maintained between the electrodes. The means for sustaining a corona discharge comprises an high voltage power supply, preferably of 1–20 kilovolts.

Additional variants of the third alternate embodiment comprise a multimedia and scent-storage medium in the form of a rectangular card with a plurality of rectangular recessed three-dimensional regions. Further variants of the third embodiment comprise a cartridge/canister system comprising a plurality of scent canisters positioned within the cartridge, and having an electrostatic scent release means for imparting a charge to scent released from the canisters to improve the efficiency of scent release. The electrostatic scent release means preferably comprises a corona electrode, counter electrode, and associated control circuitry for imparting a potential difference between the electrodes to sustain a corona discharge.

Even further embodiments of the third variant comprise an electrostatic scent release means comprising two electrodes and associated circuitry that would forego the need for a separate electrode in a multimedia playback and scent recovery system. The multimedia playback and scent recovery system need merely energize the electrodes through the associated circuitry to cause scent release. In this variant both the corona electrode and the counter electrode would be positioned within the recessed three-dimensional region. One or more holes are provided for in the counter electrode so that charged scent molecules may pass through the counter electrode and be entrained into the gas air flow initiated by the ductwork and associated fan placed in close proximity to the gas permeable membrane enclosing the recessed three-dimensional region.

A still further variant of the third embodiment comprises a scent bearing medium; scent identification means for identifying scents stored in the scent bearing medium; and an electrostatic scent release means for releasing scent from the scent-bearing medium. This variant does not contain multimedia information but can be used with multimedia information recovered from other sources (e.g., the Internet, CDs or DVDs) to create a virtual reality experience having audio, visual and scent stimulation. The scent identification means comprises scent identification information encoded in a scent identification data storage region that can be used to identify scent stored in the scent storage region, identify scent location in the scent storage region if multiple scents are included, and/or be used to sequence scent recovery to coincide with the multimedia information recovered from the remote source. The scent identification means can be optically, magnetically, or electrically recorded in the scent-bearing medium using well-known data recording techniques and formats disclosed throughout this application. In other variants, the scent identification means further comprises scent recovery sequence information for use in controlling the sequence of scent recovery from the scent-bearing medium.

A fourth alternate embodiment of the present invention comprises a multimedia and scent storage medium, which further comprises a multimedia storage region for storing multimedia information; a scent storage region for storing multiple scents; scent identification information for identifying which scents are stored in the scent storage region; scent recovery information stored in the multimedia storage region for sequencing recovery of scents stored in the scent storage region to coincide with audio and/or video information stored in the multimedia region; and wherein the scent storage region comprises at least one enclosure having a capillary tube extending therefrom. The enclosure can be in the form of a tube, ampule, three-dimensional sector as in the case of a disk, or any three-dimensional shape suitable for storing scent in liquid form. The capillary tube extending from the enclosure causes capillary action during scent recovery to aid in scent release. In typical operation, a multimedia playback and scent release system would bring a porous media into very close proximity to the end of the capillary tube. Scent at the end of the capillary tube would contact the porous media and capillary action would cause the scent to pass into the porous media as a first step in scent release. Variants of the fourth embodiment comprise a plurality of enclosed regions for storing a plurality of scents wherein each of the enclosed regions have a capillary tube extending therefrom.

Another variant of the fourth embodiment comprises a scent-bearing medium which further comprises a plurality of enclosed regions for storing a plurality of scents wherein each of the enclosed regions have a capillary tube extending therefrom and scent identification means for identifying scents stored in the enclosed regions of the scent bearing medium. This variant does not contain multimedia information, but can be used with multimedia information recovered from other sources (e.g., the Internet, CDs or DVDs) to create a virtual reality experience having audio, visual and scent stimulation. The scent identification means comprises scent identification information that can be used to sequence scent recovery to coincide with the multimedia information recovered from the remote source. In other variants, the scent identification means may further comprise scent recovery sequence information for use in controlling the sequence of scent recovery from the scent-bearing medium.

A fifth alternate embodiment of the present invention comprises a multimedia and scentbearing medium having a rigid housing for use in combination with the multimedia and scentbearing medium having electrostatic scent release. The rigid housing has a retractable door that shields the multimedia and scent-bearing medium when not in use.

When placed in a multimedia playback and scent recovery system, the retractable shield retracts, exposing at least a portion of the multimedia and scent-bearing medium so that scent may be recovered by the multimedia playback and scent recovery system from the multimedia and scent-bearing medium.

A sixth alternate embodiment of the present invention comprises a multimedia playback and scent recovery system wherein the scent recovery system comprises, in part, an electrostatic scent release system. The electrostatic scent release system of the multimedia playback and scent recovery system comprises at least one electrode intended to operate in cooperation with an electrode positioned in a multimedia and scent-bearing medium. The electrostatic scent release system also comprises an electrical system for imparting a potential difference between the electrode of the multimedia playback and scent recovery system and the electrode of the multimedia and scent-bearing medium. The potential difference set up between the two electrodes imparts an effective charge to individual scent molecules, thereby assisting in the vaporization of the scent. Vaporized scent molecules then pass through the semi-permeable membrane of the multimedia and scent-bearing medium. The vaporized scent molecules continue moving toward the electrode of the multimedia playback and scent recovery system until they come under the influence of the venting system of the multimedia playback and scent recovery system. The venting system comprises, in part, ductwork and an exhaust fan for exhausting the vaporized scent to the atmosphere in close proximity to a user of the multimedia playback and scent recovery system. The electrode of the scent recovery system of the multimedia playback and scent recovery system preferably comprises a counter electrode for operation in conjunction with a corona electrode of the multimedia and scent-bearing medium.

A variant of the sixth alternate embodiment comprises a multimedia playback and scent recovery system having an electrostatic scent release system comprised of a plurality of electrodes. The plurality of electrodes can operate in conjunction with a plurality of electrodes in a multimedia and scent-bearing medium so that multiple scents may be released from the multimedia playback and scent recovery system at the same time.

Another variant of the sixth alternate embodiment comprises a multimedia playback and scent recovery system having an electrostatic scent release system intended for use in conjunction with a multimedia and scent-bearing medium wherein the multimedia and scent bearing medium has at least a pair of electrodes and associated control circuitry. The electrostatic scent release system of this variant need merely impart a potential difference through the control circuitry of the multimedia and scent-bearing medium to accomplish scent release.

A still further embodiment of the sixth alternate embodiment comprises a multimedia playback and scent recovery system for use with a scent-bearing medium having scent identification information and multimedia information recovered from other sources (e.g., the Internet, CDs or DVDs), wherein the multimedia information is intended to be used with scents recovered from the scent-bearing medium. The multimedia playback and scent recovery system further comprises an electrostatic scent release system, and a scent identification information recovery means for recovering scent identification information from the scent-bearing medium. This information is used by the multimedia playback and scent recovery system to identify, access and release the correct scent to coincide with the appropriate multimedia information during a synchronized multimedia playback and scent release sequence.

A seventh alternate embodiment of the present invention comprises a multimedia playback and scent recovery system for use in conjunction with a multimedia and scent-bearing medium having a capillary tube scent release system. The multimedia playback and scent recovery system comprises, in part, a scent release system. The scent release system comprises a porous media that aligns opposite an opening in the capillary tube of the capillary tube scent release system of the multimedia and scent-bearing medium. Scent stored in the scent-bearing medium passes through the capillary tube and into the porous media of the scent release system of the multimedia playback and scent recovery system. The scent release system of the multimedia playback and scent recovery system further comprises an exhaust system comprising ductwork and an exhaust fan positioned immediately adjacent to the porous media for entraining scent in the porous media into air passing through the ductwork. The entrained scent is then vented to the atmosphere in the vicinity of a user of the multimedia playback and scent recovery system to create an olfactory sensation for the user.

A variant of the seventh alternate embodiment further comprises motor means for moving the porous media back and forth between positions where it is close to the capillary tube of the multimedia and scent bearing medium (and therefore can recover scent from the multimedia and scent-bearing medium) to a position where it can no longer recover scent from the multimedia and scent-bearing medium.

A further variant of the seventh alternate embodiment comprises a plurality of porous media for use in combination with a multimedia and scent-bearing medium having a plurality of capillary scent release tubes. At least one of the porous media would align with each of the capillary tubes during scent release.

A still further variant of the seventh alternate embodiment comprises, in part, an electrostatic scent release system that operates in conjunction with the porous media to assist in scent release. The electrostatic scent release system of this variant imparts a charge to the scent after it has been recovered from the multimedia and scent-bearing medium and as it is being entrained in air in preparation for venting from the multimedia playback and scent recovery system. The electrostatic scent release system may comprise a corona electrode, counter electrode and high voltage power supply for charging the scent molecules released from the porous media.

An even further variant of the seventh alternate embodiment comprises a multimedia playback and scent recovery system for use with a scent-bearing medium having scent identification information and multimedia information recovered from other sources (e.g., the Internet, CDs or DVDs), wherein the multimedia information is intended to be used with scents recovered from the scent-bearing medium. The multimedia playback and scent recovery system further comprises a porous media scent release system, and a scent identification information recovery means for recovering scent identification information from the scent-bearing medium. This information is used by the multimedia playback and scent recovery system to identify, access and release the correct scent to coincide with the appropriate multimedia information during a synchronized multimedia playback and scent release sequence.

An eighth alternate embodiment of the present invention comprises a kiosk comprising a multimedia playback and scent recovery system for use with a multimedia and scentbearing medium. Preferably the system comprises a housing; an audio and video playback system for recovering multimedia information; a monitor for displaying video information; speakers for playing audio information; and a scent dispersal system for dispersing scent in the vicinity of the kiosk. Variants of the seventh alternate embodiment further comprise an on-demand playback control system for receiving commands from users desiring to experience the multimedia and scent experience created by the kiosk. Additional variants of the seventh alternate embodiment of the present invention comprise an automatic playback system with human proximity sensor. The human proximity sensor detects when humans (e.g., customers) are close to the kiosk and automatically initiates a multimedia playback and scent recovery sequence. The human proximity sensor may comprise an infrared sensor, a motion sensor, or a voice sensor. A still further embodiment of the present invention comprises a counter-mounted multimedia and scent recovery system. An even further embodiment of the present invention comprises a booth having a multimedia playback and scent recovery system.

A ninth alternate embodiment comprises a head-mounted multimedia and scent recovery system combining headphones; a video display; and a scent recovery and dispersal system for venting scent directly to a user's nose.

One of ordinary skill in the art will understand that each of the alternate embodiments can be practiced either singly, or in combination with one or more alternate embodiments (or with individual features of alternate embodiments), or with other multimedia and scent-bearing media and/or multimedia playback and scent recovery systems. In addition, one of ordinary skill in the art will understand that the preceding alternate embodiments can be combined in various ways to accomplish different system objectives. Further, one of ordinary skill in the art will understand that the means for accomplishing the functionality described herein can be distributed in various ways, e.g., combined into a single stand-alone system or distributed among a plurality of separate, but interconnected and communicating, systems. All of these variants are within the scope of the present invention.

Thus, it is seen that embodiments of the present invention overcome limitations of the prior art. Known scent storage media do not include information identifying either which scents are stored or what sequence the scents are to be recovered from the scent storage media. In contrast, the present invention stores scent identification and scent recovery sequence information in the multimedia and scent storage medium, thereby permitting the synchronized recovery of multimedia information and scents stored in the multimedia and scent storage medium. This manner of operation provides an immersive, multi-sensory experience.

Other known scent storage media require complex circuitry, processing capability, and heating elements for releasing scent from the scent storage media. Such media are complex in construction, expensive to manufacture, and expensive to purchase. In contrast, the multimedia and scent storage medium of the present invention is designed to operate with an integrated multimedia playback and scent recovery system that includes playback and scent recovery hardware. In consequence, the multimedia playback and scent recovery hardware need not be positioned on the multimedia and scent storage medium. As a result, the multimedia and scent storage medium of the present invention is simple in construction, inexpensive to manufacture, and inexpensive to purchase.

There are no known, integrated multimedia playback and scent recovery systems. As a result, it is difficult, if not impossible, to create synchronized multimedia playback and scent recovery sequences that are repeatable. Further, it is also difficult to develop new synchronized multimedia playback and scent recovery sequences. In contrast, the multimedia playback and scent recovery system of the present invention is designed to operate with multimedia and scent storage media that store scent identification and scent recovery sequence information. As a result, a user of the multimedia playback and scent recovery system can "replay" synchronized multimedia and scent recovery sequences to provide an immersive, multi-sensory experience that is repeatable. Further, the multimedia playback and scent recovery system of the present invention further comprises scent recovery sequence information storage means, and scent recovery sequence information editing means. In contrast to the prior art, this feature of the present invention permits a user to edit pre-programmed multimedia playback and scent recovery sequences to create new, "custom," user-specified multimedia playback and scent recovery sequences. Further, this feature of the present invention also permits a user to create entirely new multimedia playback and scent recovery sequences.

The present invention also provides scent release alternatives that have enhanced scent release performance over the prior art. For example, the electrostatic scent release system of the multimedia playback and scent recovery system of the present invention imparts a charge to scent molecules, which causes individual scent molecules to repel one another, thereby improving the efficiency and effectiveness of scent release through improved dispersion. In other words, more scent reaches a greater area than in other scent release systems.

The present invention also provides a significant advance over the prior art in that a single, stand-alone system made in accordance with the present invention is capable of providing a complete multimedia experience comprising audio, visual and scent stimulation. When constructed in the form of a compact kiosk, this system can be placed, in retail establishments to assist in the marketing of perfumes. For example, in one implementation, the system would replay audio and visual marketing information in combination with a controlled scent (i.e., a sample of the perfume) release that is the subject of the audiovisual information. In other implementations, the scent recovery system can be combined with an interactive game booth, thereby providing a game experience that comprises audio, visual and olfactory stimulation.

BRIEF DESCRIPTION OF THE FIGURES

The above and other objects and advantages of this invention will be apparent upon consideration of the following detailed description, taken in conjunction with the accompanying drawings in which like reference characters refer to like elements throughout, and in which:

FIG. 3 depicts a top view of an alternate multimedia and scent-bearing medium 100', and a detail view of scentbearing medium 150', made in accordance with a first alternate embodiment of the present invention;

FIG. 4 depicts multiple views of an alternate multimedia and scent-bearing medium 100" made in accordance with a first alternate embodiment of the present invention;

DETAILED DESCRIPTION OF THE PREFERRED EMBODIMENTS

I. First Alternate Embodiment

Figure 1:
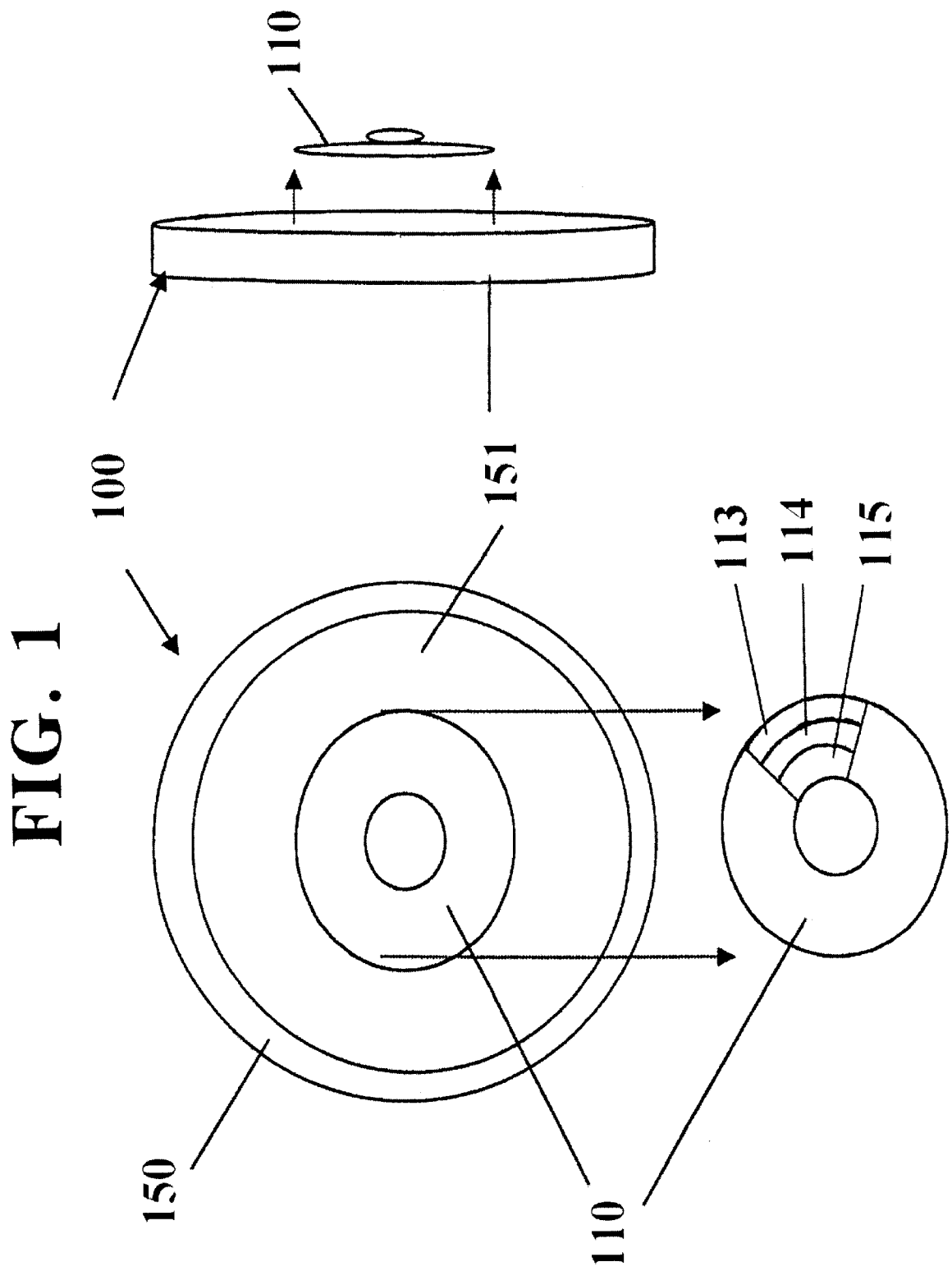
FIG. 1 depicts top and side views of a multimedia and scent-bearing medium 100 made in accordance with a first alternate embodiment of the present invention.
Figure 2A:
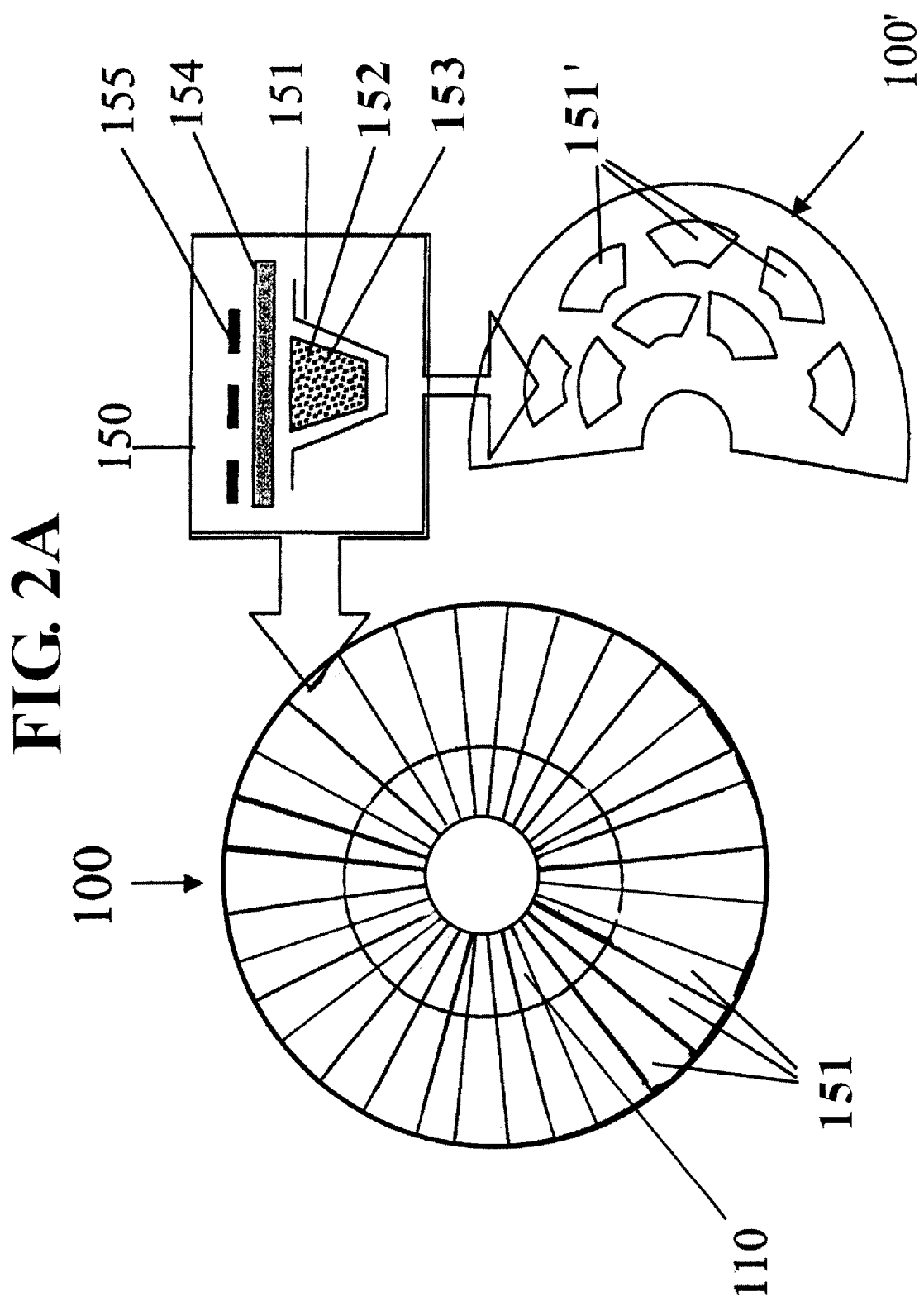
FIG. 2A depicts a top view of a multimedia and scent-bearing medium 100, and in particular a cross-sectional view of a scent-bearing medium 150, made in accordance with a first alternate embodiment of the present invention.

A first alternate embodiment of the present invention comprises a multimedia and scent-bearing medium 100 as depicted in FIGS. 1 and 2A. The multimedia and scent-bearing medium 100 comprises two elements: a multimedia storage medium 110 and a scent-bearing medium 150. The scent-bearing medium 150 further comprises a plurality of recessed three-dimensional regions 151 each for storing a separate scent.

Deposited within each three-dimensional region is an inert storage medium 152. The inert storage medium 152 is not reactive with the scents that will be stored within it. The three-dimensional region is formed in the plastic housing of the multimedia and scent-bearing medium 100. A plurality of radially-extending three-dimensional regions are shown in the multimedia and scent-bearing medium 100 depicted in FIG. 2A. The three-dimensional regions may also take concentric form 151' as shown in the partial view of the multimedia and scent-bearing medium 100' also shown in FIG. 2A. The inert storage medium 152 may be a polymer gel and may take other forms that are well known to those of ordinary skill in the art.

A scent 153 is stored in the inert storage medium 152 shown in the cross-sectional view of FIG. 2A. The scent 153 is preferably heat releasable. In addition, a gas permeable membrane 154 is placed over each recessed three-dimensional region 151. The gas permeable membrane 154 permits scent 153 to escape from the recessed three-dimensional region 151 when heated.

A gas impermeable membrane 155 is shown in ghost view in the cross-sectional view of FIG. 2A. The gas impermeable membrane 155 is used for sealing purposes and is preferably reusable. The gas impermeable membrane 155 prevents the scents 153 stored in recessed three-dimensional region 151 in the multimedia and scent-bearing medium 100 from escaping when the multimedia and scent-bearing medium 100 is not in use.

The multimedia information is stored in the multimedia storage medium 110 of the multimedia and scent-bearing medium 100. The multimedia storage medium 110 in the embodiments depicted in FIGS. 1 and 2A corresponds to the conventional CD-ROM recording format. The multimedia information can also be stored in the multimedia region 110 using other formats, for example, DVD. Utilization of the DVD format will provide for greater storage capacity. The multimedia information stored in the multimedia storage medium 110 may take many forms including, for example, video, audio, textual, graphical, and photographic. As shown in the audio and video embodiment depicted in FIG. 1, audio information is digitally encoded using well known digital encoding formats in the region 113. Video information is also digitally encoded using well-known digital encoding formats in the region 114.

Digital scent identification information and scent recovery sequence information are stored in region 115 of the multimedia storage region 110. The digital scent identification information identifies which scents are stored in which recess three-dimensional regions 151. The scent recovery sequence information is used to synchronize scent recovery with the playback of multimedia information stored in the multimedia region 110. For example, the scent recovery sequence information could be used to recover a gun powder scent to coincide with the canon shot recorded in an audio recording of Tchaikovsky's 1812 Overture. In another embodiment, the scent recovery sequence information could be used to recover flower scents stored in the scent storage region 151.

The multimedia information encoded in the multimedia storage medium 110 preferably may be segregated into separately recoverable segments. This would be particularly useful for use with interactive playback systems (e.g., an interactive multimedia game). Particular scents or particular sequence of scents would be programmed to coincide with particular multimedia segments to give an immersive multi-sensory experience.

Figure 2B:
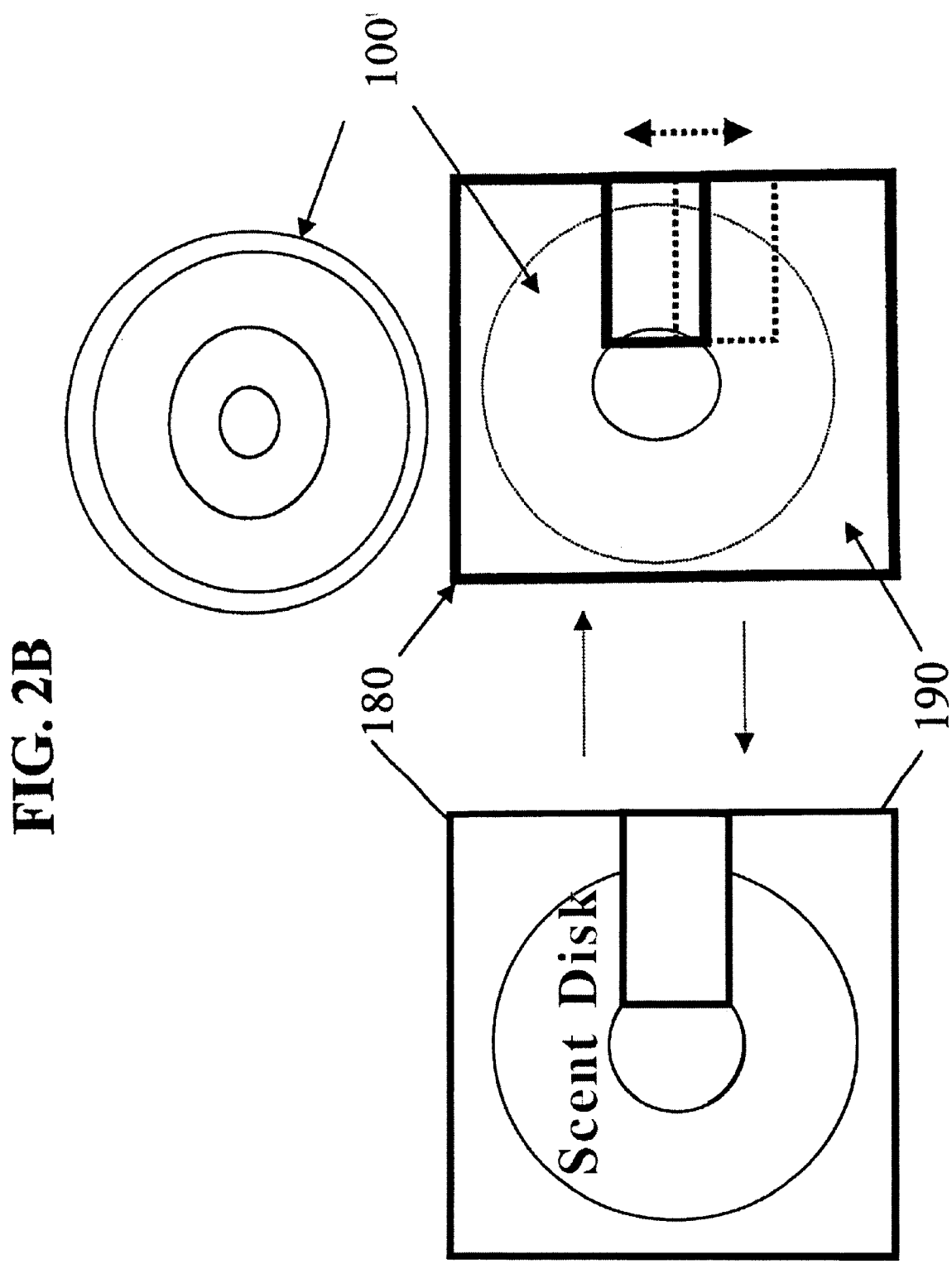
FIG. 2B depicts a multimedia and scent storage medium 100 placed in a storage case 180, and made in accordance with a first alternate embodiment of the present invention.

Preferably a storage case 180 having overlapping seals 190 is used to store the multimedia and scent-bearing medium 100 depicted in FIG. 2B. The overlapping seals 190 prevent scents from escaping from the multimedia and scent-bearing medium 100.

In a variant of the first alternate embodiment shown in FIG. 3, the multimedia and scentbearing medium 100' uses a magnetic memory in place of the optical storage medium depicted in FIGS. 1 and 2A. Information is recovered from magnetic memory electrically. As in the case of the first alternate embodiment, scent is stored in scent-bearing medium 150' in a plurality of recessed three-dimensional regions 151'. In this particular variant the regions take a-rectangular form. The recessed three-dimensional regions 151' are also shown in cross-section in FIG. 3. Also as in the case of the first alternate embodiment, scent 153' is stored in an inert storage medium 152'. The scent 153' is preferably heat releasable. In addition, a gas permeable membrane 154' is placed over each recessed three-dimensional region 151'. The gas permeable membrane 154' permits scent 153' to escape from the recessed three-dimensional region 151' when heated. A gas impermeable membrane 155' is shown in ghost view in the cross-sectional view of FIG. 3. The gas impermeable membrane 155' is used for sealing purposes and is preferably reusable. The gas impermeable membrane 155' prevents the scents 153' stored in recessed three-dimensional region 151' in the multimedia and scent-bearing medium 100' from escaping when the multimedia and scent-bearing medium 100' is not in use.

In another variant of the first alternate embodiment, the multimedia and scent storage medium 100" stores scent in a plurality of scent canisters 260 as depicted in FIG. 4. The scent canisters 260 are stored in a scent storage slot 250. Each canister has a release valve (not shown) of well-understood, conventional construction. Multimedia information is stored in high density, two-dimensional bar codes 110". The two-dimensional bar codes are also used to store scent identification and scent recovery sequence information to control the release of scents from the canisters 260.

The scent storage media and multimedia storage means described herein can be combined in various ways which are also within the scope of this invention. For example, scent canisters can be combined with other optical or magnetic multimedia storage formats.

II. Second Alternate Embodiment

Figure 5:
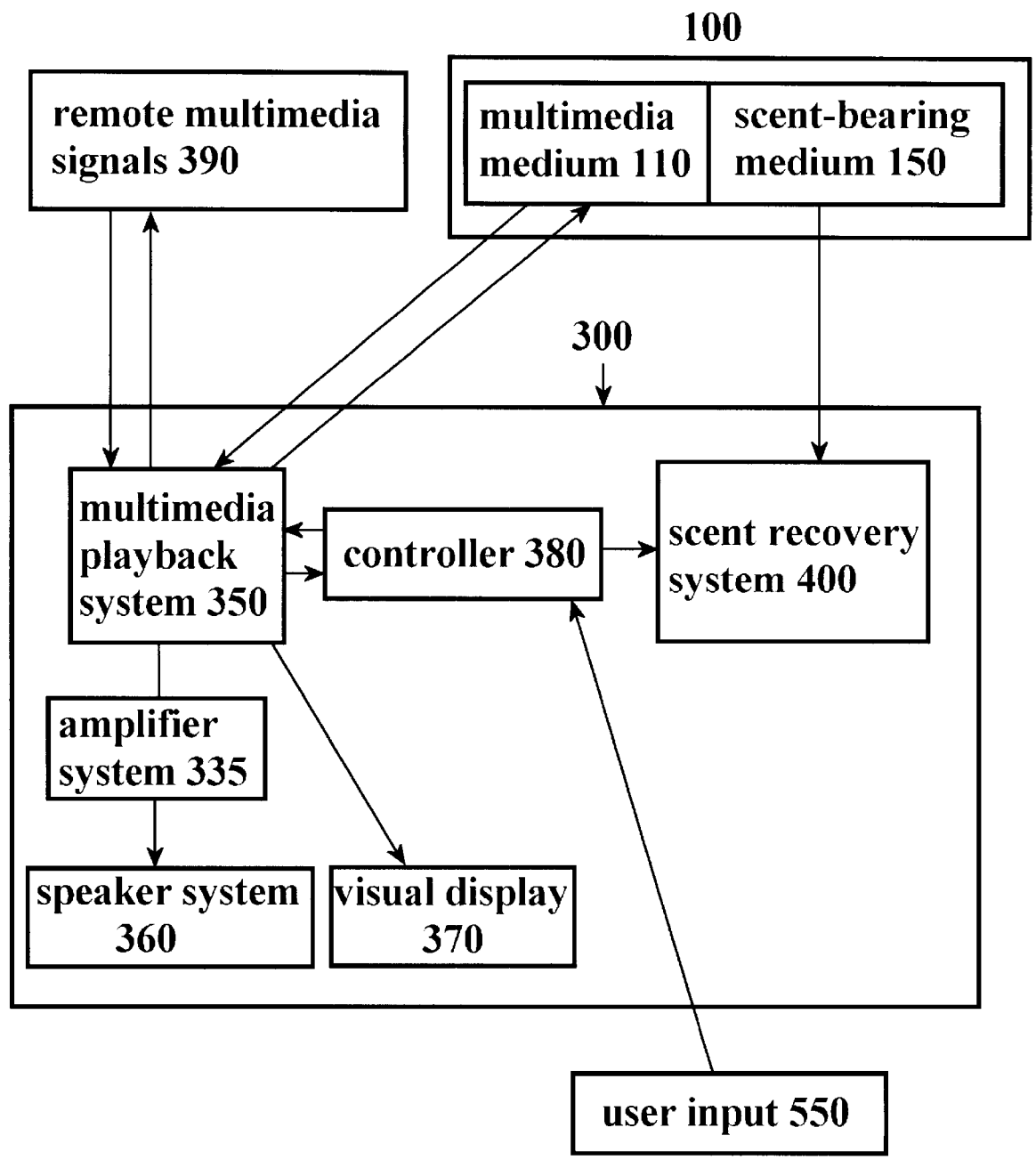
FIG. 5 depicts a conceptual block diagram showing an integrated system having a multimedia and scent storage medium and a multimedia playback and scent recovery system made in accordance with a second alternate embodiment of the present invention.
Figure 6:
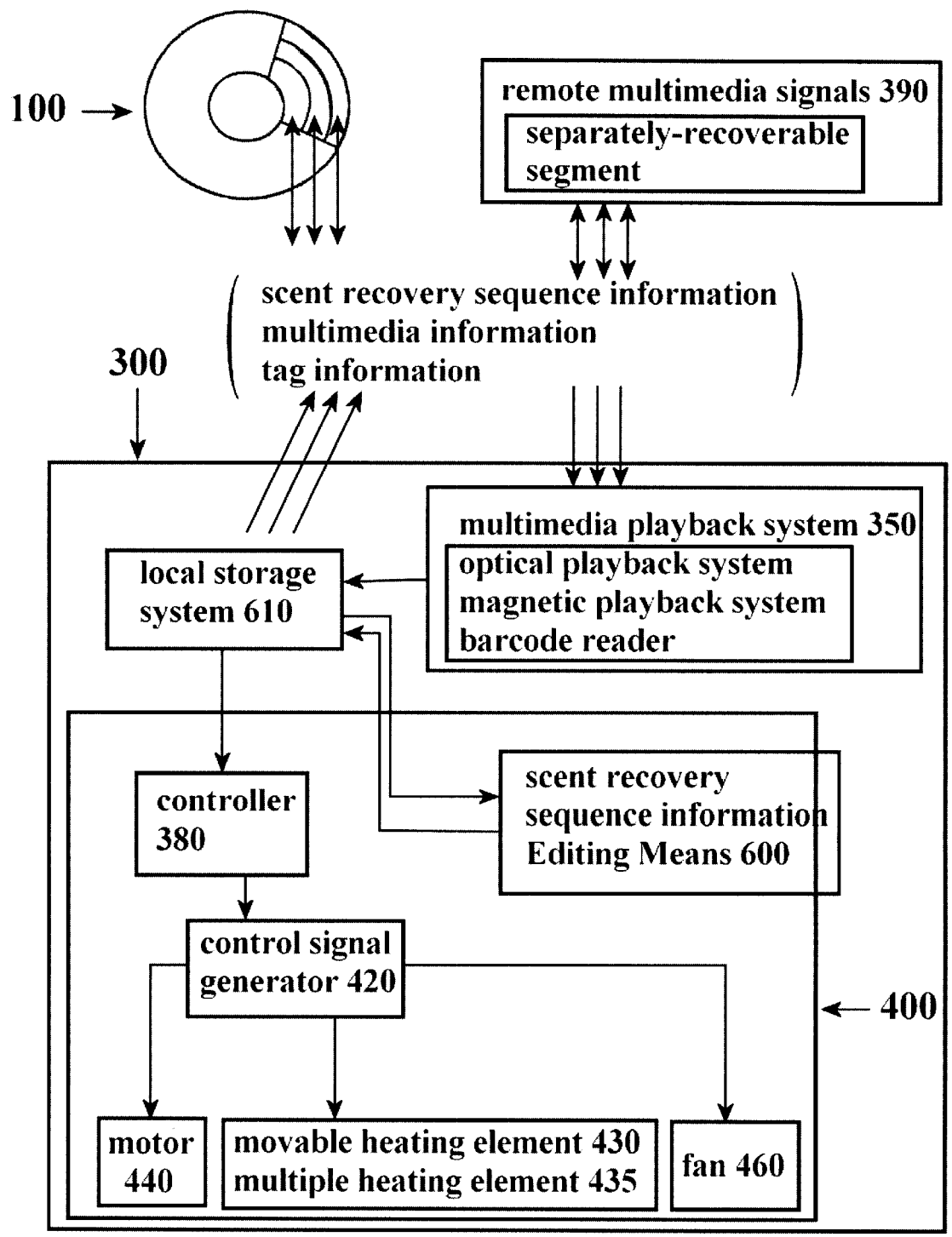
FIG. 6 depicts a conceptual block diagram of a scent recovery system 400 made in accordance with a second alternate embodiment of the present invention.

A second embodiment of the present invention comprises the combination of a multimedia and scent storage medium 100 and an integrated multimedia playback and scent recovery system 300 as shown in conceptual form in FIGS. 5 and 6. As in the case of the first embodiment, the multimedia and scent-bearing medium 100 of the second alternate embodiment comprises a multimedia storage medium 110 and a scent-bearing medium 150. The integrated multimedia playback and scent recovery system 300 comprises a multimedia playback system 350 and a scent recovery system 400. The multimedia playback system 350 recovers multimedia information from the multimedia storage medium 110. The multimedia playback system 350 converts audio information recovered from the multimedia storage medium 110 into an audio signal for amplification by an amplifier system 355 and for playback on a speaker system 360. Video information recovered from the multimedia storage medium 110 is converted into a video signal for playback on a video display 370.

The multimedia playback system 350 also recovers scent identification and scent recovery sequence information from the multimedia storage medium 110. This information is converted into a control signal by controller 380. The control signal generated by controller 380 is used to control the scent recovery system 400. Thus, the multimedia playback system 350 can be used to recover pre-programmed multimedia and scent recovery sequences stored on the multimedia and scent-bearing medium 100. In addition, the multimedia playback system 350 can also be used in conjunction with remote multimedia signals 390 which may be recovered from various sources, e.g., radio/broadcasting, satellite, Internet, a public switched telephone network (PSTN), a LAN, a WAN or a computer. These remote multimedia signals 390 may also include scent recovery sequence information. Thus, scents stored in the multimedia and scent-bearing medium 100 can be used in the second alternate embodiment either with multimedia signals stored in the multimedia and scent-bearing medium 100 or with remote multimedia signals 390 captured from a plurality of sources.

Figure 7:
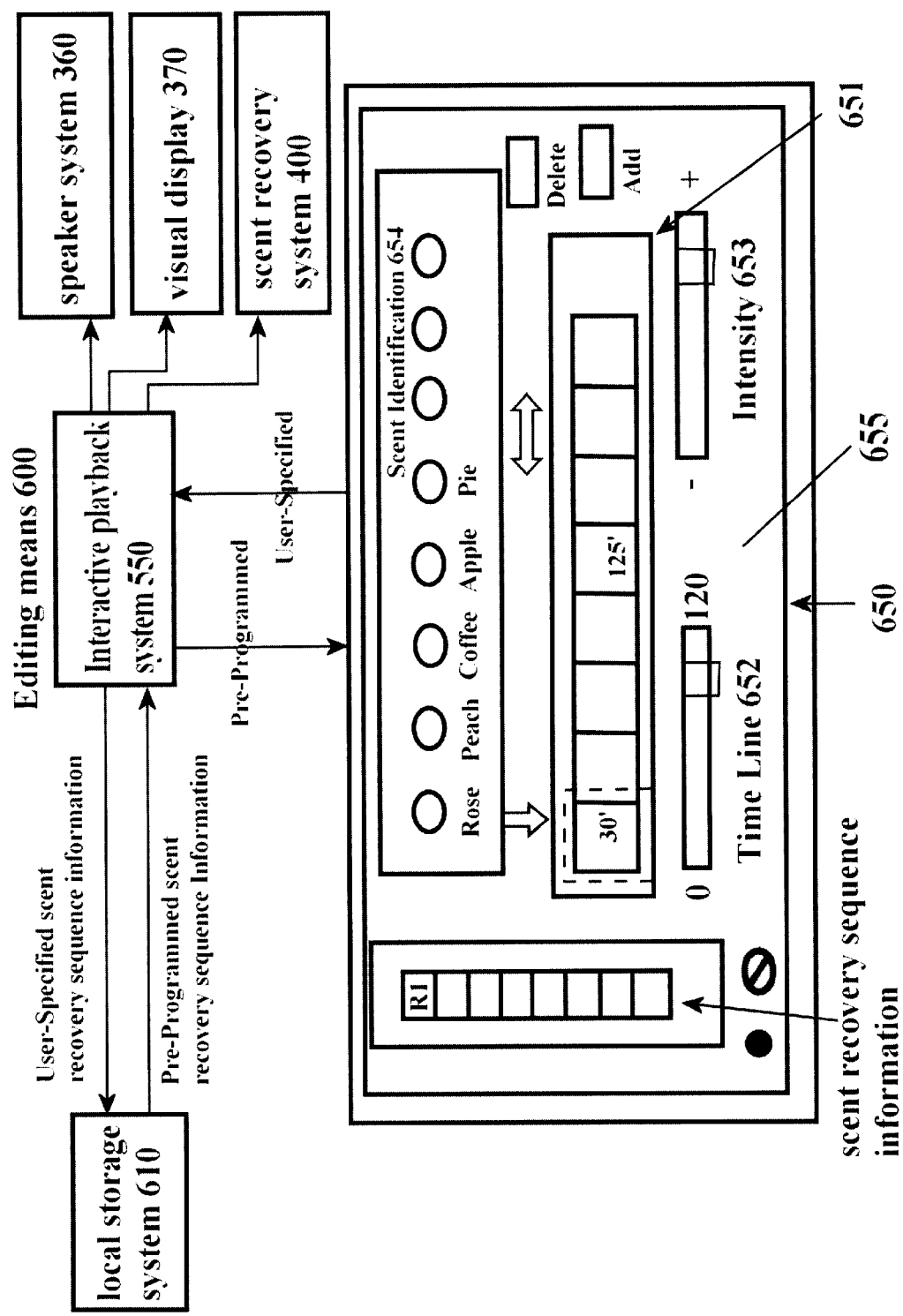
FIG. 7 depicts a conceptual block diagram and graphical user interface illustrating the operation of editing means 600 and graphical user interface 650, and made in accordance with a second alternate embodiment of the present invention.

The multimedia playback and scent recovery system 300 has several playback modes. For example, a user could simply "play back" preprogrammed multimedia and synchronized scent recovery sequences by depressing a start button to initiate the sequence. The multimedia playback and scent recovery system 300 also facilitates other playback modes. For example, the multimedia playback and scent recovery system 300 also includes as part of the interactive playback system 550 an editing means 600 as shown in FIGS. 6 and 7 for "customizing" pre-programmed multimedia and scent recovery sequences to accommodate user preferences. The editing means 600 comprises a local storage system 610 for storing the scent recovery sequence information recovered either from the multimedia and scent-bearing 100 or the remote source 390. Many types of local storage systems 610 may be used to store multimedia information, for example, a mini hard drive, a RAM, or a MP3.

The editing means 600 also comprises a graphical user interface 650 which is depicted in FIG. 7 and which may be displayed on the display system of the multimedia playback and scent recovery system 300. The graphical user interface 650 as depicted in FIG. 7 may take many forms within the scope of this invention. For example, the graphical user interface 650 may include a portion 651 that depicts in graphical form the multimedia segments for which scent recovery sequence information is created. The scent recovery sequence information will be edited on a multimedia segment by segment basis. The user would double click on which multimedia portion indicated in 651 he/she wishes to edit the pre-programmed scent recovery sequence information. Once the user has indicated the multimedia segment of interest, the editing means 600 will recall the scent recovery sequence information corresponding to the segment from memory and display it in region 651. The display in region 651 will comprise a combination of timeline 652, intensity 653 and scent identification information 654. The timeline 652 will indicate which scents will be recovered in what sequence, and for what duration. The intensity segment 653 effectively specifies the amount of heat that will be applied to the scent-bearing regions 151 of the multimedia and scent-bearing medium 100.

A Java platform, particularly its Abstract Windowing Toolkit (AWI) can be used to create custom graphical front ends 655 for display on the graphical user interface 650. The AWT provides interfaces and classes for dealing with different types of events generated by AWT components. In addition, Java gives application programmers numerous tools for building professional, customizable cross-platform GUTs (graphic user interfaces).

Alternatively, the graphical user interface 650 can be created using a "Windows" platform. The coded Application Interface (API) can be used to create custom graphical front ends. Some C++ applications already provide interfaces and classes for dealing with different types of events generated by API components.

The editing means 600 through the graphical user interface 650 permits a user to add scents, delete scents, overlap scents, increase the duration of scents, and decrease the duration of scents. Further, the editing means 600 permits a user to create an entirely new scent recovery sequence for use with multimedia segments.

Figure 8:
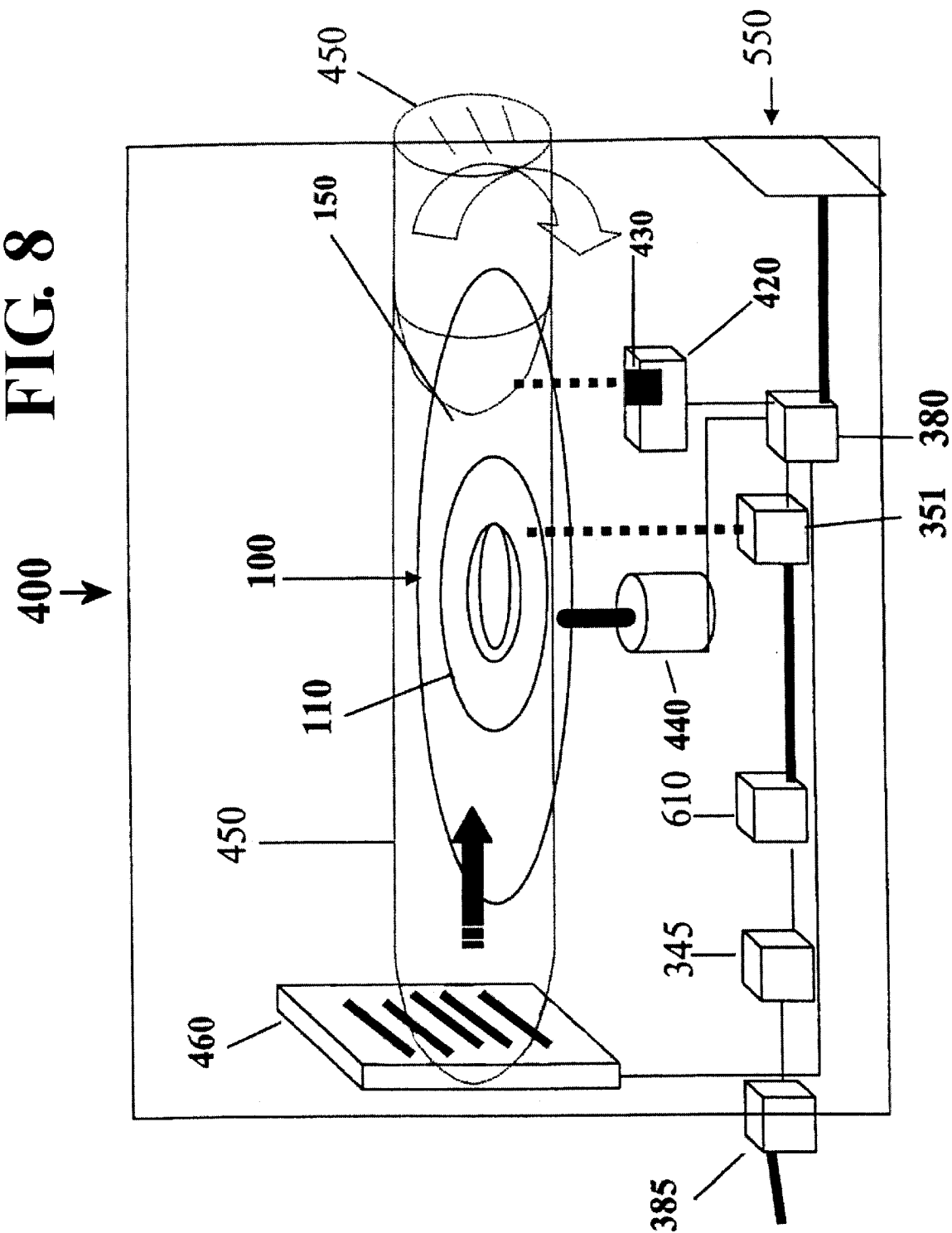
FIG. 8 depicts a schematic cross-sectional side view of a scent recovery system 400 made in accordance with a second alternate embodiment of the present invention for use in combination with multimedia and scent-bearing medium 100.

A cross-sectional side view of a scent recovery system 400 made in accordance with a second alternate embodiment of the present invention is illustrated in FIG. 8. The scent recovery system 400 includes a movable heating element 430 (e.g. an Infrared or laser) which operates in response to control signals provided by the control signal generator 420 (e.g. Motorola's 8000 senes microprocessor). After recovery of the scent recovery sequence information, tag information, and multimedia information from the multimedia storage medium 110 to the local storage system 610, the controller 380 (e.g. CMOS PlC microcontroller) can use the tag information as reference data to couple event-related scent recovery signals which either have been transmitted from a remote multimedia source 390 or from the multimedia storage medium 110 to emit predetermined scent or combination of scents from the scent disk 100 by a ductwork 450 and controlled fan 460 (e.g. heat sink fan). A replaceable scent disk 100 emits a predetermined scent or a combination of scents when heated. Preferably, a predetermined scent from a scent-bearing medium 150 from the scent disk 100 is positioned directly above and/or in front of the movable heating element 430 by a controlled motor 440 (e.g. bipolar stepper motor).

Figure 9:
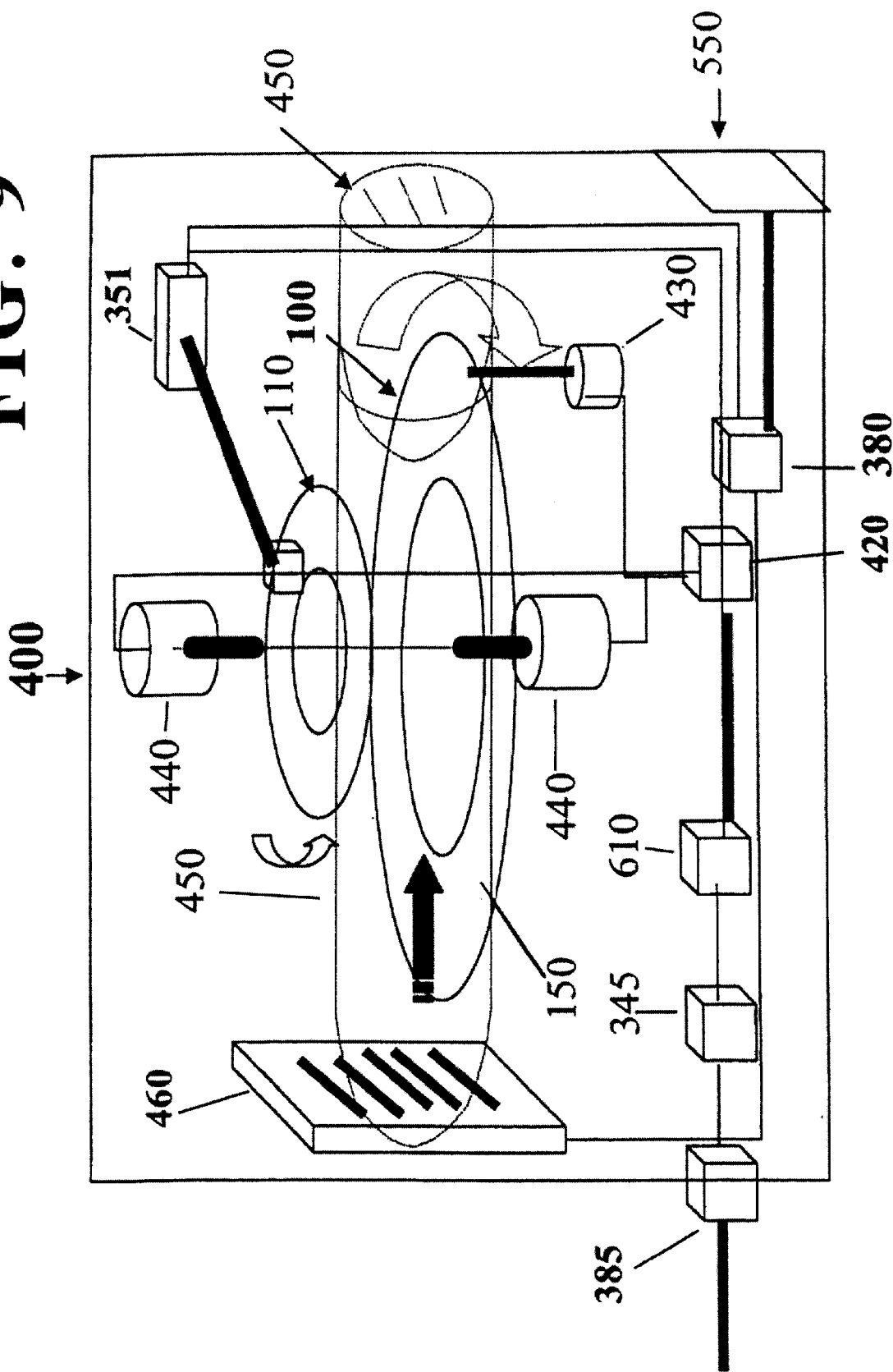
FIG. 9 depicts a schematic cross-sectional side view of an alternate scent recovery system 400 made in accordance with a second alternate embodiment of the present invention for use in combination with an alternate multimedia and scent-bearing medium 100.

In another variant of the second alternate embodiment of this invention shown in FIG. 9, a separable multimedia storage medium 110 (e.g. a compact disc) from scent-bearing medium 150 can actually operate as a separate entity by separate selectively controlled motor 440 without interruption to either unit.

Figure 10:
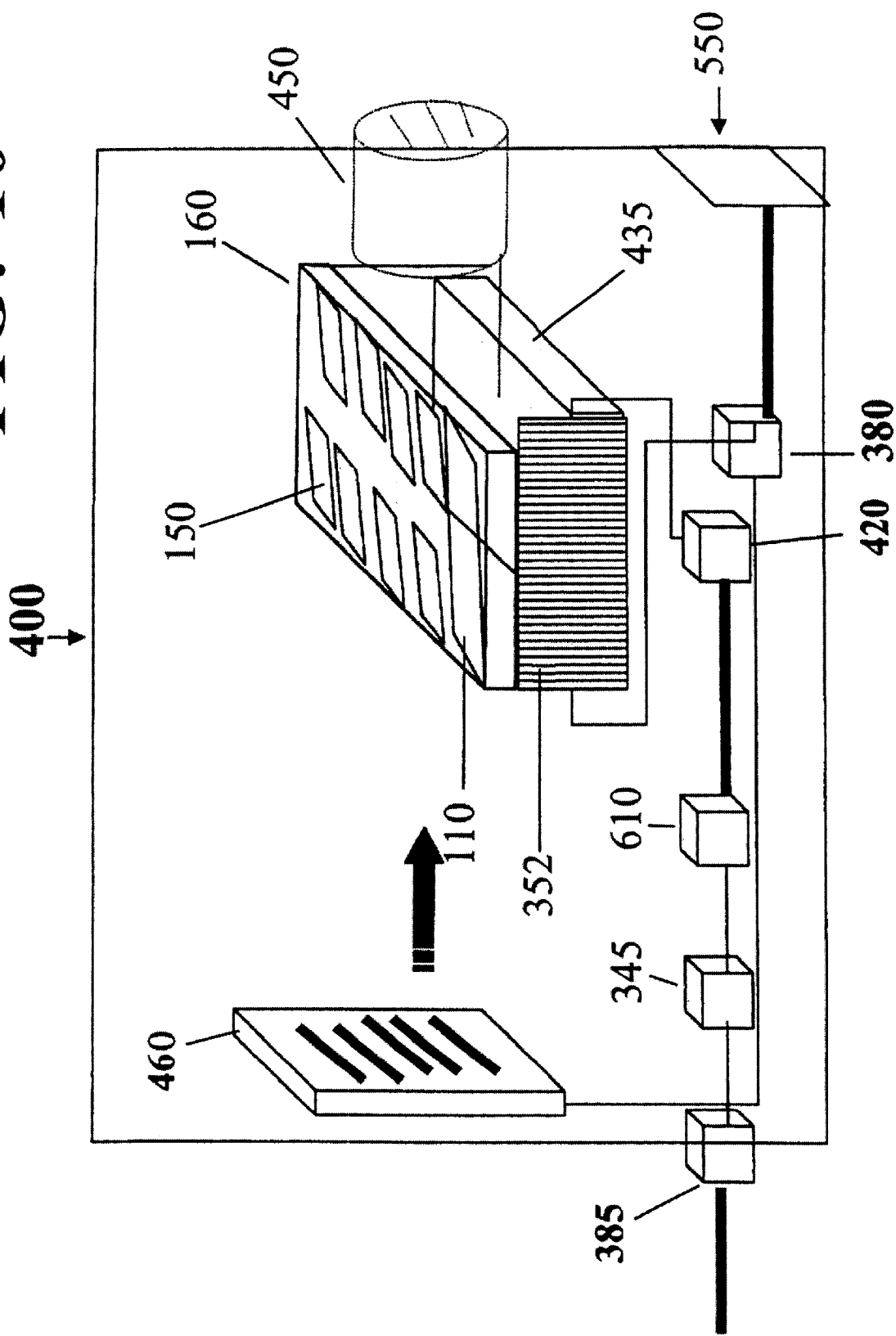
FIG. 10 depicts a schematic cross-sectional side view of an alternate scent recovery system 400 made in accordance with a second alternate embodiment of the present invention for use in combination with an alternate multimedia and scent-bearing medium 100.

Yet another cross-sectional side view of a scent recovery system 400 made in accordance with the second alternate embodiment of the present invention is illustrated in FIG. 10. The scent recovery system 400 includes a multiple heating element 435 (e.g. an infrared or laser heating coil) which operates in response to control signals provided by the control signal generator 420. The insertable scent card 160 electronically connects with the controller 380 through a connector type magnetic playback system 352. After recovery of the scent recovery sequence information, tag information, and multimedia information from the multimedia storage medium 110 to the local storage system 610, the controller 380 can use the tag information as reference data to couple event-related scent recovery signals which either have been transmitted from a Note multimedia source 390 or from the multimedia storage medium 110 to emit predetermined scent or combination of scents from the scent card 160 by a ductwork 450 and controlled fan 460. A replaceable scent card 160 emits a predetermined scent or combination scents of scents When heated. Preferably, a predetermined scent from a scent-bearing medium 150 from the scent card 160 is positioned directly above and/or in front of the multiple heating element 435 by selective control signals.

Figure 11:
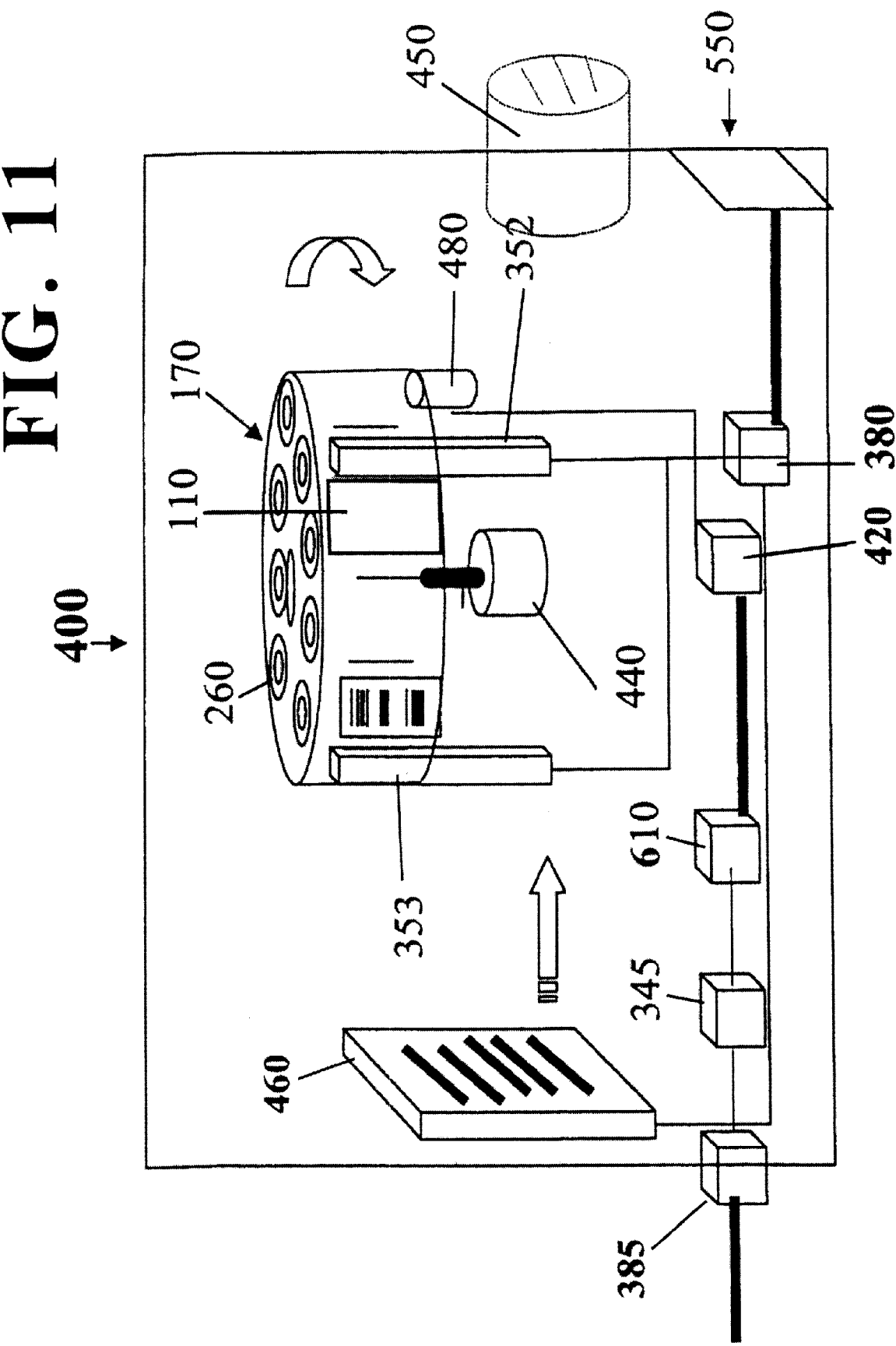
FIG. 11 depicts a schematic cross-sectional side view of an alternate scent recovery system 400 made in accordance with a second alternate embodiment of the present invention for use in combination with an alternate multimedia and scent-bearing medium 100.

A cross-sectional side view of a scent recovery system 400 made in accordance with the second alternate embodiment of the present invention is illustrated in FIG. 11. The scent recovery system 400 includes a selectively controlled release valve system 480 (e.g. an ink-jet system) which operates in response to control signals provided by the control signal generator 420. After a barcode reader 353 or magnetic playback system 352 has retrieved the scent recovery sequence information, tag information, and multimedia information from the scent identification 120 or multimedia storage medium 110 into the local storage system 610, the controller 380 then CD use the tag information as reference data to couple event-related scent recovery signals which either have been transmitted from a remote multimedia source 390 or recovered from the multimedia storage medium 110 to emit predetermined scent or combination of scents from the cartridge 170 using a ductwork 450 and controlled fan 460. The replaceable scent cartridge 170 emits a predetermined scent or a combination of scents when activated. Preferably, a predetermined scent canister 260 from the scent cartridge 170 is positioned directly in front of the ductwork 450 and controlled fan 460 by a controlled motor 440.

Figure 13:
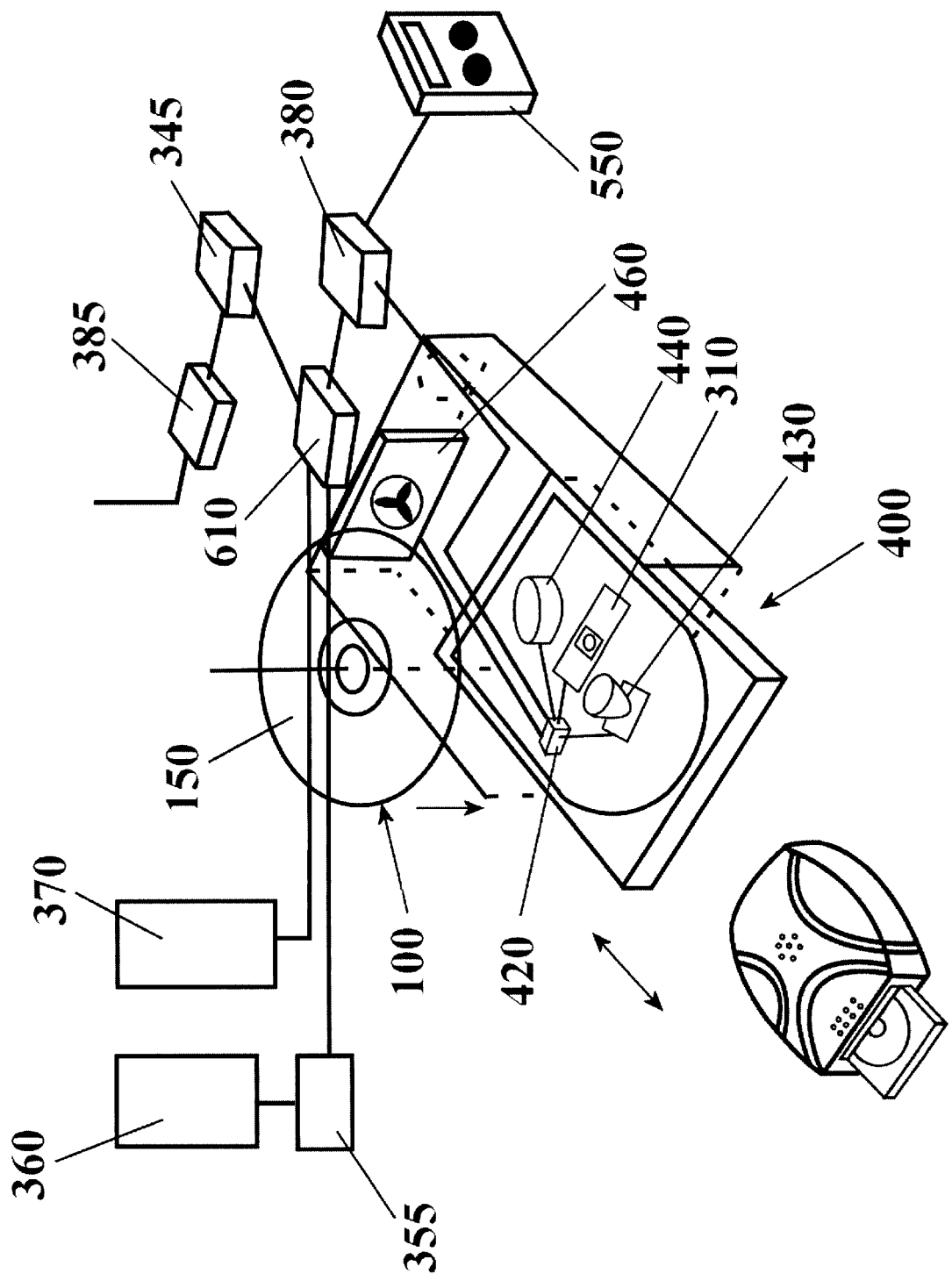
FIG. 13 depicts an exploded view of an alternate multimedia playback and scent recovery system made in accordance with a second alternate embodiment of the present invention for use in combination with an alternate multimedia and scent-bearing medium 100.

Another multimedia playback and scent recovery system made in accordance with the second alternate embodiment of the present invention is illustrated in FIG. 13, wherein, the multimedia playback system 350 is separable from the scent recovery system 400.

Figure 12:
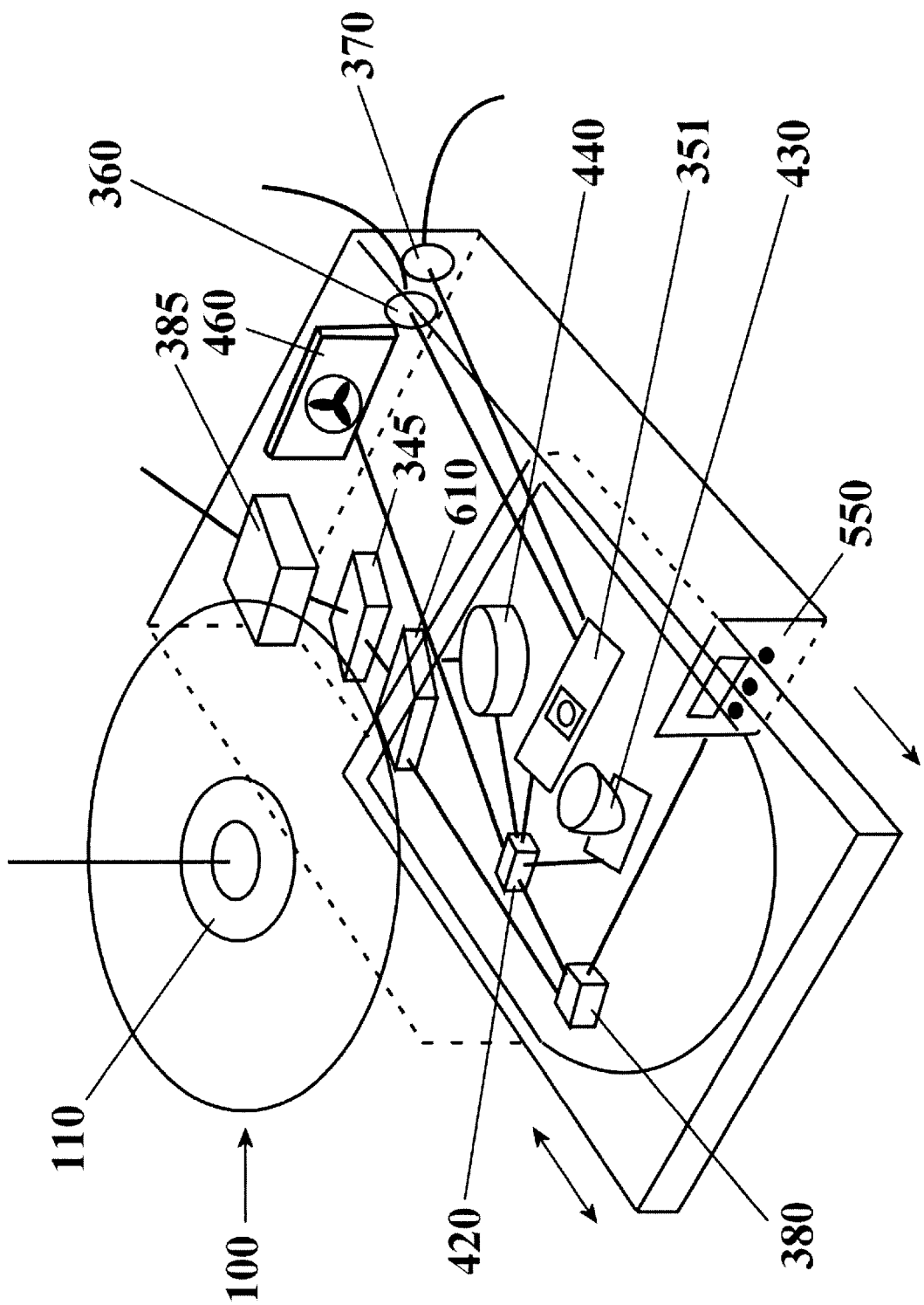
FIG. 12 depicts an exploded view of a multimedia playback and scent recovery system made in accordance with a second alternate embodiment of the present invention for use in combination with a multimedia and scent-bearing medium 100.

A multimedia playback and scent recovery system made in accordance with the second alternate embodiment of the present invention is illustrated in FIG. 12. In this embodiment, the playback system comprises a scent disk 100 having not only a :scentbearing mediun 150 but also a multimedia storage medium 110 (e.g. a compact disc), with scent recovery sequence information, tag information, and multimedia information encoded thereon. A multimedia playback system 350 including an optical playback system 351 serves as the recovery system for accessing and processing the scent recovery sequence information, tag information, and multimedia information stored on the multimedia storage medium 110. The optical playback system 351 transmits scent recovery sequence information, tag information, and multimedia information to the controller 380 which encodes scent recovery sequence information into electronic signals prior to transmitting to the scent recovery system 400 or to a local storage system 610. A control signal generator 420 then retrieves the electronic signals to the scent recovery system 400.

Figure 14:
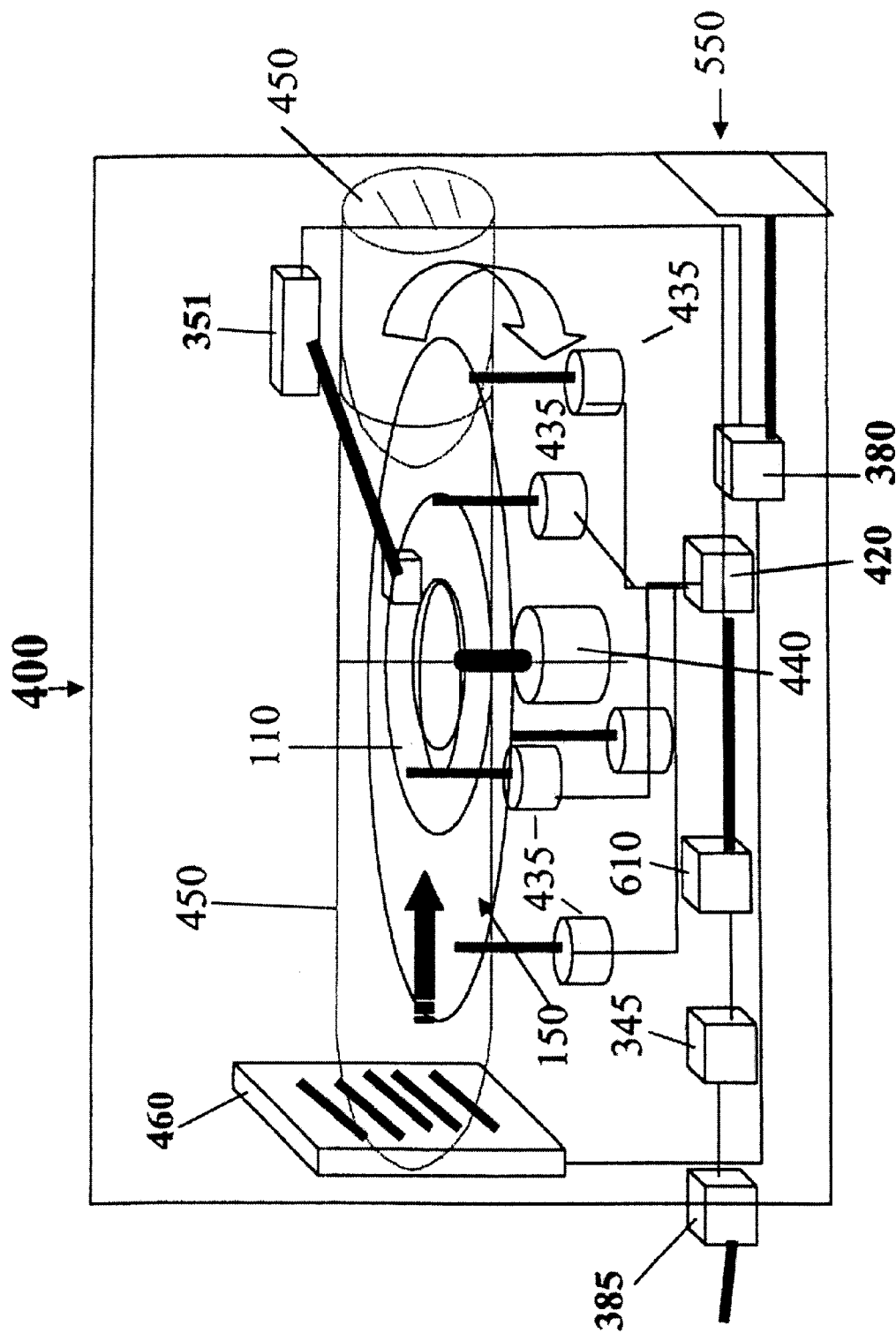
FIG. 14 depicts a schematic cross-sectional side view of an alternate scent recovery system 400 made in accordance with a second alternate embodiment of the present invention for use in combination with an alternate multimedia and scent-bearing medium 100.

A cross-sectional side view of a scent recovery system 400 made in accordance with the second alternate embodiment of the present invention is illustrated in FIG. 14. The scent recovery system 400 includes a multiple heating element 435 (e.g. an Infrared or laser heating coil) which operates in response to control signals provided by the control signal generator 420. After recovery of the scent recovery sequence information, the information, and multimedia information from the multimedia storage medium 110 to the local storage system 610, the controller 380 can use the tag information as reference data to couple event-related scent recovery signals which either have been transmitted from a remote multimedia source 390 or from the multimedia storage medium 110 to emit predetermined scent or combination of scents from the scent disk 100 by a ductwork 450 and controlled fan 460. A replaceable scent disk 100 emits a predetermined scent or combination of scents when heated. Preferably, a plurality of predetermined scents from a scent-bearing medium 150 from the scent disk 100 are positioned directly above and/or in front of the multiple heating element 435 by selective control signals.

Figure 15:
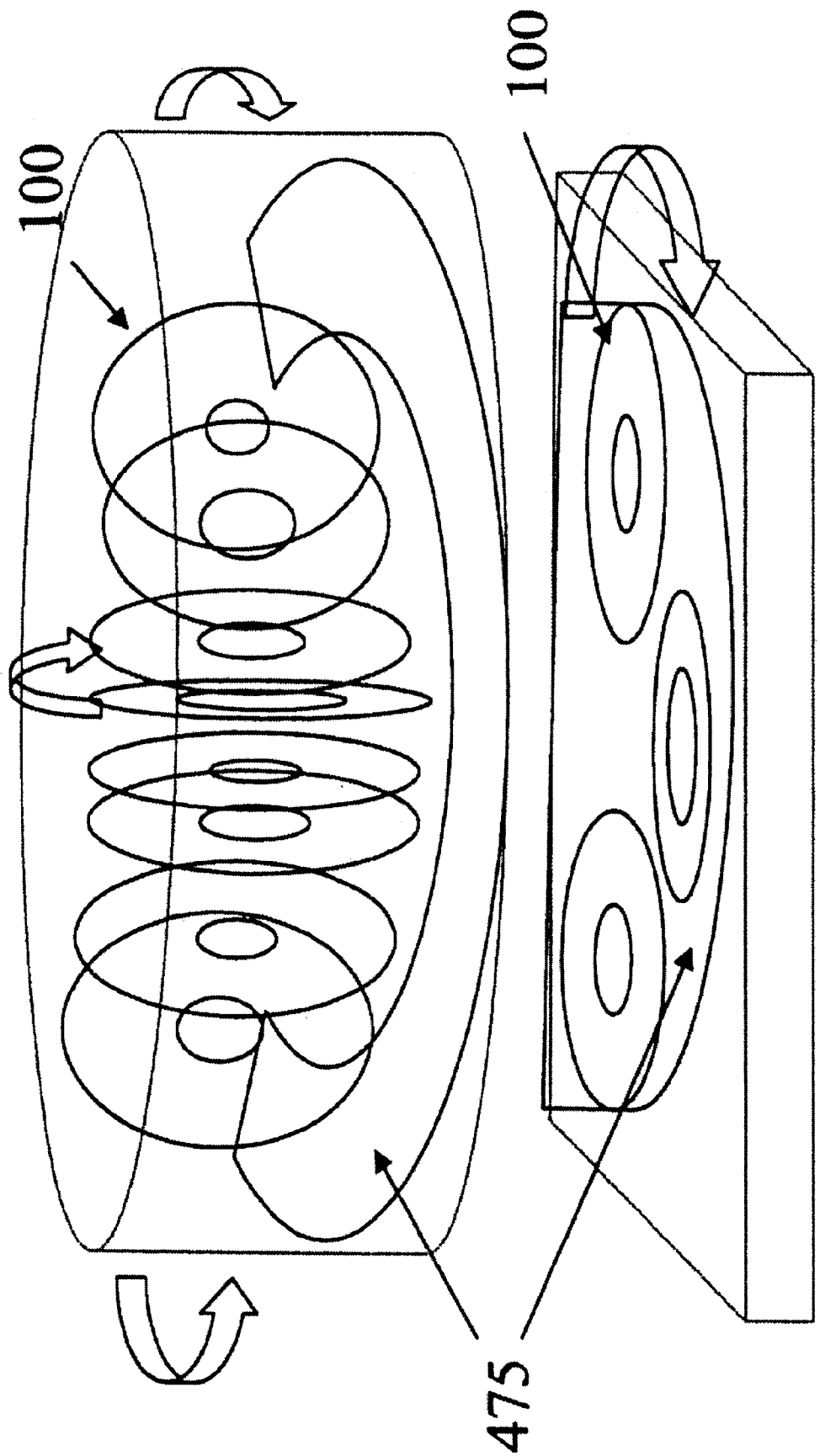
FIG. 15 depicts a cross-sectional view of an alternate multimedia playback and scent recovery system made in accordance with a second alternate embodiment of the present invention for use in combination with an alternate multimedia and scent-bearing medium 100.

Another embodiment of this invention is depicted in FIG. 15, and shares the advantage of having scent recovery sequence information and multimedia information encoded therein. In this version of a multimedia playback and scent recovery system made according to the second alternate embodiment of the present invention, multiple scent disks 100 having this advantage are loaded in disk-like slots 475 within the jukebox-like embodiment.

Figure 16:
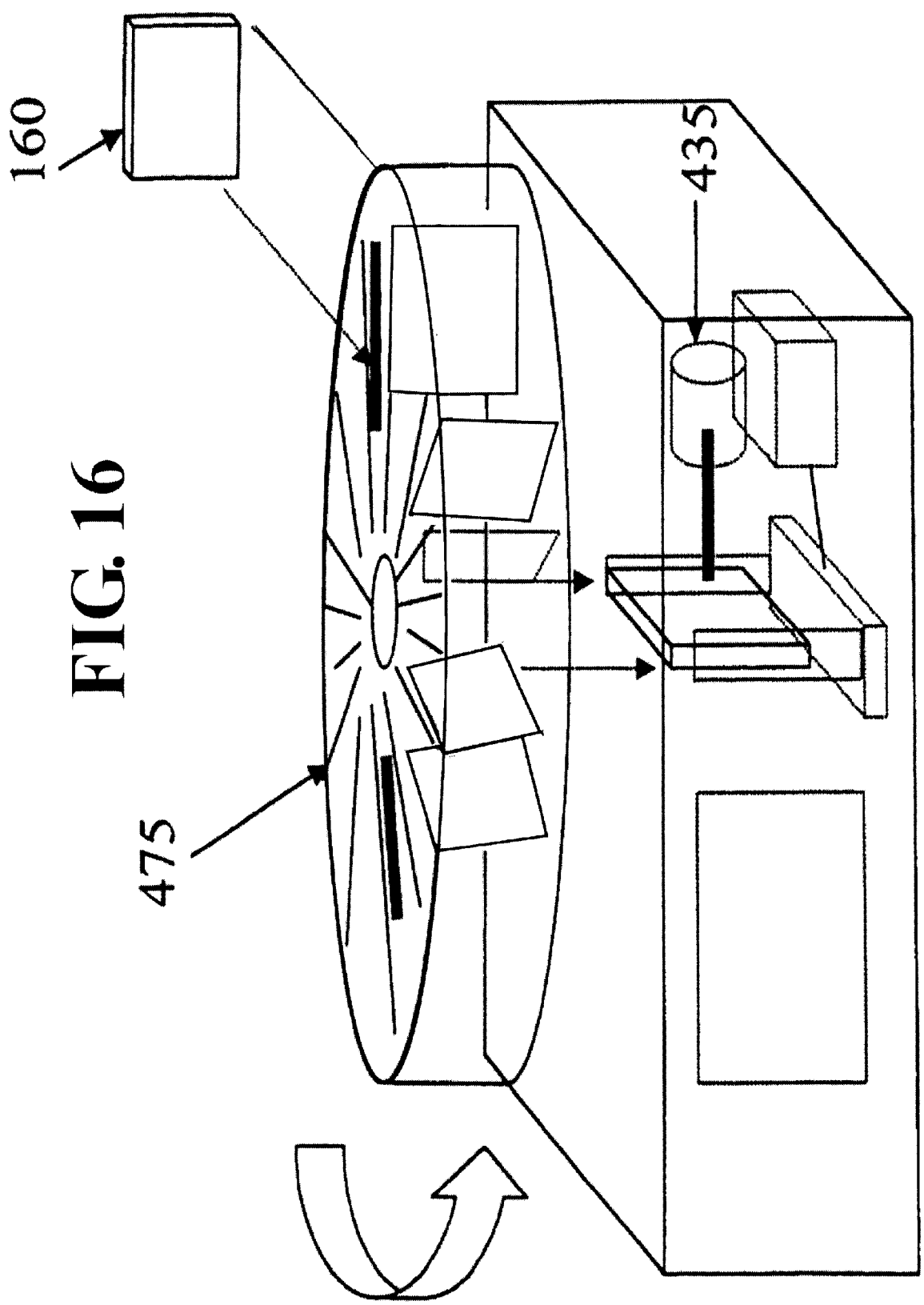
FIG. 16 depicts a cross-sectional view of an alternate multimedia playback and scent recovery system made in accordance with a second alternate embodiment of the present invention for use in combination with an alternate multimedia and scent-bearing medium 100.

Another embodiment of this invention shown in FIG. 16, with the advantage of the scent recovery sequence information and multimedia information therein, illustrates another version of a multimedia playback and scent recovery system according to the second alternate embodiment of the present invention by loading multiple scent cards 160 on card-like slots 475 within a slide projector-like embodiment.

In operation, the multimedia playback system 350 recovers at least the tag information and a portion of the scent recovery sequence and multimedia information encoded on the multimedia storage medium 110 or from a remote multimedia source 390 through the input connection 385. The multimedia playback system 350 then transmits electronic signals to the controller 380 to generate scent control signals coupled with the tag information from the multimedia storage medium 110. Upon receipt of the control signals from the control signal generator 420, the controlled motor 440 turns the scent disk 100, and both the movable heating element 430, and the controlled fan 460 are activated, thereby releasing the desired scent or combination of scents. The movable heating element 430 and the controlled fan 460 may be activated for an identical period of time, or for different lengths of time to release different strengths of their respective scents. In addition, the movable heating element 430 (e.g. infrared or laser) only targets heat-releasable scents 230 within the inert storage medium 152 on the scent disk 100. The inert storage medium 152 will not interfere with the heat absorption process. Each of the systems in the scent recovery system 400 is deactivated in response to control signals transmitted by the control signal generator 420 to prevent any further scent release. When deactivated, the controlled motor 440, the movable heating element 430, and the controlled fan 460 are turned off. This process is repeated, as necessary, according to the scent recovery sequence and multimedia information encoded on the multimedia storage medium 110.

III. Third Alternate Embodiment

Figure 17:
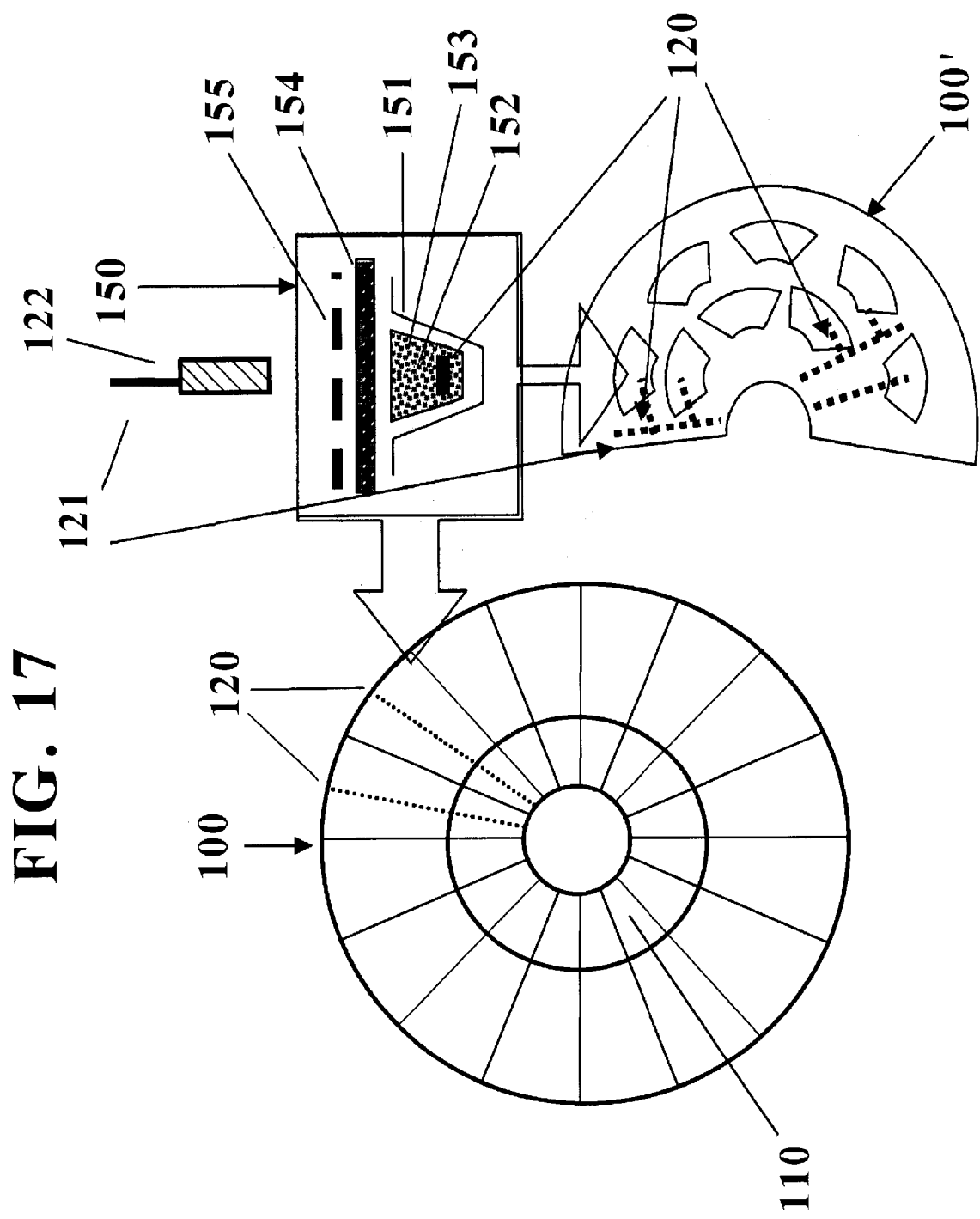
FIG. 17 depicts a top and side cross-sectional view of a multimedia and scent-bearing medium 100 made in accordance with a third alternate embodiment of the present invention.

A third alternate embodiment of the present invention comprises a multimedia and scent-bearing medium 100 as depicted in FIG. 17. The multimedia and scent-bearing medium 100 comprises three elements: a multimedia storage medium 110, a scent-bearing medium 150, and an electrostatic scent release means 120, 121. The scent-bearing medium 150 further comprises a plurality of recessed three-dimensional regions 151 each for storing a separate scent.

Deposited within each three-dimensional region is an inert storage medium 152. The inert storage medium 152 is not reactive with the scents that will be stored within it. The three-dimensional region is formed in the plastic housing of the multimedia and scent-bearing medium 100. A plurality of radially extending three-dimensional regions are shown in the multimedia and scent-bearing medium 100 depicted in FIG. 17. The three-dimensional regions may also take concentric forms 151' as shown in the partial alternate view of the multimedia and scentbearing medium 100' also shown in FIG. 17. The inert storage medium 152 may be a liquid or a polymer gel and may take other forms that are well known to those of ordinary skill in the art.

A scent 153 is stored in the inert storage medium 152 shown in the cross-sectional view of FIG. 17. The scent 153 is preferably electrostatically releasable. The electrostatic scent release means comprises an electrode 120 and associated control circuitry 121. The electrode 120 shown in FIG. 17 is intended to operate in conjunction with an electrode 122 of a separate multimedia playback and scent recovery system. The separate multimedia playback and scent recovery system will impart a potential difference between the electrode 120 and the electrode of the multimedia playback and scent recovery system 122 to electrostatically release scent stored in recessed three-dimensional region 151.

In this variant the electrostatic scent release means operates according to a corona discharge principle. The electrode 120 positioned within the recessed three-dimensional region comprises a corona electrode 120, and the electrode 122 positioned above the recessed three-dimensional region comprises a counter electrode 122. A separate multimedia playback and scent recovery system would impart a potential difference between the counter electrode 122 and corona electrode 120 of sufficient magnitude (e.g., of 1–20 kilovolts) to sustain a corona discharge. The corona discharge would impart a charge to scent molecules, thereby aiding in their vaporization. Once vaporized, the scent molecules would be attracted to the counter electrode.

In further variants, the multimedia and scent bearing medium will have a plurality of recessed three-dimensional regions, each having at least one electrode. Further variants of the third alternate embodiment will comprise a plurality of recessed three-dimensional regions, wherein each of the regions have a pair of electrodes and associated control circuitry. In variants wherein each recessed region has a pair of electrodes, the separate multimedia playback and scent recovery system need not have a separate electrode, but need merely be capable of imparting a potential difference between the electrodes associated with each of the recessed three-dimensional regions through the associated control circuitry to accomplish scent release.

In addition, a gas permeable membrane 154 is placed over each recessed three-dimensional region 151. The gas permeable membrane 154 permits scent 153 to escape from the recessed three-dimensional region 151 when electrostatically released.

A still further variant of the third embodiment depicted in FIG. 17 comprises a scent bearing medium which further comprises a scent storage region; scent identification means for identifying scents stored in the scent bearing medium; and an electrostatic scent release means for releasing scent from the scent-bearing medium. In contrast to the multimedia and scent-bearing medium depicted in FIG. 17, this variant does not have a multimedia region 110, but can be used with multimedia information recovered from other sources (e.g., the Internet, CDs or DVDs) to create a virtual reality experience having audio, visual and scent stimulation. The scent identification means comprises scent identification information that can be used to sequence scent recovery to coincide with the multimedia information recovered from the remote source. The scent identification means further comprises scent recovery sequence information for use in controlling the sequence of scent recovery from the scent-bearing medium.

Figure 18:
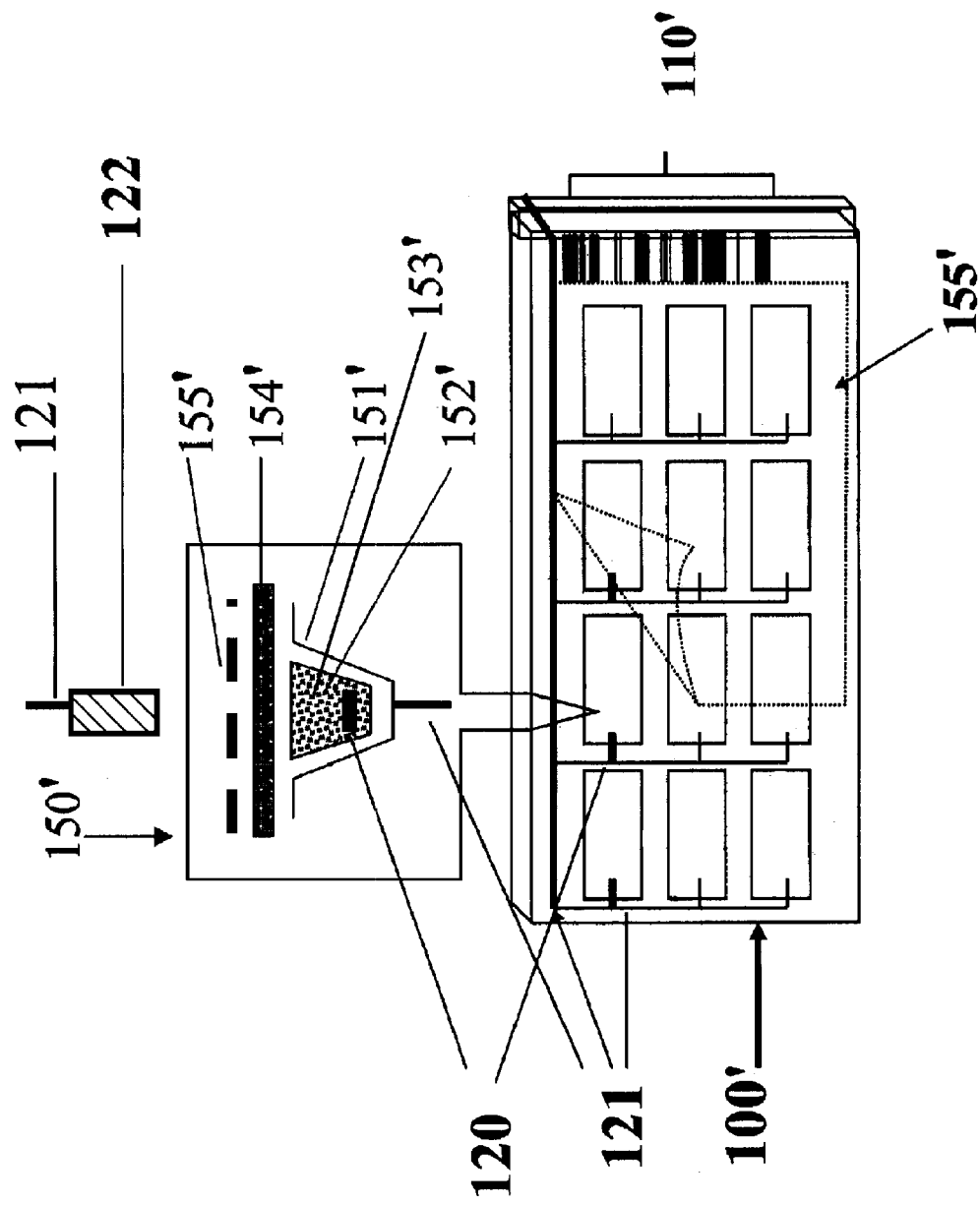
FIG. 18 depicts a top and side cross-sectional view of a multimedia and scent-bearing medium 100 made in accordance with a third alternate embodiment of the present invention.

In a variant of the third alternate embodiment shown in FIG. 18, the multimedia and scent-bearing medium 100' uses a magnetic memory in place of the optical storage medium depicted in FIG. 17. Information is recovered from magnetic memory electrically. As in the case of the third alternate embodiment, scent is stored in scent-bearing medium 150 in a plurality of recessed three-dimensional regions 151'. In this particular variant the regions take a rectangular form. The recessed three-dimensional regions 151' are also shown in cross-section in FIG. 18. Also as in the case of the third alternate embodiment, scent 153' is stored in an inert storage medium 152'. The scent 153' is preferably electrostatically releasable. The electrostatic scent release means comprises an electrode 120 and associated control circuitry 121. The electrode 120 shown in FIG. 18 is intended to operate in conjunction with an electrode 122 of a separate multimedia playback and scent recovery system, although other arrangements are possible as described in conjunction with FIG. 17. In addition, a gas permeable membrane 154' is placed over each recessed three-dimensional region 151'. The gas permeable membrane 154' permits scent 153' to escape from the recessed three-dimensional region 151' when heated. A gas impermeable membrane 155' is shown in ghost view in the cross-sectional view of FIG. 18. The gas impermeable membrane 155' is used for sealing purposes and is preferably reusable. The gas impermeable membrane 155' prevents the scents 153' stored in recessed three-dimensional region 151' in the multimedia and scent-bearing medium 100' from escaping when the multimedia and scent-bearing medium 100' is not in use.

Figure 19:
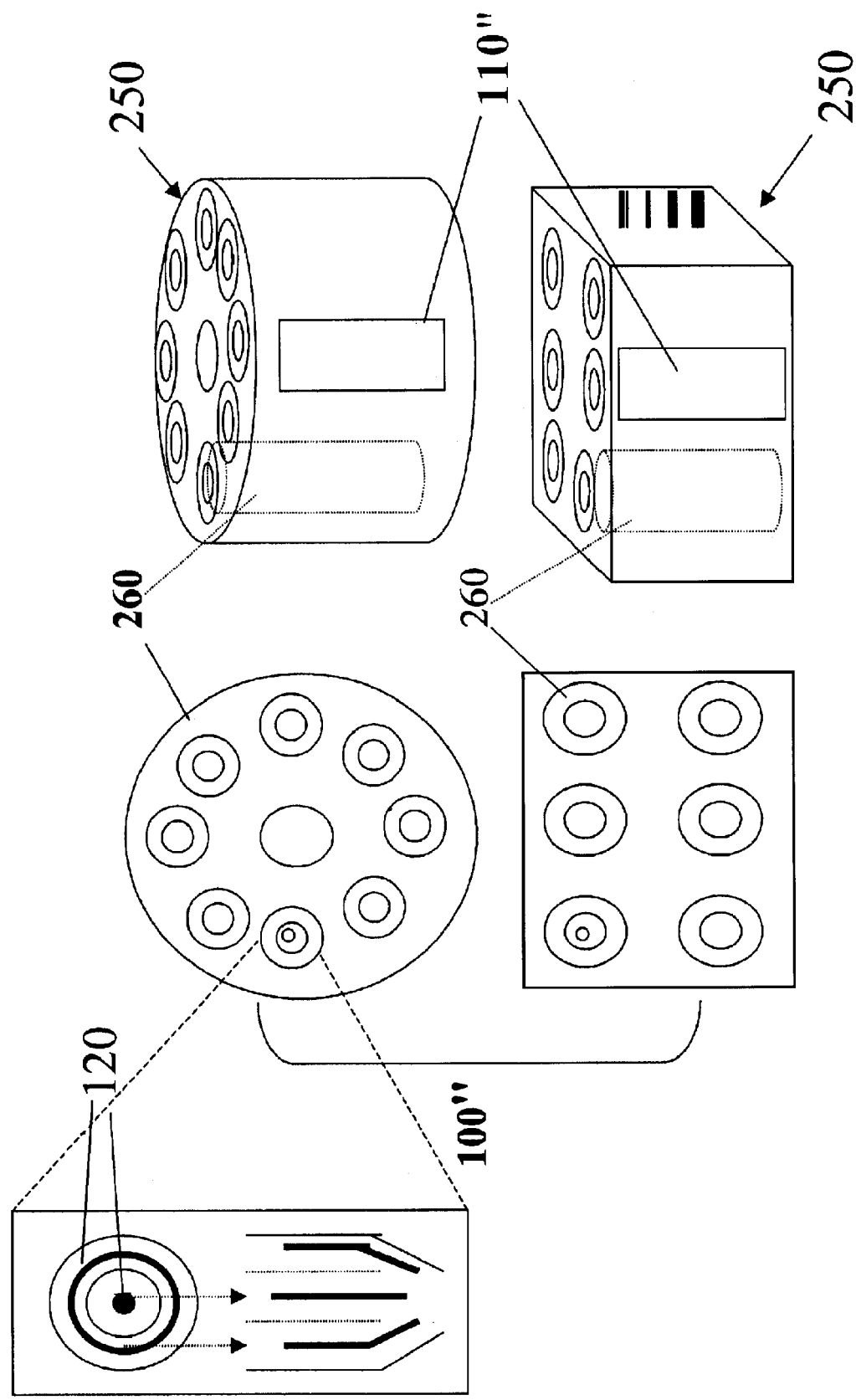
FIG. 19 depicts a top and side cross-sectional view of a multimedia and scent-bearing medium 100 made in accordance with a third alternate embodiment of the present invention.

In another variant of the third alternate embodiment depicted in FIG. 19, the multi-media and scent-storage medium 100' stores scent in a plurality of scent canisters 260. The scent canisters 260 are stored in a scent storage slots 250. Each canister has a release valve (not shown) of well-understood, conventional construction. Multimedia information is stored in high density, two-dimensional bar codes, like Symbol Technologies, Inc.'s PDF417, or other even higher-density two-dimensional bar codes known to those skilled in the art. The two-dimensional bar codes are also used to store scent identification and scent recovery sequence information to control the release of scents from the canisters 260. The electrostatic scent release means comprises electrodes 120 and associated control circuitry (not shown). The electrode imparts a charge to the scent released from the scent canister 260 to aid in scent release. The electrodes can either be part of the multimedia and scent storage medium 100", or may be part of a separate multimedia playback and scent recovery system.

IV. Fourth Alternate Embodiment

Figure 20:
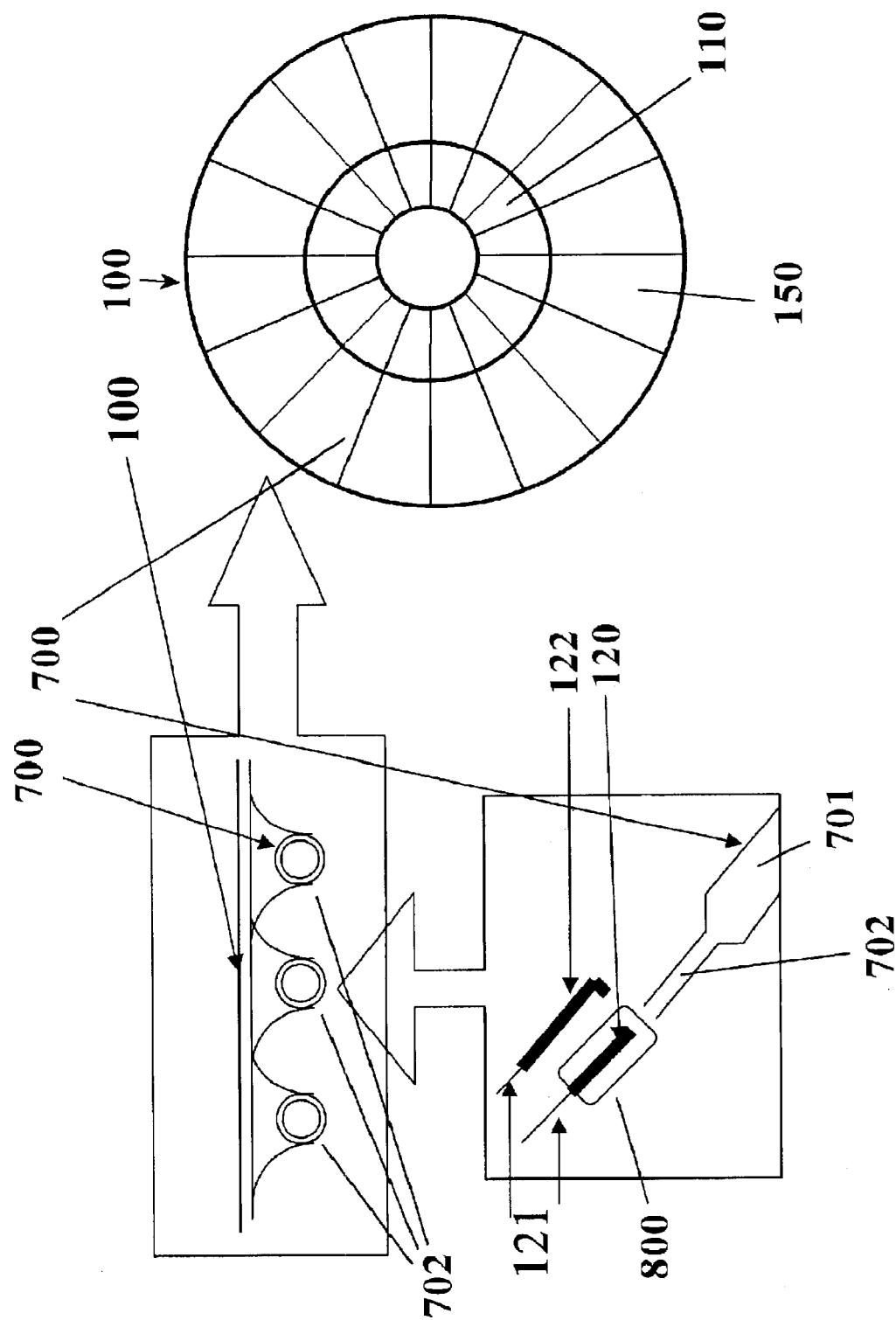
FIG. 20 depicts a top and side cross-sectional view of a multimedia and scent-bearing mediun 100 made in accordance with a fourth alternate embodiment of the present Invention.

A fourth alternate embodiment comprises a multimedia and scent-bearing medium having a capillary tube scent release system as depicted in FIG. 20. The multimedia and scent-bearing medium 100 comprises a multimedia storage medium 110; a scent storage region for storing multiple scents 150; scent identification information stored in the multimedia storage medium 1 10 for identifying which scents are stored in the scent storage region; and a capillary tube scent release system 700. In variants of the fourth alternate embodiment, the scent identification information may further comprise scent recovery information for sequencing recovery of scents stored in the scent storage region to coincide with audio and/or video information stored in the multimedia region. In FIG. 20, the capillary tube scent release system comprises a plurality of capillary tubes 702 extending from enclosures 701 for storing scent. The capillary tube can be made from glass, ceramic, plastic, nylon or other materials known to those skilled in the art. The enclosures for storing scent 701 can be in the form of a tube, ampule, three-dimensional sector as in the case of a disk, or any three-dimensional shape suitable for storing scent in liquid form. The capillary tubes 702 extending from enclosures 701 cause capillary action during scent recovery to aid in scent release. In typical operation, a multimedia playback and scent release system would bring a porous media 800 into very close proximity to the end of the capillary tube 702. Scent at the end of the capillary tube would contact the porous media and capillary action would cause the scent to pass into the porous media as a first step in scent release. Variants of the fourth alternate embodiment also may have electrodes 120, 122 and associated control circuitry 121 to provide an electrostatic scent release capability to operate in conjunction with the capillary tube scent release system.

Another variant of the fourth alternate embodiment comprises a scent-bearing medium which further comprises a plurality of enclosed regions for storing a plurality of scents wherein each of the enclosed regions have a capillary tube extending therefrom and scent identification means for identifying scents stored in the enclosed regions of the scent bearing medium. In contrast to the embodiment depicted in FIG. 20, this variant does not encode multimedia information in region 110, but can be used with multimedia information recovered from other sources (e.g., the Internet, CDs or DVDs) to create a virtual reality experience having audio, visual and scent stimulation. The scent identification means encoded in region 110 comprises scent identification information that can be used to sequence scent recovery to coincide with the multimedia information recovered from the remote source. In further variants, the scent identification means further comprises scent recovery sequence information for use in controlling the sequence of scent recovery from the scent-bearing medium.

V. Fifth Alternate Embodiment

Figure 21:
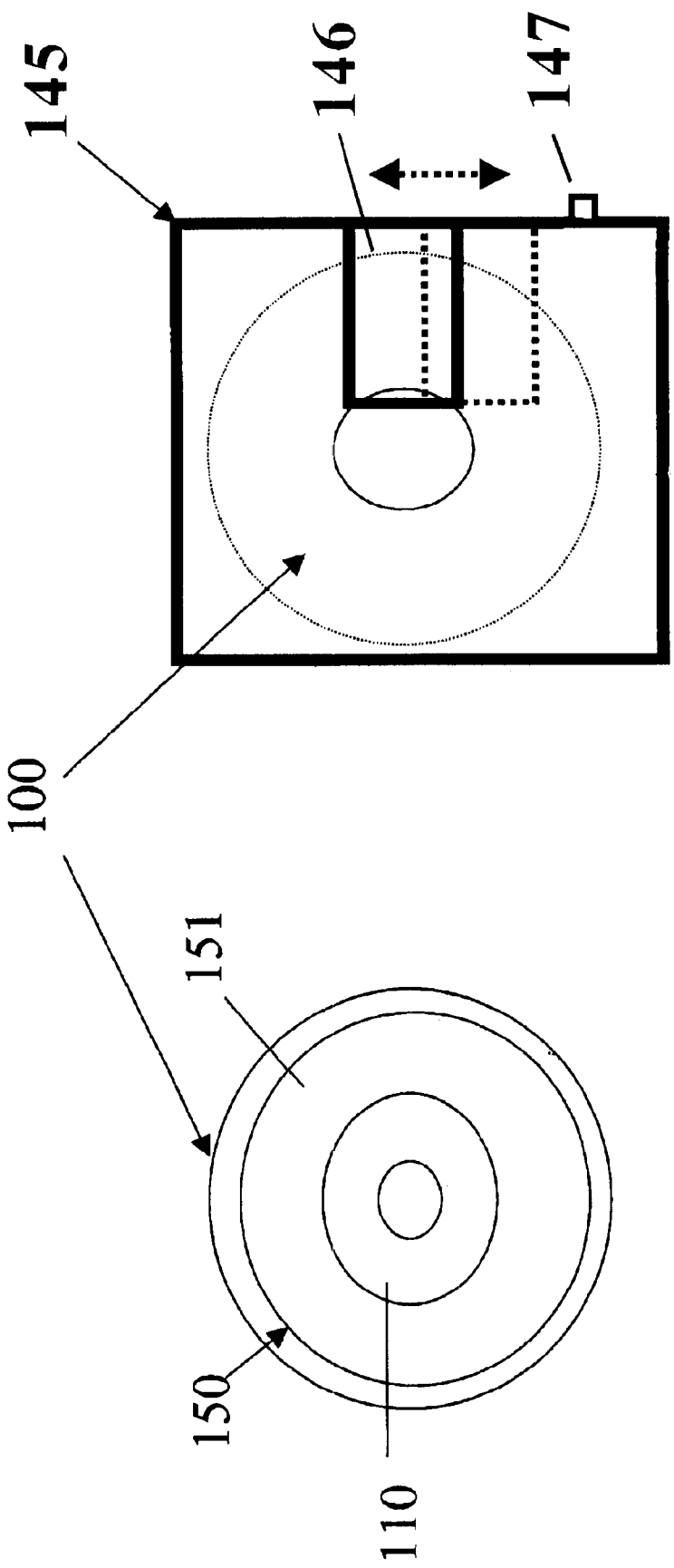
FIG. 21 depicts a top view of a multimedia and scent-bearing medium 100 made in accordance with a fifth alternate embodiment of the present invention.

A fifth alternate embodiment of the present invention comprises a multimedia and scent-bearing medium 100 having electrostatic scent release and a rigid housing 145 as depicted in FIG. 21. The rigid housing has a retractable door 146 that shields the multimedia and scent-bearing medium 100 when not in use. When placed in a multimedia playback and scent recovery system, the retractable shield 146 retracts, exposing at least a portion of the multimedia and scent-bearing medium so that scent may be recovered by the multimnedia playback and scent recovery system from the multimedia and scent-bearing medium. The rigid housing 145 may be made from any suitable rigid material, including impact-resistant plastic and nylon materials, and other materials well known to those skilled in the art. The housing further comprise an electrical connection 147 for use in imparting a potential difference between the electrodes of the electrostatic scent release system.

VI. Sixth Alternate Embodiment

Figure 22:
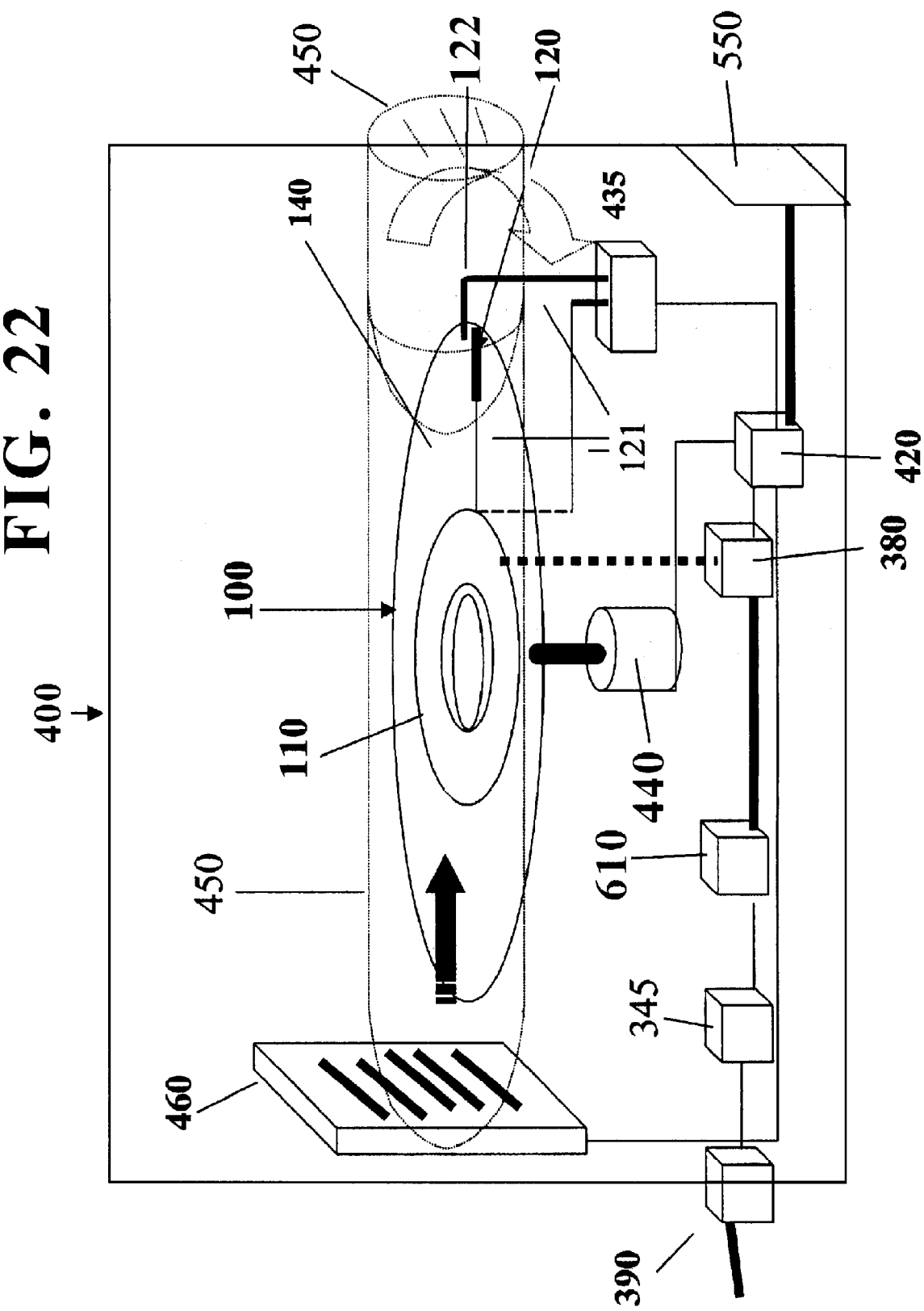
FIG. 22 depicts a schematic cross-sectional side view of an alternate scent recovery system 400 made in accordance with a sixth alternate embodiment of the present invention for use in combination with a multimedia and scent-bearing medium 100.

A sixth alternate embodiment of the present invention is depicted in FIG. 22 and comprises the combination of a multimedia and scent storage medium 100 and an integrated multimedia playback and scent recovery system having an electrostatic scent release system 400. The electrostatic scent release system 400 comprises an electrode 122, associated control circuitry 121, and an electrostatic scent release controller 435 which operates in response to control signals provided by control signal generator 420 (e.g. Motorola's 8000 series microprocessor). The first step in synchronized multimedia playback and, scent recovery comprises the recovery and storage of multimedia information, scent recovery sequence information, tag information, and multimedia information from the multimedia storage medium 110. The information is collectively stored in local storage system 610. After playback of multimedia information is initiated, controller 380 (e.g. CMOS PIC microcontroller) uses the tag information and scent recovery sequence information to control scent recovery from the scent storage region so that scent recovery coincides with multimedia playback. The control signal generator issues a control signal to electrostatic scent release controller 435 when the scent release sequence information indicates that scent should be released. The tag information is used to locate the scent that should be released. In a typical sequence, the control signal generator would determine that a particular scent, e.g., Scent 1, should be released for ten seconds so as to coincide with a particular multimedia sequence. The electrostatic scent release system would use the tag information to identify where on the disk Scent 1 is located. The disk would then be rotated so that the region of the disk 100 containing Scent 1 coincides with electrode 122 of the electrostatic scent release system 400. The scent release sequence information would then be used by the control signal generator 420 to issue a control signal to electrostatic scent release controller 435 indicating that Scent I should be released for ten seconds. Electrostatic scent release controller 435 would energize electrodes 120, 122 for ten seconds, thereby releasing Scent 1. Scent 1 would then be exhausted to the atmosphere by ductwork 450 and controlled fan 460. Preferably, the rotation of scent-bearing medium 100 so that the appropriate scent region aligns with the electrode 120 of the electrostatic scent release system 400 is accomplished using a controlled motor 440 (e.g. bipolar stepper motor).

Figure 23:
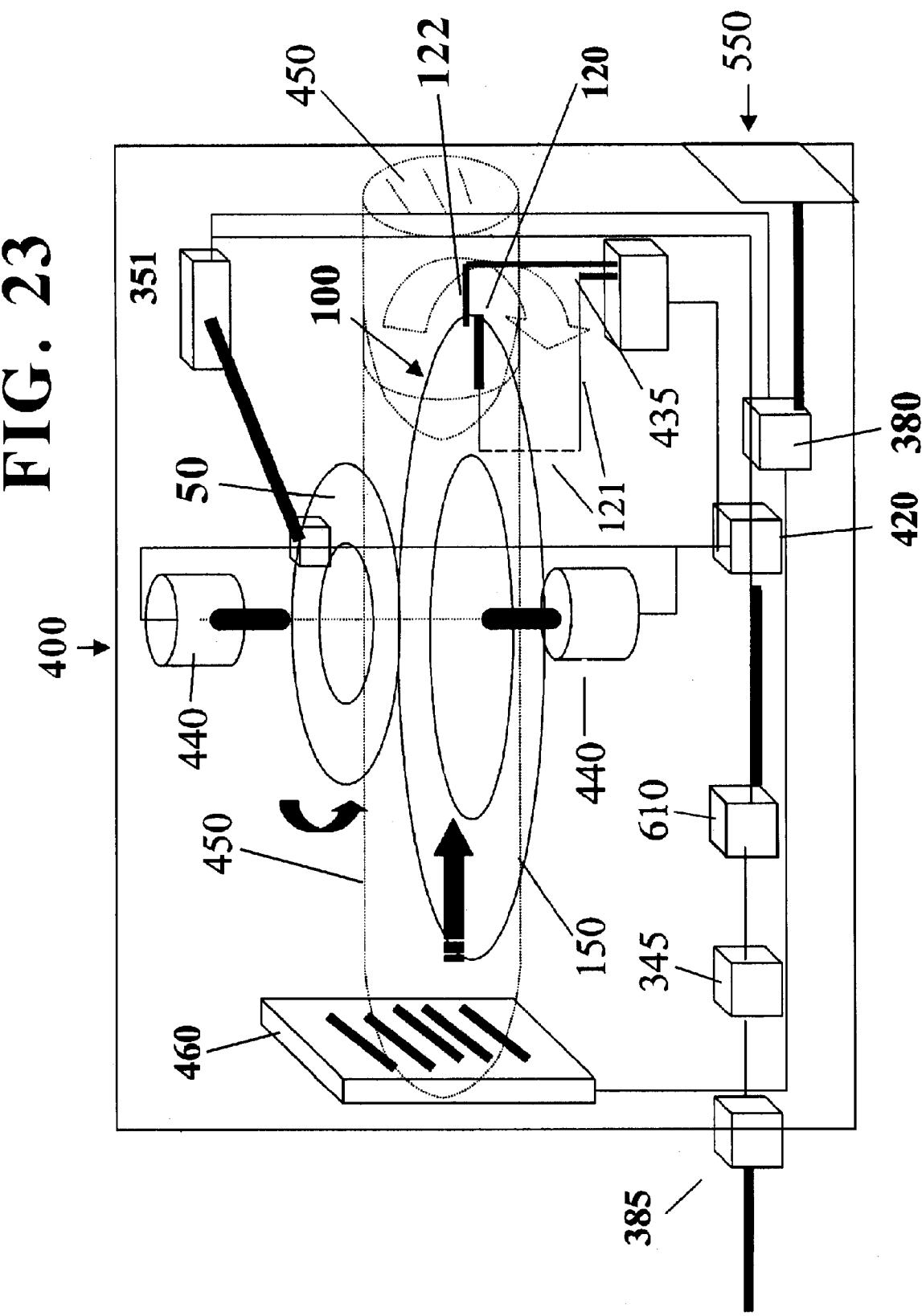
FIG. 23 depicts a schematic cross-sectional side view of an alternate scent recovery system 400 made in accordance with a sixth alternate embodiment of the present invention for use in combination with a multimedia and scent-bearing medium 100.

In a variant of the sixth alternate embodiment shown in FIG. 23, the multimedia playback and scent recovery system is capable of operating with a separate multimedia storage medium 50 (e.g. a compact disc) and scent-bearing medium 100. This variant may also be used with a single disk that has both multimedia and scent regions. The ability to use a separate multimedia disk (e.g., a DVD) means that a user could use scent recovered from a separate disk in combination with multimedia information recovered from another source (e.g., the DVD). In the variant shown in FIG. 23, this is accomplished by having two playback systems, one for a disk 50 and one for a disk 100 having a scent-bearing region. This may be accomplished in other ways, though. For example, in a single playback system, the user would place the multimeidia disk having the desired multimedia information into the playback system to recover the desired multimedia information, which would then be stored in memory 610. Then the multimedia disk would be removed, and be replaced by a disk having the desired scent. the variant shown in FIG. 23 has playback system 351 and motor 440 for recovering multimedia information from multimedia disk 50.

Figure 24:
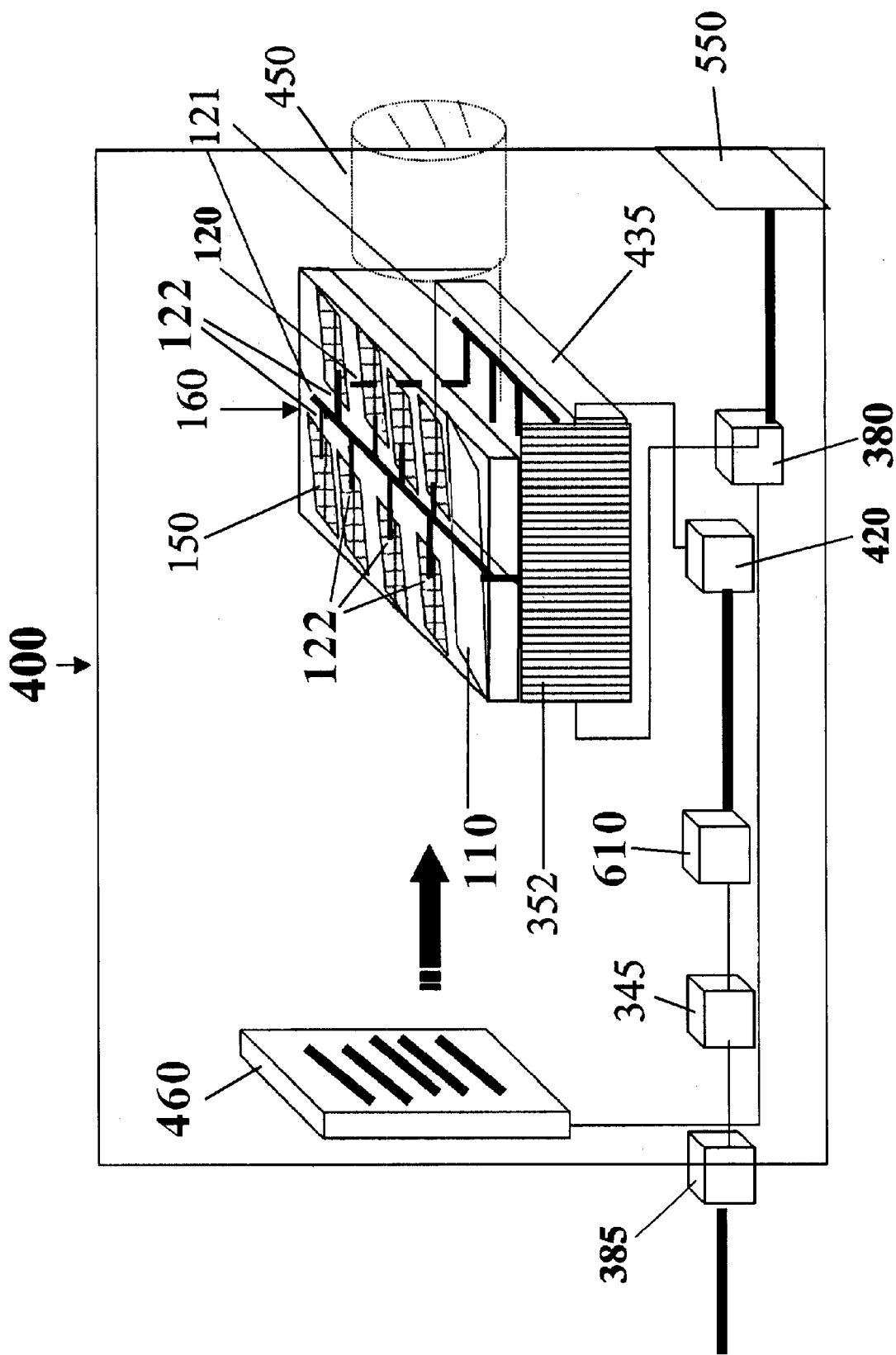
FIG. 24 depicts a schematic cross-sectional side view of an alternate scent recovery system 400 made in accordance with a sixth alternate embodiment of the present invention for use in combination with a multimedia and scent-bearing medium 160.

FIG. 24 depicts another variant of the sixth alternate embodiment. The variant shown in FIG. 24 operates with a multimedia and scent-bearing medium 100 that stores information either electrically or magnetically (e.g., in FLASH memory or magnetic memory). The electrostatic scent recovery system 400 includes multiple electrodes 122 and associated control circuitry 121 which operate in response to control signals provided by the control signal generator 420. The insertable scent card 160 electronically connects with the controller 380 through a connector type magnetic playback system 352. After recovery of the scent recovery sequence information, tag information, and multimedia information from the multimedia storage medium 110 and storage of this information in the local storage system 610, the controller 380 can use the tag information as reference data to couple event-related scent recovery signals which either have been transmitted from a remote multimedia source 390 or from the multimedia storage medium 110 to emit predetermined scent or combination of scents from the scent card 160 by a ductwork 450 and controlled fan 460.

Figure 25:
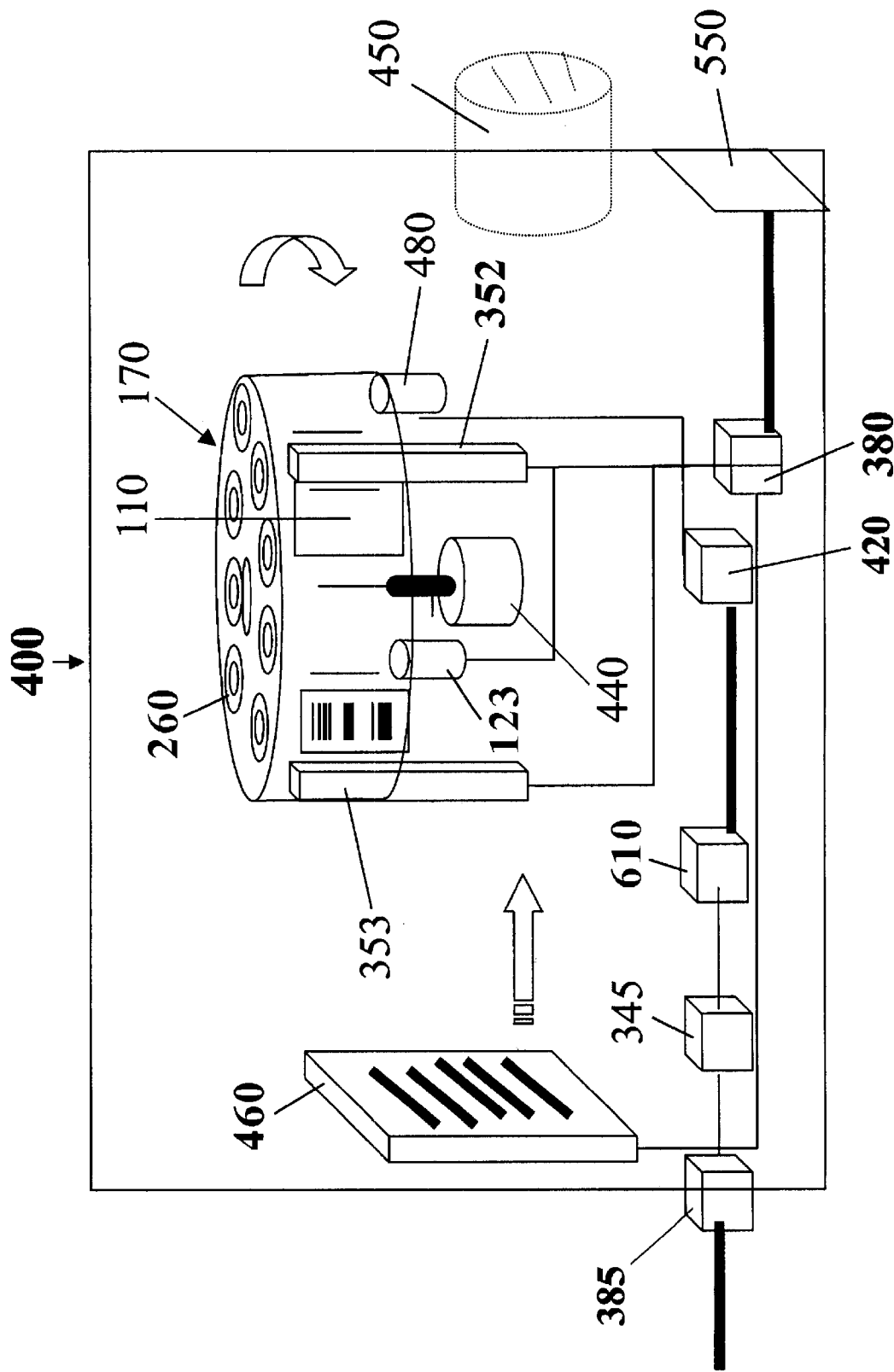
FIG. 25 depicts a schematic cross-sectional side view of an alternate scent recovery system 400 made in accordance with a sixth alternate embodiment of the present invention for use in combination with a multimedia and scent-bearing medium 170.

A further variant of the sixth alternate embodiment is depicted in FIG. 25. The scent recovery system 400 includes a selectively controlled release valve system 480 which operates in response to control signals provided by the control signal generator 420. A barcode reader 353 or magnetic playback system 352 will retrieve the scent recovery sequence information, tag information, and multimedia information from the scent identification 120 or multimedia storage medium 110 into the local storage system 610, the controller 380 can use the tag information as reference data to couple event-related scent recovery signals which either have been transmitted from a remote multimedia source 390 or from the multimedia storage medium 110 to emit predetermined scent or combination of scents from the cartridge 170 by a ductwork 450 and controlled fan 460. A replaceable scent cartridge 170 that emits a predetermined scent or a combination of scents when activated. Preferably, a predetermined scent from a canister 260 from the scent cartridge 170 is positioned directly in front of the ductwork 450 and controlled fan 460 by a controlled motor 440. Housing 123 contains electrodes (not shown) that are used to impart a charge to scents released from the scent canisters 260 to aid in scent release.

Figure 26:
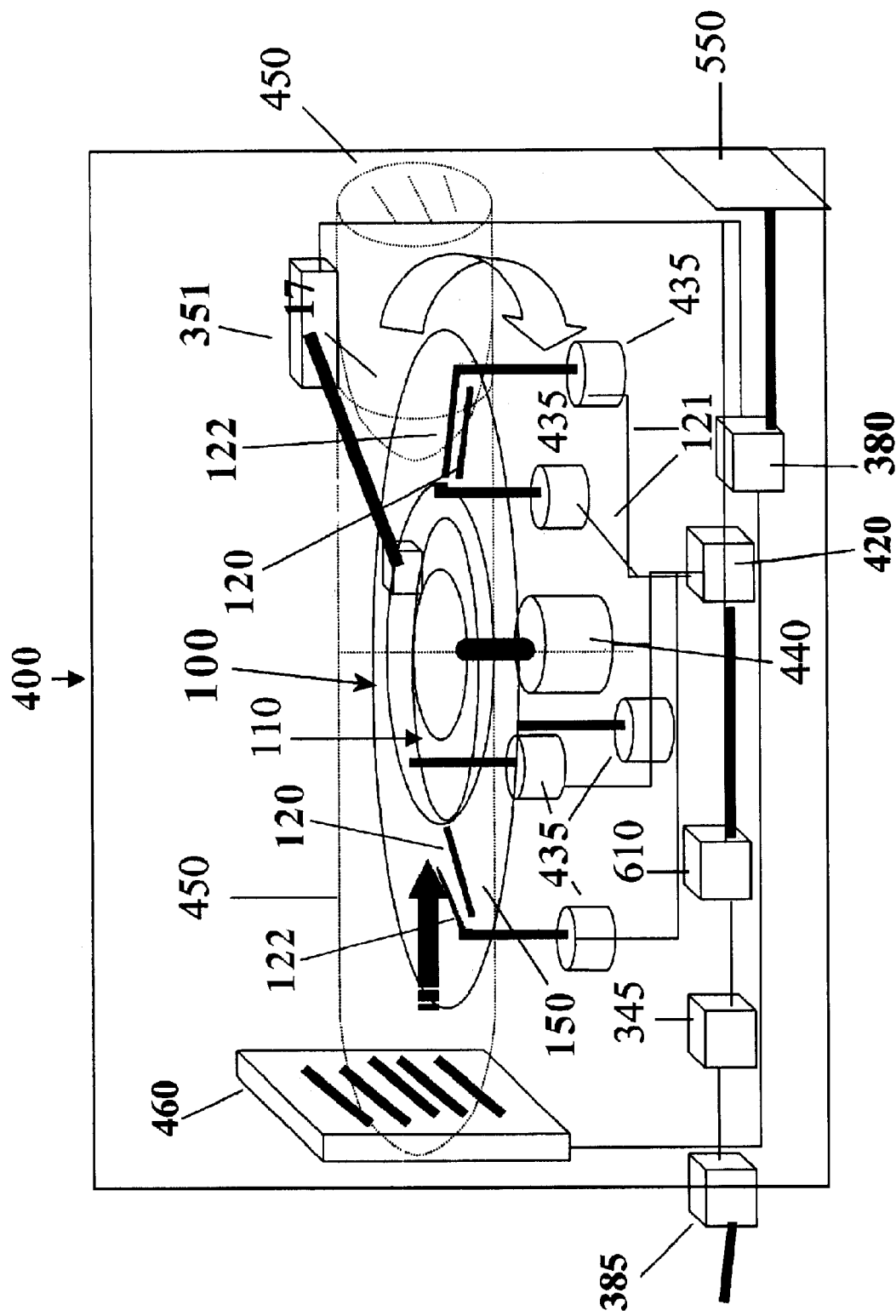
FIG. 26 depicts a schematic cross-sectional side view of an alternate scent recovery system 400 made in accordance with a sixth alternate embodiment of the present invention for use in combination with a multimedia and scent-bearing medium 100.

A still further variant of the sixth alternate embodiment is shown in FIG. 26. In this embodiment, the playback system comprises a scent disk 100 having not only scent-bearing medium 110 but also a multimedia storage medium 150 (e.g. a compact disc), with scent recovery sequence information, tag information, and multimedia information encoded thereon. A multimedia playback system 350 including, an optical playback system 351 serves as the recovery system for accessing and processing the scent recovery sequence information, tag information, and multimedia information stored on the multimedia storage medium 110. The optical playback system 351 transmits scent recovery sequence information, tag information, and multimedia information to the controller 380 which encodes scent recovery sequence information into electronic signals prior to transmitting to the scent recovery system 400 or to a local storage system 610. A control signal generator 420 then retrieves the electronic signals to the scent recovery system 400. The system has a plurality of electrodes 122 to accomplish scent release.

VII. Seventh Alternate Embodiment

Figure 27:
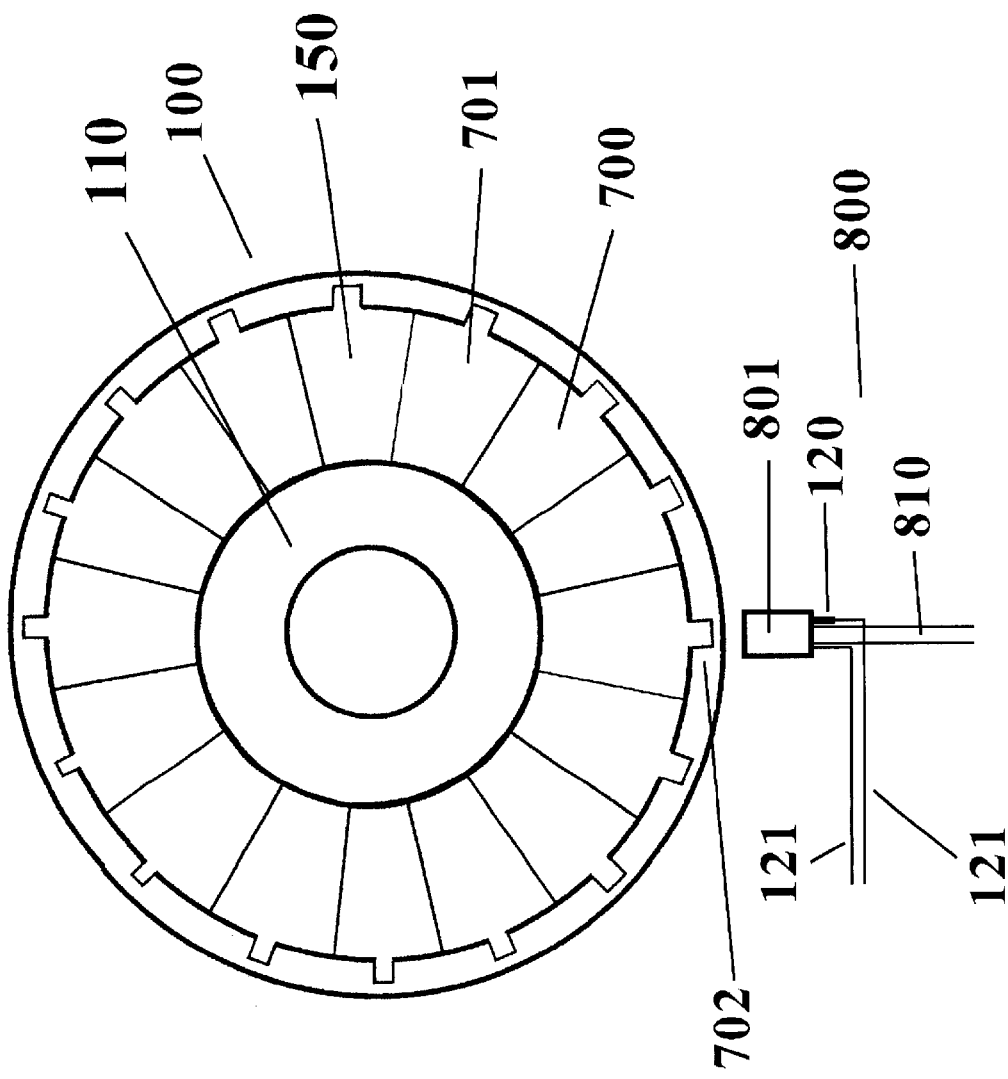
FIG. 27 depicts a top view of a scent recovery system made in accordance with a seventh alternate embodiment of the present invention.

A seventh alternate embodiment of the present invention is shown in FIG. 27 and comprises a porous media scent recovery system 800 that can be used in combination with a multimedia and scent storage medium 100 having a capillary tube scent release system. The porous media scent recovery system 800 can be combined with elements of the previous embodiments in various ways. For example, the porous media scent recovery system can be combined with the multimedia playback and scent recovery features of the preceding embodiments to create a multimedia playback and scent recovery system having a porous media scent recovery system.

The porous media scent recovery system 800 preferably comprises a porous media 801 that can be moved back and forth between a position where it is close to a capillary tube 702 of a scent enclosure 701 of the multimedia and scent bearing medium 100, and to a position where it is relatively far away. This can be accomplished with motor drives well known to those skilled in the art. When it is relatively close to the capillary tube 702, scent will flow into the porous media 801 by capillary action. The porous media 801 preferably comprises a nylon or plastic matrix or other material known to those skilled in the art of sufficient dimensions to sustain capillary flow between the capillary tube 702 of the multimedia and scent-bearing medium 100 and the porous media. The porous media scent recovery system 800 further comprises a duct 810 for use in transferring scent recovered from the multimedia and scent bearing medium 100 to a location close to a user of a multimedia playback and scent recovery system having the porous media scent recovery system 800. Preferably, the porous media scent recovery system 800 further comprises a fan for providing a positive pressure to entrained scent in the porous media 801 in a gas flow so that it may be more efficiently dispersed. Variants of the seventh alternate embodiment may further comprise an electrostatic scent release system comprising electrodes 120 and associated control circuitry 121 to aid in scent release.

VIII. Eighth Alternate Embodiment

Figure 28:
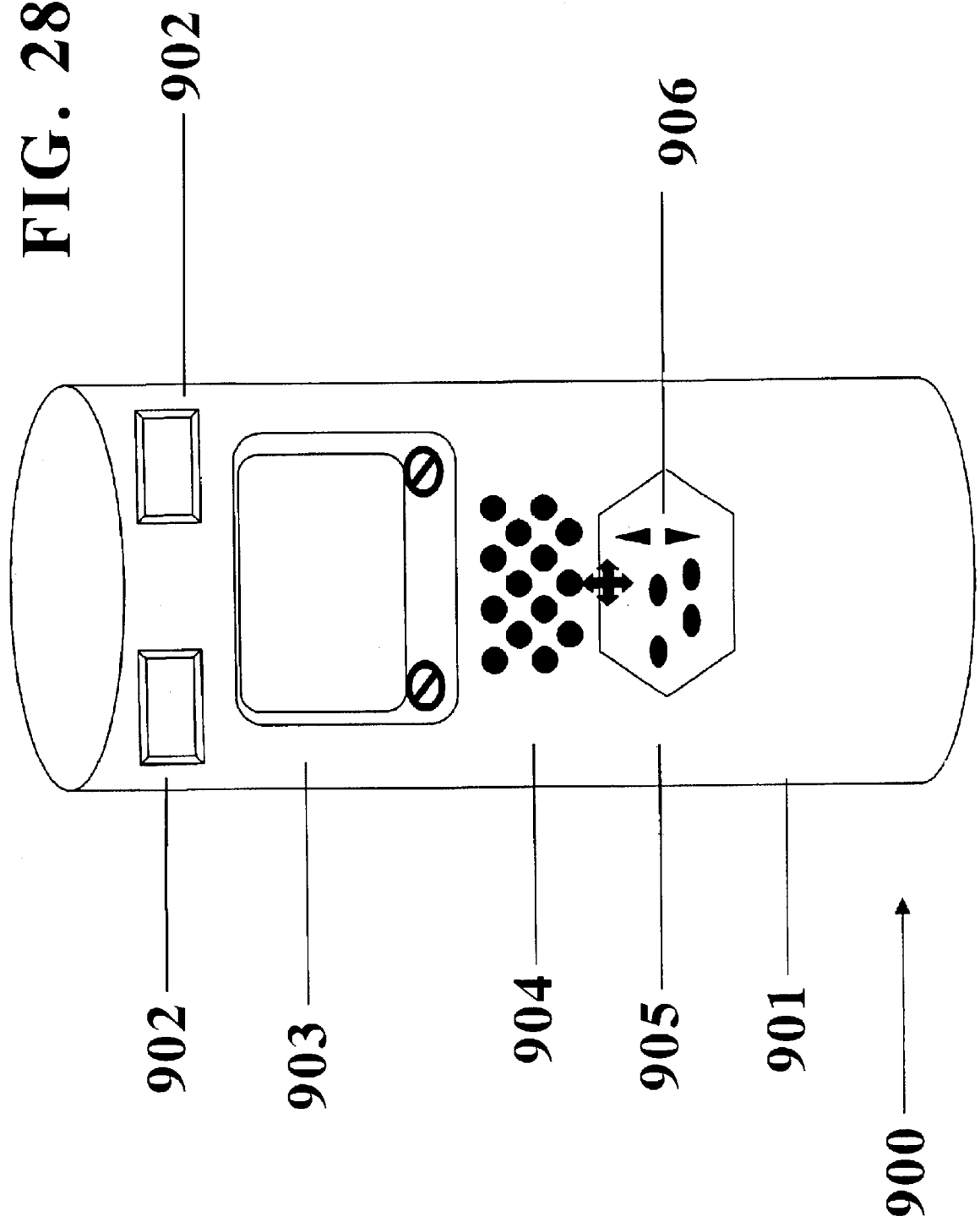
FIG. 28 depicts a perspective view of kiosk having a multimedia playback and scent recovery system made in accordance with an eighth alternate embodiment of the present invention.

An eighth alternate embodiment of the present invention is depicted in FIG. 28 and comprises a kiosk 900 having multimedia playback and scent recovery capability. The kiosk 900 can be used in retail establishments to market scents, e.g., perfumes, in combination with a multimedia segment, e.g., marketing material. The kiosk preferably comprises a floor-standing housing 901 for enclosing a multimedia playback and scent-recovery system made in accordance with the present invention (not shown); speakers 902; a video monitor 903; vents 904; and a touch panel 905 for operation by users (e.g., potential customers for a perfume). During use, the kiosk would be positioned in a retail establishment in a customer-accessible location, e.g., close to a display case of perfume. The potential customer would approach the kiosk 900, press buttons 906 on the control panel 905, at which point the multimedia playback and scent recovery system would begin a multimedia playback and scent recovery sequence. During the sequence, video would be displayed on the video monitor 903, music and/or voice information would be played over the speakers 902, and scent (e.g., perfume) would be vented through exhaust vents 904 for sampling by the potential customer.

Figure 29:
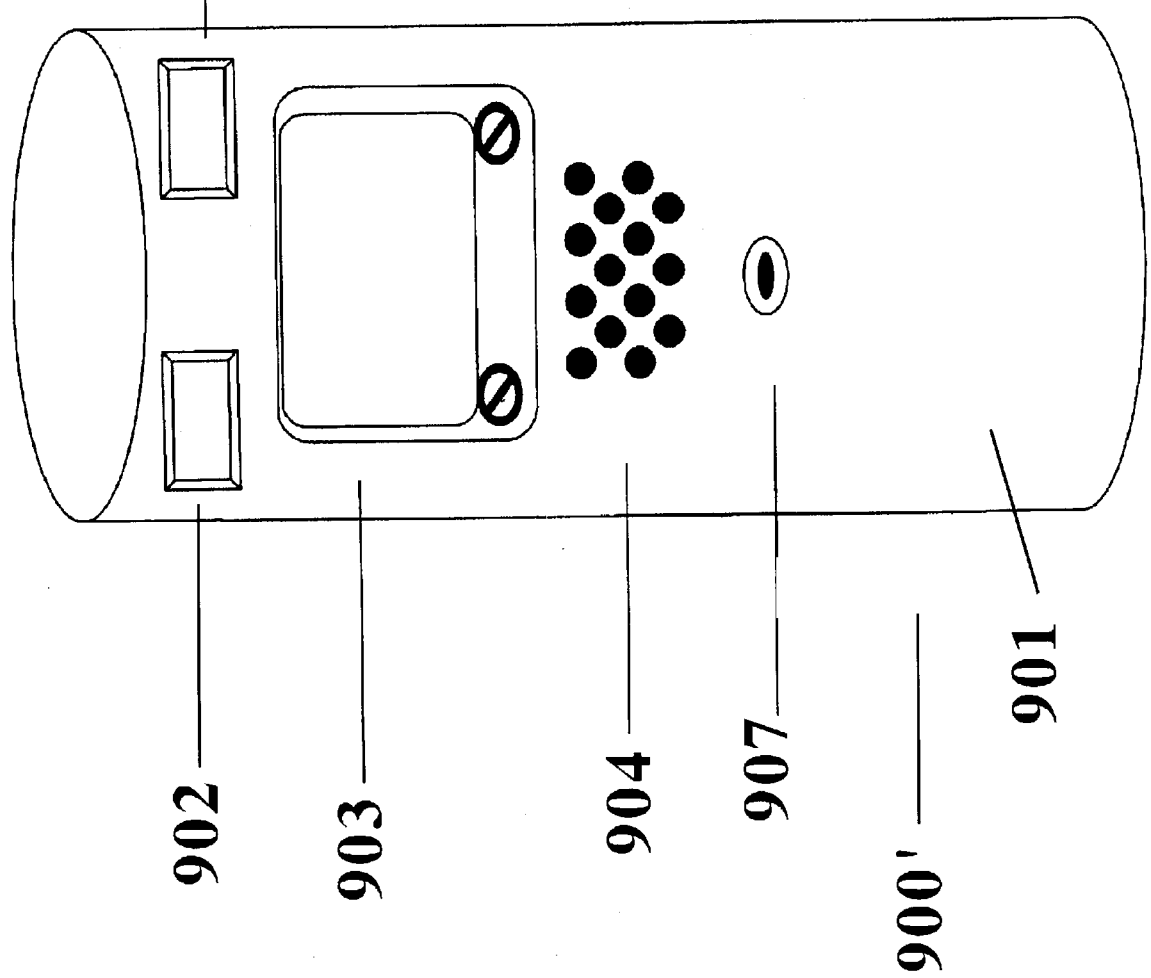
FIG. 29 depicts a perspective view of a kiosk having a multimedia playback and scent recovery system made in accordance with a variant of the eighth alternate embodiment of the present invention.

A variant of the eighth alternate embodiment is depicted in FIG. 29 and comprises a kiosk 900' having multimedia playback and scent-recovery capability. In contrast to the touch panel 905 depicted in FIG. 28, the kiosk 900' depicted in FIG. 29 has a human proximity sensor 907 for initiating a multimedia playback and scent-recovery sequence. During operation, the kiosk 900' would be placed in a retail establishment in a customer-accessible location. The human proximity sensor 907 is designed to detect the close proximity of humans to the kiosk. In variants of the eighth alternate embodiment, the human proximity sensor 907 may comprise an infrared, voice, or motion detector, examples of which are known to those skilled in the art When a human (e.g., potential customer) moves within the effective range of the human proximity sensor 907, the sensor 907 issues a command to the multimedia playback and scent recovery system to initiate a multimedia playback and scent recovery sequence. Thus customers passing by the kiosk 900' would have a complete sensory experience including sampling of a scent (e.g., perfume) as well as listening to music and voice information and viewing video information.

Figure 30:
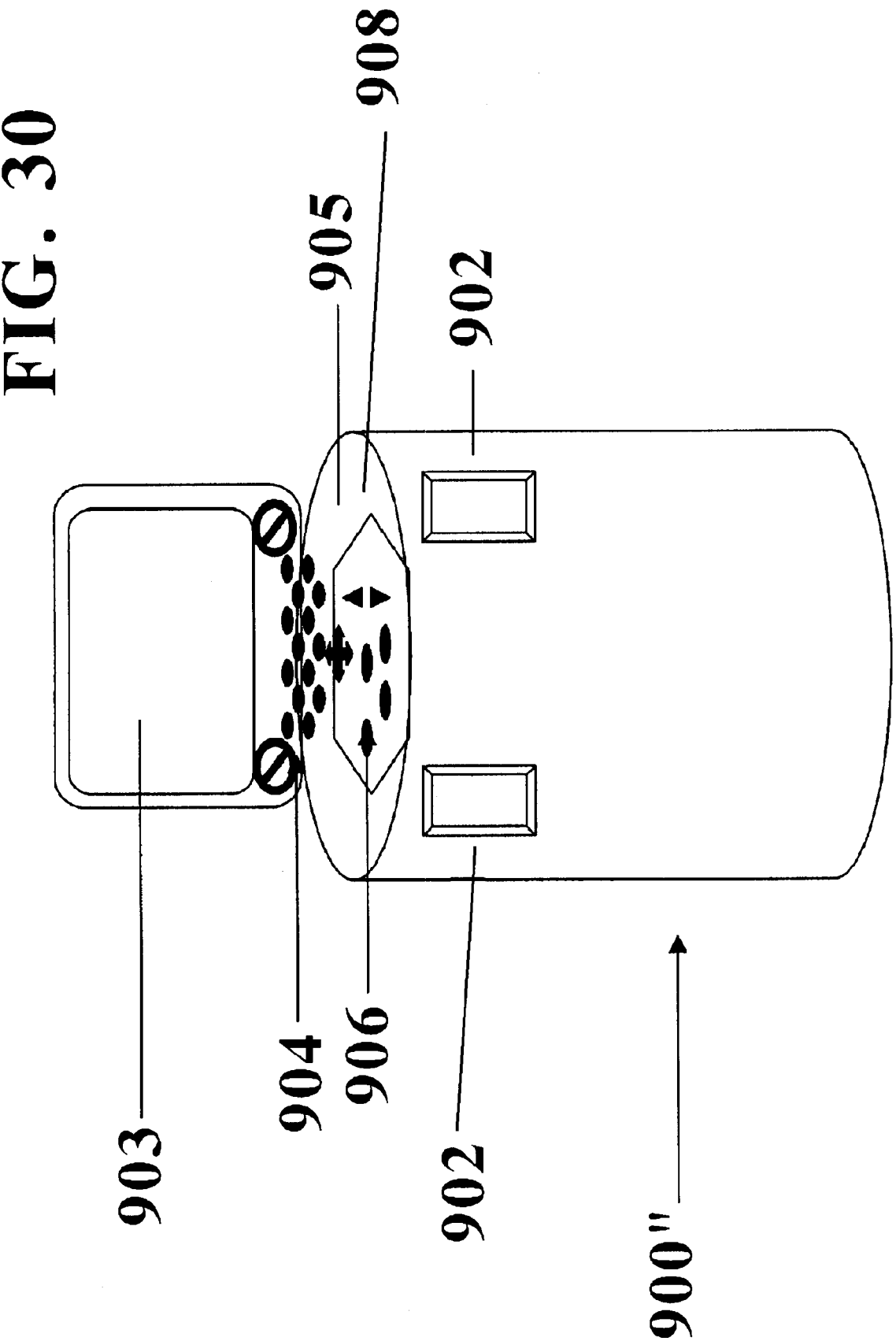
FIG. 30 depicts a perspective view of a counter-mounted multimedia playback and scent recovery system made in accordance with a variant of the eighth alternate embodiment of the present invention.

Another variant of the seventh alternate embodiment comprises a counter-mounted multimedia playback and scent-recovery system 900". In contrast to the floor-standing kiosk, the multimedia playback and scent recovery system 900" is designed to be placed either, on top of a counter-top in a retail establishment (not shown) or built in to a countertop 908 as shown in FIG. 30.

Figure 31:
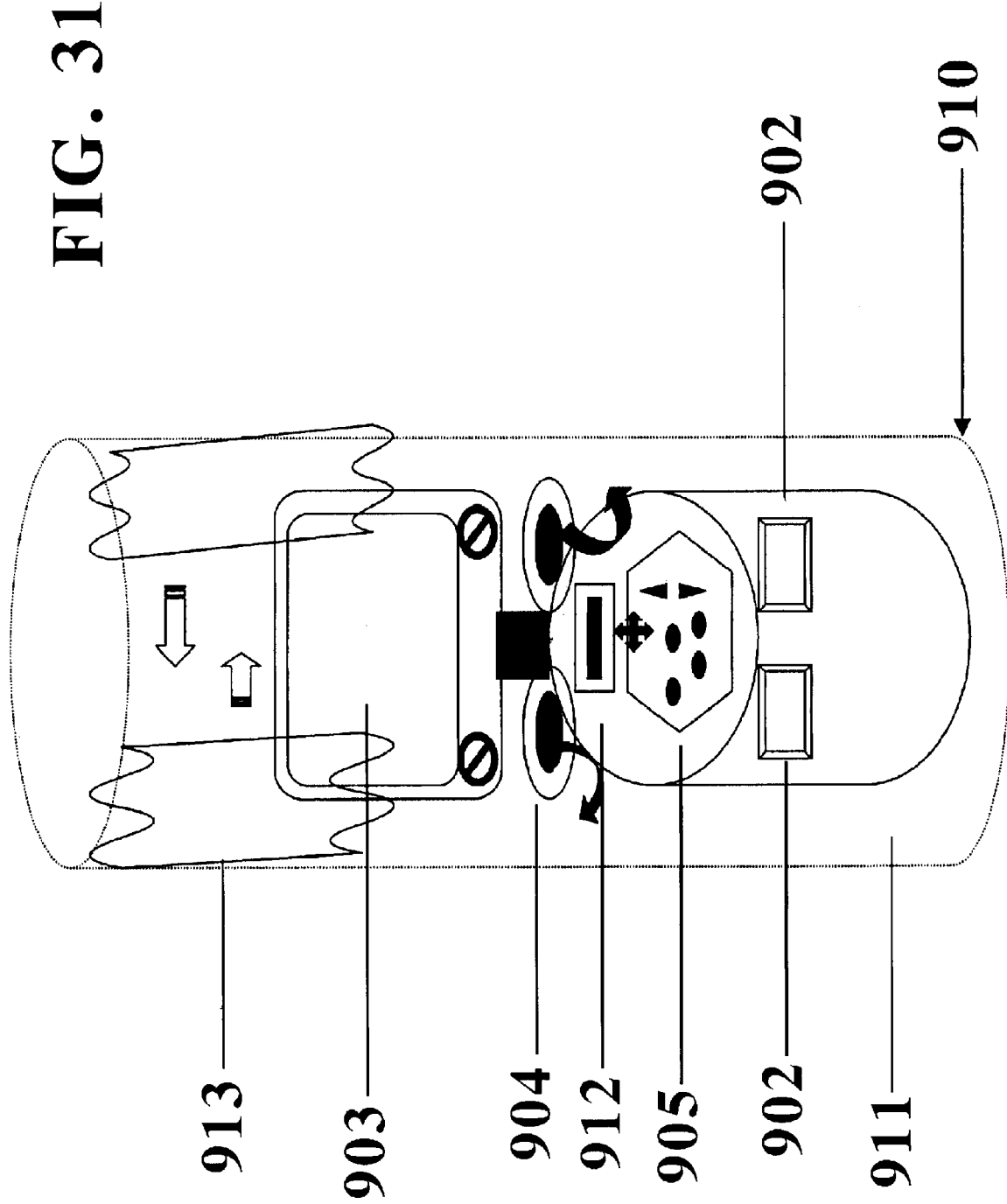
FIG. 31 depicts a perspective view of a booth having a multimedia playback and scent recovery system made in accordance with a variant of the eighth alternate embodiment of the present invention.

A still further variant of the seventh alternate embodiment comprises a booth 910 having multimedia playback and scent recovery capability as shown in FIG. 31. The booth 910 preferably comprises a housing 910 for enclosing a multimedia playback and scent recovery system made in accordance with the present invention; a video monitor 903; speakers 902; exhaust vents 904; a slot 912 for accepting a multimedia and scent-bearing medium made in accordance with the present invention; and a touch panel 905 for controlling operation of the multimedia playback and scent recovery system. Immediately adjacent to the housing of the booth is an enclosed, user-accessible region where the user may stand or sit in close proximity to the housing. The enclosed, user accessible region may be formed in many ways. In FIG. 31, curtains 913 extend from the top, of the booth. The curtains can be retracted to allow entry or exit, and closed to form an enclosed region. Alternately, the enclosed region may be formed by two walls extending outward from the housing and a door and door structure extending between the two walls.

IX. Ninth Alternate Embodiment

Figure 32:
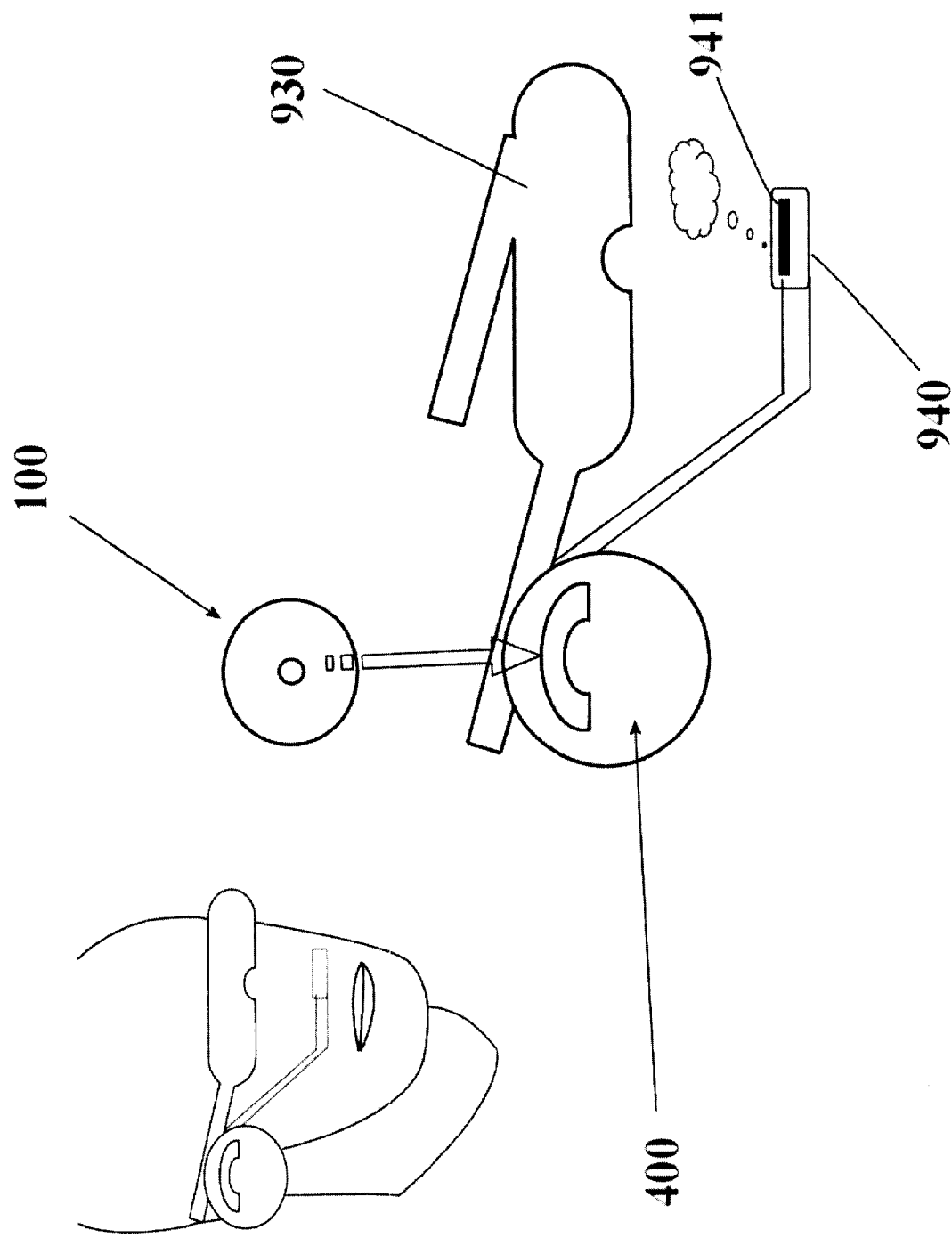
FIG. 32 depicts a conceptual view of-a ninth alternate embodiment of the present invention.

A ninth alternate embodiment of the present invention comprises a head-mounted scent recovery and multimedia playback system as depicted in FIG. 32. Video information recovered from the multimedia and scent-bearing disk 100 is displayed on a display positioned in the head-mounted mask. Scent recovered from the multimedia and scent-bearing medium is conveyed to the user's nose through a tube 940 and vent 941.

Thus, it is seen that a multimedia and scent storage medium and playback apparatus having electrostatic scent release is provided. One skilled in the art will appreciate that the present invention can be practiced in other applications where similar features are desired. The foregoing description of the present invention has been presented for purposes of illustration and description, and not for purposes of limitation. It is not intended to be exhaustive or to limit the invention to the precise forms disclosed, and many modifications and variations are possible in light of the above disclosures.

What is claimed is:

1. A multimedia and scent-bearing medium for use in conjunction with a separate, integrated multimedia playback and scent recovery system, the multimedia and scent-bearing medium comprising:

multimedia storage means for storing multimedia information;

scent storage means for storing at least one scent;

scent identification means for storing scent identification information for use by the separate, integrated multimedia playback and scent recovery system to identify the scent stored in the scent storage means;

an electrostatic scent release means for electrostatically releasing scent from the scent storage means; and wherein the separate multimedia storage means, scent storage means, scent identification means and electrostatic scent release means of the multimedia and scent-bearing medium together comprise an integrated unit.

2. The multimedia and scent-bearing medium of claim 1 wherein the scent storage means stores a plurality of scents and wherein the scent identification means identifies each of the plurality of scents that are stored in the scent storage means.

3. The multimedia and scent-bearing medium of claim 2 wherein the scent storage means storing the plurality of scents further comprises:

a plurality of recessed three-dimensional regions each having an upwardly facing opening and each for storing a separate scent;

an inert storage medium deposited within the recessed three-dimensional regions for storing separate, electrostatically-releasable scents deposited within the providing an olfactory ("scent") stimulation, particularly scent media that are intended to operate inert storage medium; and a gas permeable membrane placed over the upwardly-facing openings, wherein the gas-permeable membrane permits the scents to escape from the three-dimensional regions when the scents are electrostatically released.

4. The multimedia and scent-bearing medium of claim 3 wherein the gas permeable membrane comprises a microporous polymer.

5. The multimedia and scent-bearing medium of claim 3 wherein the gas permeable membrane comprises a macroporous polymer.

6. The multimedia and scentbearing medium of claim 2 wherein the scent-bearing medium further comprises a scent-neutralizing material for neutralizing or masking scents previously released from the multimedia and scent-bearing medium.

7. The multimedia and scent-bearing medium of claim 2 wherein the multimedia information further comprises:

scent recovery sequence information for controlling the sequential recovery of separate scents stored in the multimedia and scent-bearing medium.

8. The multimedia and scent-bearing medium of claim 7 wherein the multimedia information further comprises digitally-encoded audio information.

9. The multimedia and scent-bearing medium of claim 7 wherein the multimedia information further comprises digitally-encoded video information.

10. The multimedia and scent-bearing medium of claim 7 wherein the multimedia information further comprises digitally-encoded photographs.

11. The multimedia and scent-bearing medium of claim 7 wherein the multimedia information further comprises digitally-encoded textual information.

12. The multimedia and scent-bearing medium of claim 7 wherein the multimedia information further comprises digitally-encoded graphical information.

13. The multimedia and scent-bearing medium of claim 7 wherein the scent recovery information further comprises multiple scent recovery information for controlling the simultaneous recovery of multiple scents.

14. The multimedia and scent-bearing medium of claim of 9 wherein the scent recovery sequence information controls the sequential recovery of scent stored on the multimedia and scent-bearing medium to coincide with audio information or video information.

15. The multimedia and scent-bearing medium of claim 7 wherein the multimedia information is segregated into separately-recoverable multimedia segments for use with an interactive playback system.

16. The multimedia and scent-bearing medium of claim 15 wherein the scent recovery information further comprises tag information for tagging particular scents to particular separately-recoverable multimedia segments.

17. The multimedia and scent-bearing medium of claim 1 wherein the multimedia storage means further comprises a substrate suitable for optically-encoding multimedia information for laser playback or recovery.

18. The multimedia and scent-bearing medium of claim 17 wherein the substrate for optically-encoding multimedia information permits overwriting of previous multimedia information with new multimedia information.

19. The multimedia and scent-bearing medium of claim 1 wherein the multimedia storage means further comprises a substrate suitable for magnetically encoding multimedia information for magnetic playback or recovery.

20. The multimedia and scent-bearing medium of claim 19 wherein the substrate for magnetically encoding multimedia information permits overwriting of previous multimedia information with new multimedia information.

21. The multimedia and scent-bearing medium of claim 1 wherein the multimedia storage means further comprises a substrate suitable for bar code encoding of multimedia information for playback or recovery.

22. The multimedia and scent-bearing medium of claim 1 wherein the scent storage means further comprises:
   a housing having a plurality of storage slots;
   a plurality of canisters for positioning in the storage slots, each of the canisters for storing scent, and each of said canisters also having a release valve for releasing the scents stored in the canisters; and
   wherein the scent identification means identifies which scents are loaded in which slots of the housing.

23. The multimedia and scent-bearing medium of claim 22 wherein the scent identification means comprises bar codes.

24. The multimedia and scent-bearing medium of claim 1 further comprising a storage case having sealing means for storing the multimedia and scent-bearing medium in a manner so that the scent is prevented from escaping.

25. The multimedia and scent-bearing medium of claim 1 further comprising a reusable gas impermeable membrane for placing over the scent storage means when the multimedia and scent-bearing medium is not in use to prevent the scent stored in the scent storage means from escaping.

26. The multimedia and scent-bearing media of claim 1 wherein the electrostatic scent release means further comprises:
   at least one electrode.

27. The multimedia and scent-bearing medium of claim 3 wherein the electrostatic scent release means further comprises:
   at least one electrode placed in each of the recessed, three-dimensional regions.

28. The multimedia and scent-bearing of claim 3 wherein the electrostatic scent release. means further comprises:
   a pair of electrodes placed in each of the recessed, three-dimensional regions; and
   associated control circuitry for permitting a remote electrical source to impart a potential difference between each of the pairs of electrodes placed in the recessed three-dimensional regions.

29. A multimedia and scent-bearing medium for use in conjunction with a separate, integrated multimedia-playback and scent recovery system the multimedia and scent-bearing medium comprising:
   multimedia storage means for storing multimedia information;
   scent storage means for storing at least one scent;
   scent identification means for storing scent identification information for use by the separate, integrated multimedia playback and scent recovery system to identify the scent stored in the scent storage means;
   an electrostatic scent release means for electrostatically releasing scent from the scent storage means; and
   a rigid housing for enclosing the multimedia storage needs, the scent storage means, and the scent identification means, wherein said rigid housing further comprises:
   a retractable door that moves between at least two positions,
      wherein in the first of said at least two positions the door is closed, and in the second of at least two positions the door is open and exposes at least a portion of either the multimedia storage means, the scent storage means, or the scent identification means so that multimedia information, scent identification information or scent may be recovered from these means;
      an electrical connection so that a potential difference may be imparted to the electrostatic scent release means.

30. An integrated system comprising a multimedia and scent-bearing medium and a separate multimedia playback and scent recovery system for playback of multimedia information aid recovery of scents stored in the multimedia and scent-bearing medium wherein:
   the multimedia and scent-bearing medium comprises:
   multimedia storage means for storing multimedia information;
   scent storage means for storing at least one scent;
   scent identification means for storing scent identification information for use by the separate multimedia playback and scent recovery system to identify the scent stored in the scent storage means;
   electrostatic scent release means for releasing scent from the scent storage means; and
   an electrical connection for supplying electricity to the electrostatic scent release means;
   and wherein the multimedia playback and scent recovery system for use in combination with the multimedia and scent-bearing medium comprises:
      multimedia playback means for recovering the multimedia information stored in the multimedia storage means;
      scent identification information recovery means for recovering the scent identification information from the scent identification means;
      scent recovery means for recovering the scents stored in the scent. storage means, wherein said scent recovery means further comprises an electrostatic scent recovery system;
      an electrical supply for providing electricity to the multimedia and scent-bearing medium through its electrical connection; and
      user input and control means for permitting the user of the integrated system to input commands for controlling the playback of multimedia information and recovery of scents stored in the multimedia and scent-bearing medium.

31. The integrated system of claim 30 wherein the multimedia information is optically-encoded in the multimedia storage means and wherein the playback means further comprises:
an optical playback system for retrieving the optically-encoded multimedia information.

32. The integrated system of claim 30 wherein the multimedia information is magnetically-encoded in the multimedia storage means and wherein the playback means further comprises:
a magnetic playback system for retrieving the magnetically-encoded multimedia information.

33. The integrated system of claim 30 wherein the multimedia information is encoded in the multimedia storage means using bar codes and wherein the playback means further comprises:
a bar code reader for reading the bar codes storing multimedia information.

34. The integrated system of claim 30 wherein the multimedia information comprises audio information and wherein the playback means further comprises:
an amplifier system for amplifying the audio signal recovered from the multimedia storage means; and
a speaker system connected to the amplifier system.

35. The integrated system of claim 30 wherein the multimedia information comprises audio information and wherein the playback means further comprises:
an amplifier system for amplifying the audio signal recovered from the multimedia storage means; and
a headphone system connected to the amplifier system.

36. The integrated system of claim 30 wherein the multimedia information comprises video information and wherein the playback means further comprises:
a visual display means for viewing the video information recovered from the multimedia storage means.

37. The integrated system of claim 36 wherein the visual display means comprises a monitor.

38. The integrated system of claim 36 wherein the visual display means comprises an LCD display.

39. The integrated system of claim 36 wherein the visual display comprises a a head-mounted miniature display system.

40. The integrated system of claim 36, wherein the visual display comprises a a mask display system.

41. The integrated system of claim 30 wherein the scent-bearing means of the multimedia and scent-bearing medium stores a plurality of scents.

42. The integrated system of claim 41 wherein the multimedia storage means of the multimedia and scent-bearing medium stores scent recovery sequence information for controlling the sequential recovery of the plurality of scents stored in the a multimedia and scent-bearing medium.

43. The integrated system of claim 42 wherein the scent recovery sequence information specifies which scents should be recovered from the multimedia and scent-bearing medium.

44. The integrated system of claim 43 wherein the scent recovery sequence information specifies the order in which scents are to be recovered from the multimedia and scent-bearing medium.

45. The integrated system of claim 44 wherein the scent recovery sequence information specifies the duration of recovery of each of the scents recovered from the multimedia and scent-bearing medium.

46. The integrated system of claim 42 wherein the multimedia player and scent recovery system further comprises:
means for storing the pre-programmed scent recovery sequence information; and
scent recovery sequence information: editing means for permitting the user to alter a pre-programmed scent recovery sequence stored in the multimedia and scent-bearing medium in order to create a user-specified scent recovery sequence.

47. The integrated system of claim 46 wherein the pre-programmed scent recovery sequence information identifies which scents are to be recovered from the multimedia and scent-bearing medium; and wherein the scent recovery sequence information editing means permits the user to delete certain of the scents from the pre-programmed scent recovery sequence in order to create a user-specified scent recovery sequence.

48. The integrated system of claim 46 wherein the pre-programmed scent recovery sequence information identifies which scents are to be recovered from the multimedia and scent-bearing medium and wherein the scent recovery sequence information editing means permits the user to add scents to the pre-programmed scent recovery sequence in order to create a user-specified scent recovery sequence.

49. The integrated system of claim 48 wherein the scents added to the pre-programmed scent recovery sequence overlap in time other scents included in the pre-programmed scent recovery sequence.

50. The integrated system of rein the pre-programmed scent recovery sequence information identifies the duration of recovery of scents from the multimedia and scent-bearing medium and wherein the scent recovery sequence information editing means permits the user to alter the pre-programmed duration of scent recovery in order to create a user-specified scent recovery sequence.

51. The integrated system of claim 50 wherein the pre-programmed scent recovery sequence information editing means permits the user to increase the duration of recovery of certain scents to be recovered from the multimedia and scent-bearing medium in order to create a user-specified scent recovery sequence.

52. The integrated system of claim 50 wherein the pre-programmed scent recovery sequence information editing means permits the user to decrease the duration of recovery of certain scents to be recovered from the multimedia and scent-bearing medium in order to create a user-specified scent recovery sequence.

53. The integrated system of claim 42 further comprising:
wherein the electrostatic scent release means further comprises:
a corona electrode;
associated circuitry for allowing a potential difference to be applied between the corona electrode and a counter electrode; and
wherein the scent recovery means further comprises:
a control signal generation means for interpreting the scent
recovery sequence information and for converting the scent
recovery sequence information into a control signal;
a counter electrode for operation in conjunction with the corona electrode of the electrostatic scent release means;
a high voltage power supply capable of imparting a potential difference between the corona electrode and counter electrode of sufficient strength to sustain corona discharge between the corona electrode and counter electrode to aid in scent release;

high voltage circuitry for connecting the high voltage power supply to the associated circuitry of the electrostatic scent release means and the counter electrode;

corona discharge-control means for detecting the control signal generated by the control signal generation means and for switching the high voltage power supply to an "on" position or an "off" position in dependence on the control signal, wherein when "on" the corona discharge control means allows scent release and when "off" the corona discharge control means prevents scent release.

54. The integrated system of claim 53 further comprising: wherein said scent recovery means further comprises:

ductwork immediately adjacent to the multimedia and scent storage means wherein the scents released from the multimedia and scent storage means may be vented to the user of the integrated system.

55. The integrated system of claim 54 wherein the ductwork extends directly underneath the nose of a user.

56. The integrated system of claim 54 wherein the scent recovery means further comprises:

a fan means for providing a positive pressure to assist in the venting of the released scents.

57. The integrated system of claim 30 further comprising: an input connection for accepting a remote multimedia signal from a remote source.

58. The integrated system of claim 57 wherein the remote multimedia signal further comprises:

scent recovery information for controlling the recovery of scents stored in the multimedia and scent-bearing storage medium.

59. The integrated system of claim 57 wherein the remote multimedia signal further comprises a digitally-encoded audio signal.

60. The integrated system of claim 57 wherein the audio signal is encoded in the MP3 format.

61. The integrated system of claim 56 wherein the remote multimedia signal further comprises a digitally-encoded video signal.

62. The integrated system of claim 57 wherein the remote multimedia signal further comprises digitally-encoded photographs.

63. The integrated system of claim 57 wherein the remote multimedia signal further comprises digitally-encoded textual information.

64. The integrated system of claim 57 wherein the remote multimedia signal further comprises digitally-encoded graphical information.

65. The integrated system of claim 57 wherein the remote multimedia signal is segregated into separately-recoverable segments for use with an interactive playback system.

66. The integrated system of claim 65 wherein the remote multimedia signal further comprises tag information for identifying which scents stored on the multimedia and scent-bearing storage medium are to be recovered in conjunction with the separately-recoverable segments.

67. The integrated system of claim 30 wherein the multimedia information is segregated into separately-recoverable segments for use with an interactive playback system.

68. The integrated system of claim 67 wherein the scent recovery information further comprises tag information for tagging particular scents to particular separately= recoverable multimedia segment.

69. The integrated system of claim 51 further comprising local storage means for storing the multimedia sign covered from the remote source.

70. The integrated system of claim 30 further comprising local storage means for storing the multimedia signal recovered from the multimedia storage means of the multimedia and scent-bearing medium.

71. The integrated system of claims wherein the multimedia and scent-bearing medium further comprises:

a housing having a plurality of storage slots;

a plurality of canisters for positioning in the storage slots, each of the canisters for storing scent, and each of said canisters also having a release valve for releasing the scents stored in the canisters; and wherein the scent identification means identifies which scents are loaded in the housing.

72. The integrated system of claim 71 wherein the scent identification means comprises bar codes.

73. The integrated system of claim 30 wherein the multimedia storage means further comprises a substrate suitable for optically-encoding multimedia information for laser playback or recovery.

74. The integrated system of claim 30 wherein the multimedia storage means further comprises a substrate suitable for magnetically-encoding multimedia information for magnetic playback or recovery.

75. The integrated system of claim 46 further comprising:

user-specified scent recovery sequence storage, means for storing the user-specified scent recovery sequence created with the scent recovery editing means.

76. The integrated system of claim 75 further comprising:

user-specified scent recovery sequence transmission means for transmitting the user-specified scent recovery sequence created with the scent recovery editing means to another user.

77. An integrated multimedia playback and scent recovery system comprising a multimedia and scent-bearing medium and a kiosk, wherein said multimedia and scent-bearing medium comprises:

multimedia storage means for storing multimedia information;

scent storage means for storing at least one scent;

scent identification means for storing scent identification information for use by the kiosk to identify the scent stored in the scent storage means;

an electrostatic scent release means for electrostatically releasing scent from the scent storage means; and an electrical connection for accepting electric potential for use by the electrostatic scent release means; and wherein the kiosk comprises:

a housing;

a multimedia playback system for recovering multimedia information comprising audio information and video information from the multimedia and scent-bearing medium;

scent, identification information recovery means for recovering the scent identification information from the scent identification means;

speaker and amplification means for amplifying and playing back through the speakers the audio information recovered from the multimedia and scent-bearing medium;

video display means for visually displaying video information recovered from the multimedia and scent bearing medium;

scent recovery aid venting means for recovering scent from the multimedia and scent bearing medium and for venting the recovered scent to the vicinity of a human user of the system;

an electrical supply for providing electricity to the multimedia and scent-bearing medium through its electrical connection; and multimedia playback and scent recovery initiation means for initiating multimedia playback and scent recovery from the multimedia and scent-bearing medium.

78. The integrated multimedia playback and scent recovery system of claim 77 wherein the multimedia and scent-bearing medium encodes scent recovery sequence information for synchronizing scent recovery from the multimedia and scent-bearing medium with the multimedia information recovered from the multimedia and scent-bearing medium.

79. The integrated multimedia playback and scent recovery system of claim 77 wherein the multimedia playback and scent recovery initiation means further comprises:

a user input control system for allowing a user to initiate multimedia playback and scent recovery.

80. The integrated multimedia playback and scent recovery system of claim 77 wherein the multimedia playback and scent recovery initiation means further comprises:

a human proximity sensor for detecting the presence of a human being in close proximity to the integrated multimedia playback and scent recovery system and for automatically initiating multimedia playback and scent recovery when a human user is detected in close proximity to the integrated multimedia playback and scent recovery system.

81. The integrated system of claim 80 wherein the human proximity sensor comprises an infrared sensor.

82. The integrated system of claim 80 wherein the human proximity sensor comprises a voice sensor.

83. The integrated system of claim 80 wherein the human proximity sensor comprises a motion sensor.

84. A multimedia and scent-bearing medium for use in combination with a separate, integrated multimedia playback and scent recovery system, wherein the separate, integrated multimedia playback and scent recovery system which comprises at least one scent release electrode, the multimedia and scent-bearing medium comprising:

multimedia storage means for storing multimedia information;

scent storage means for storing at least one scent;

scent identification means for storing scent identification information for use by the separate, integrated multimedia playback and scent recovery system in identifying the scent stored in the scent storage means;

an electrostatic scent release means for electrostatically releasing scent from the scent storage means, wherein the electrostatic scent release means further comprises;

at least one scent release electrode for cooperating with the scent release electrode of the separate, integrated multimedia playback and scent release system; and an electrical connection so that a potential difference may be imparted between the scent release electrodes of the separate, integrated multimedia playback and scent recovery system and the multimedia and scent-bearing medium; and wherein the separate multimedia storage means, scent storage means, scent identification means and electrostatic scent release means of the multimedia and scent-bearing medium together comprise an integrated unit.

85. The multimedia and scene-bearing medium of claim 84 wherein the scent storage means stores a plurality of scents and wherein the scent identification means identifies each of the plurality of scents that are stored in the scent storage means.

86. The multimedia and scent-bearing medium of claim 85 wherein the multimedia information further comprises:

scent recovery sequence information for controlling the sequential recovery of separate scents stored in the multimedia and scent-bearing medium.

87. The multimedia and scent-bearing medium of claim 85 the scent storage means storing the plurality of scents further comprises:

a plurality of partially-enclosed three-dimensional regions each having an upwardly-facing opening and each for storing a separate scent;

an inert storage mediun deposited within the three-dimensional regions for storing separate, electrostatically-releasable scents deposited within the inert storage medium;

a gas-permeable membrane placed over the upwardly-facing openings, wherein the gas-permeable membrane permits the scents to escape from the three-dimensional regions when the scents are electrostatically released; and wherein the electrostatic scent release means further comprises a plurality of scent release electrodes, wherein at least one each of the plurality of scent release electrodes is positioned within each of the partially-enclosed three-dimensional regions, and wherein during scent release operations the scent release electrodes positioned within the partially-enclosed three-dimensional regions cooperate with the scent release electrode of the separate, integrated multimedia playback and scent recovery system to release scents stored within the partially-enclosed three-dimensional regions.

88. The multimedia and scent-bearing medium of claim 84 wherein the scent storage means further comprises:

a plurality of partially-enclosed three-dimensional regions for storing separate scents, wherein each of the partially-enclosed three-dimensional regions have at least one opening through which scent being stored i the partially-enclosed three-dimensional regions may escape during scent release operations; and wherein the scent identification means identifies which scents arc stored in which partially-enclosed three-dimensional regions; and wherein the electrostatic scent release means further comprises a plurality of scent release electrodes, wherein at least one each of the plurality of scent release electrodes is positioned within each of the partially-enclosed, three-dimensional regions, and wherein during scent release operations the scent release electrodes positioned within the partially-enclosed three-dimensional regions cooperate with the scent release electrode of the separate, integrated multimedia playback and scent recovery system to release scents stored within the partially-enclosed three-dimensional regions.

89. The multimedia and scent-bearing medium of claim 84 wherein the scent storage means further comprises:

a housing having a plurality of storage slots, a plurality of canisters for positioning in the storage slots, each of the canisters for storing separate scent, and each of said canisters also having a release valve for releasing the scents stored in the canisters; and wherein the scent identification means identifies which scents are loaded in which: slots of the housing.

90. The multimedia and scent-bearing medium of claim 89 wherein the electrostatic scent release means further comprises a plurality of scent release electrodes, wherein at least one scent release electrode of the plurality is positioned near to the scent release valve of each of the canisters, and wherein the,. scent release electrodes of the multimedia and scent-bearing medium cooperate: with the scent release electrode of the separate, integrated multimedia playback and scent recovery system during scent release operations.

91. The multimedia and scent-bearing medium of claim 84 wherein the multimedia storage means further comprises a substrate suitable for optically encoding multimedia information for laser playback.

92. The multimnedia and scent-bearing medium of claim 84 wherein the multimedia storage means further comprises a magnetic media suitable for magnetically encoding multimedia information for magnetic playback.

93. A multimedia and scent-bearing medium for use in combination with a separate, integrated multimedia playback and scent recovery system, wherein the multimedia and scent-bearing medium further comprises:
   multimedia storage means for storing multimedia information;
   scent storage means for storing at least one scent;
   scent identification means for storing scent identification information for use by the separate,. integrated multimedia playback and scent recovery system to identify the scent stored in the scent storage means,
   an electrostatic scent release means for electrostatically releasing scent from the scent storage means, wherein the electrostatic scent release mean further comprises:
      at least one pair of electrodes, wherein when a potential difference is applied to the pair of electrodes, the scent stored in the scent storage means is ionized and released from the scent storage means; and
      wherein the separate multimedia storage means, scent storage means, scent identification means and electrostatic scent release means of the multimedia and scent-bearing medium together comprise an entered unit.

94. The multimedia and scent-bearing medium of claim 93 wherein the scent storage means stores a plurality of scents and wherein the scent identification means identifies each of the plurality of scents that are stored in the scent storage means.

95. The multimedia and scent-bearing medium of claim 94 wherein the scent storage means storing the plurality of scents further comprises:
   a plurality of partially-enclosed three-dimensional regions each having an upwardly-facing opening and each for storing a separate scent;
   an inert storage medium deposited within the three-dimensional regions for storing separate, electrostatically-releasable scents deposited within the inert storage medium; and
   a gas-permeable membrane placed over the upwardly-facing openings, wherein the gas-permeable membrane permits the scents to escape from the three-dimensional regions when the scents are electrostatically released; and wherein the electrostatic scent release meats further comprises a plurality of pairs of scent release electrodes, wherein at least one pair of scent release electrodes of the plurality of pairs of scent release electrodes is positioned within each of the partially-enclosed, three-dimensional regions, and wherein each pair of scent release electrodes serve to ionize scent stored in the partially-enclosed three-dimensional regions during scent release operations.

96. The multimedia and scent-bearing medium of claim 93 wherein the scent storage means further comprises:
   a plurality of partially-enclosed three-dimensional regions for storing separate scents, wherein each of the partially-enclosed three-dimensional regions have at least one opening through which scent being stored in the partially-enclosed three-dimensional regions may escape during scent release operations; and
   wherein the scent identification means identifies which scents are stored in which partially-enclosed three-dimensional regions; and
   wherein the electrostatic scent release means further comprises a plurality of pairs of scent release electrodes, wherein at least one pair of scent release electrodes of the plurality of pairs of scent release creches is positioned within each of the partially-enclosed, three-dimensional regions, and wherein each pair of scent release electrodes serve to ionize scent stored in the partially-enclosed three-dimensional regions during scent release operations.

97. The multimedia and scent-bearing medium of claim 93 wherein the multimedia, storage means further comprises a substrate suitable for optically encoding multimedia information for laser playback.

98. The multimedia and scent-bearing medium of claim 93 wherein the multimedia storage means further comprises a magnetic media suitable for magnetically encoding multimedia information for magnetic playback.

99. The multimedia and scent-bearing medium of claim 93 wherein the scent storage means further comprises:
   a housing having a plurality of storage slots;
   a plurality of canisters for positioning in the storage slots, each of the canisters for storing separate scent, and each of said canisters also having a release valve for releasing the scents stored in the canisters; and
   wherein the scent identification means identifies which scents are load in which slots of the housing.

100. The multimedia and scent-bearing medium of claim 93 wherein the electrostatic scent release means further comprises a plurality of pairs of scent release electrodes, wherein at least one pair of the plurality of pairs of scent release electrodes is positioned near to tie scent release valves of each of the canisters, and wherein the pairs of electrodes ionize scent as the scent is released from the canisters during scent release operations.

* * * * *